US011981752B2

(12) United States Patent
Pang et al.

(10) Patent No.: US 11,981,752 B2
(45) Date of Patent: May 14, 2024

(54) TUMOR ASSOCIATED MONOCYTE/MACROPHAGE BINDING PEPTIDE AND METHODS OF USE THEREOF

(71) Applicant: Sanford Burnham Prebys Medical Discovery Institute, La Jolla, CA (US)

(72) Inventors: Hongbo Pang, La Jolla, CA (US); Erkki Ruoslahti, La Jolla, CA (US)

(73) Assignee: Sanford Burnham Prebys Medical Discovery Institute, La Jolla, CA (US)

( * ) Notice: Subject to any disclaimer, the term of this patent is extended or adjusted under 35 U.S.C. 154(b) by 571 days.

(21) Appl. No.: 16/607,043

(22) PCT Filed: May 1, 2018

(86) PCT No.: PCT/US2018/030498
§ 371 (c)(1),
(2) Date: Jun. 11, 2020

(87) PCT Pub. No.: WO2018/204392
PCT Pub. Date: Nov. 8, 2018

(65) Prior Publication Data
US 2020/0190142 A1 Jun. 18, 2020

Related U.S. Application Data

(60) Provisional application No. 62/500,224, filed on May 2, 2017.

(51) Int. Cl.
*A61K 38/00* (2006.01)
*A61K 38/04* (2006.01)
*A61K 47/69* (2017.01)
*C07K 7/06* (2006.01)

(52) U.S. Cl.
CPC ............ *C07K 7/06* (2013.01); *A61K 47/6911* (2017.08); *A61K 38/00* (2013.01)

(58) Field of Classification Search
CPC .... A61K 38/00; A61K 38/04; A61K 47/6911; A61K 47/69; C07K 7/06
See application file for complete search history.

(56) References Cited

U.S. PATENT DOCUMENTS

| | | | |
|---|---|---|---|
| 5,897,945 | A | 4/1999 | Lieber |
| 5,916,596 | A | 6/1999 | Desai |
| 6,506,405 | B1 | 1/2003 | Desai |
| 6,530,944 | B2 | 3/2003 | West |
| 6,537,579 | B1 | 3/2003 | Desai |
| 6,759,199 | B2 | 7/2004 | Mirkin |
| 8,367,621 | B2 * | 2/2013 | Ruoslahti ........... A61K 49/0043 514/21.1 |
| 2005/0004002 | A1 | 1/2005 | Desai |
| 2009/0246133 | A1 | 10/2009 | Ruoslahti |

OTHER PUBLICATIONS

Buss et al., "Nanoparticle delivery of immunostimulatory oligonucleotides enhances response to checkpoint inhibitor therapeutics," PNAS, Jun. 16, 2020, 117(24): 13428-13436. (Year: 2020).*
Ruoslahti, Erkki, "Probing Tumor Microenvironment with In Vivo Phage Display," Defense Technical Information Center, Accession No. ADA621073, https://apps.dtic.mil/sti/pdfs/ADA621073.pdf, pp. 1-18, Sep. 2014. (Year: 2014).*
Accession No. ADA621073, cover page, Defense Technical Information Center, pp. 1-2. Sep. 2014. (Year: 2014).*
Kim et al., "Immunogene therapy with fusogenic nanoparticles modulates macrophage response to *Staphylococcus aureeus*," Nature Communications, 2018, 9: 1969, pp. 1-13. (Year: 2018).*
Akashi, et al., "Anticancer effects of gemcitabine are enhanced by co-administered iRGD peptide in murine pancreatic cancer models that overexpressed neuropilin-1." Br. J. Cancer 110:1481-1487 (2014).
Allavena, et al., "The inflammatory micro-environment in tumor progression: The role of tumor-associated macrophages", Critical Reviews in Oncology/Hematology, 66(1):1-9 (2008).
Bergstrom, et al., "TLR8 Senses Staphylococcus aureus RNA in Human primary Monocytes and Macrophages and Induces IFN-Beta Production via a TAK1-IKKbeta-IRF5 signaling Pathway", J. Immunol., 195:1100-1111 (2015).
Bingle, et al., "The role of tumour☐associated macrophages in tumour progression: implications for new anticancer therapies", The Journal of Pathology, 196(3): 254-265 (2002).
Birbrair, et al., "Type-2 pericytes participate in normal and tumoral angiogenesis", American Journal of Physiology Cell Physiology. 307(1): C25-C38 (2014).
Burke, et al., "Macrophages in gene therapy: cellular delivery vehicles and in vivo targets", J. Leukoc. Biol., 72:417-428 (2002).
Cieslewicz, et al., "Targeted delivery of proapoptotic peptides to tumor-associated macrophages improves survival" Proc. Natl. Acad. Sci. USA, 110(40): 15919-24 (2013).
Courties, et al., "In vivo silencing of the transcription factor IRF5 reprograms the macrophage phenotype and improves infarct healing", J. Am. Coll. Cardiol., 63:1556-1566 (2014).
Coussens, et al., "Neutralizing tumor-promoting chronic inflammation: a magic bullet?" Science, 339(6117):286-291 (2013).
Davies, et al., "Origins and Evolution of Antibiotic Resistance", Microbiol. Mol. Biol. Rev., 74:417-433 (2010).
Eames, et al., "KAP1/TRIM28: An inhibitor of IRF5 function in inflammatory macrophages", Immunobiology, 217:1315-1324 (2012).
Fogal, et al., "Mitochondrial/Cell-Surface Protein p32/gC1qR as a Molecular Target in Tumor Cells and Tumor Stroma" Cancer Res, 68(17):7210-7218 (2008).
Franklin, et al., "The cellular and molecular origin of tumor-associated macrophages", Science, 344:921-925 (2014).

(Continued)

*Primary Examiner* — Julie Ha
(74) *Attorney, Agent, or Firm* — PABST PATENT GROUP LLP

(57) ABSTRACT

Disclosed are compositions and methods useful for targeting molecules to activated macrophages, such as tumor associated macrophages. The compositions and methods are based on peptide sequences, such as AMT peptides, that home to activated macrophages. The disclosed homing to activated macrophages is useful for delivering therapeutic and detectable agents to cells and tissues where immune system effects or inflammation are occurring.

47 Claims, 3 Drawing Sheets

Specification includes a Sequence Listing.

(56) References Cited

OTHER PUBLICATIONS

Gabrilovich, "Fatal attraction: How macrophages participate in tumor metastases", The Journal of Experimental Medicine, 212(7): 976-976 (2015).
Germano, et al., "Role of macrophage targeting in the antitumor activity of trabectedin", Cancer Cell, 23(2): 249-262 (2013).
Hall, et al., "Could Silencing IRF5 Improve Healing of a Myocardial Infarct through the Reprogramming of the Macrophage Population", J. Am. Coll. Cardiol., 63:1567-1568 (2014).
Hamzah, et al., "Specific penetration and accumulation of a homing peptide within atherosclerotic plaques of apolipoprotein E-deficient mice", Proc. Natl. Acad. Sci., 108(17):7154-7159 (2011).
Harvey, et al., "Targeting Nrf2 Signaling Improves Bacterial Clearance by Alveolar Macrophages in Patients with COPD and in a Mouse Model", Sci. Transl. Med., 3:78ra32 (2011).
Jain, et al., "Normalization of Tumor Vasculature: An Emerging Concept in Antiangiogenic Therapy", Science, 307:58 (2005).
Krausgruber, et al., "IRF5 promotes inflammatory macrophage polarization and TH1-TH17 responses", Nat. Immunol., 12:231-238 (2011).
Laakkonen, et al., "A tumor-homing peptide with a lymphatic vessel-related targeting specificity", Nature Med., 8:743-751 (2002).
Laakkonen, et al., "Antitumor activity of a homing peptide that targets tumor lymphatics and tumor cells", Proc. Natl. Acad. Sci. USA., 101:9381-9386 (2004).
Lee, et al., "Nano—and micro-based inhaled drug delivery systems for targeting alveolar macrophages", Expert. Opin. Drug. Deliv., 12:1009-1026 (2015).
Lewis, et al., "Distinct Role of Macrophages in Different Tumor Microenvironments", Cancer Research, 66(2): 605-612 (2006).
Lin, et al., "Photonic pseudo-gap-based modification of photoluminescence from CdS nanocrystal satellites around polymer microspheres in a photonic crystal", Appl. Phys Lett., 81(17):3134 (2002).
Mantovani, et al., "Cancer-related inflammation", Nature, 454(7203):436-444 (2008).
Mantovani, et al., "The interaction of anticancer therapies with tumor-associated macrophages", J. Exp. Med., 212(4):435-45 (2015).
Moldoveanu, et al., "Inflammatory mechanisms in the lung", J. Inflamm. Res., 2:1-11 (2009).
Ngambenjawong, et al, "Serum Stability and Affinity Optimization of an M2 Macrophage-Targeting Peptide (M2pep)", Theranostics, 6(9):1403-1414 (2016a).
Ngambenjawong, et al., "Synthesis and evaluation of multivalent M2pep peptides for targeting alternatively activated M2 macrophages", J. Control. Release, 224:103-111 (2016b).
Noy, et al., "Tumor-associated macrophages: from mechanisms to therapy", Immunity, 41(1):49-61 (2014).
Paasonen, et al., "New p32/gC1qR ligands for targeted tumor delivery." Chembiochem. 17(7):570-575 (2016).
Pang, et al., "An endocytosis pathway initiated through neuropilin-1 and regulated by nutrient availability." Nat. Comm., 5:4904 (2014a).
Pang, et al., "A free cysteine prolongs the half-life of a homing peptide and improves its tumor-penetrating activity", Journal of Controlled Release, 175:48-53 (2014b).
Panni, et al., "Targeting tumor-infiltrating macrophages to combat cancer", Immunotherapy, 5(10):1075-87 (2013).
Provenzano, et al., "Hyaluronan, fluid pressure, and stromal resistance in pancreas cancer", Br. J. Cancer, 108:1-8 (2013).
Ries, et al., "Targeting tumor-associated macrophages with anti-CSF-1R antibody reveals a strategy for cancer therapy", Cancer Cell, 25(6):846-59 (2014).
Roth, et al., "Transtumoral targeting enabled by a novel neuropilin-binding peptide." Oncogene, 31(33):3754-3763 (2003).
Ruoslahti, et al., "Targeting of drugs and nanoparticles to tumors", Journal of Cell Biology, 188(6):759-68 (2010).
Ruoslahti, "Tumor penetrating peptides for improved drug delivery", Adv. Drug Deliv. Rev. pii: S0169-409X(16)30094-1 (2016).
Schmithals, et al., "Improving drug penetrability with iRGD leverages the therapeutic response to sorafenib and doxorubicin in hepatocellular carcinoma", Cancer Res., 75:3147-3154 (2015).
Sha, et al., "Tumor-penetrating peptide fused EGFR single-domain antibody enhances cancer drug penetration into 3D multicellular spheroids and facilitates effective gastric cancer therapy", J. Control. Release, 200:188-200 (2015).
Sharma, et al., "Tumor-penetrating Nanosystem strongly suppresses breast tumor growth", Nano Lett., 17(3):1356-1364 (2017).
She, et al., "Plaque-penetrating peptide inhibits development of hypoxic atherosclerotic plaque", Journal of Controlled Release, 238:212-20 (2016).
Shih, et al., "Tumor-Associated Macrophage: Its Role in Cancer Invasion and Metastasis", Journal of Cancer Molecules, 2(3): 101-106 (2006).
Simberg, et al., "Biomimetic amplification of nanoparticle homing to tumors", PNAS, 104(3):933-936 (2007).
Song, et al., "In vivo Targeting of Alveolar Macrophages via RAFT-Based Glycopolymers", Biomaterials, 33:6889-6897 (2012).
Sugahara, et al., "Co-administration of a tumor-penetrating peptide enhances the efficacy of cancer drugs", Science, 328:1031-1035 (2010).
Sugahara, et al., "Tissue-penetrating delivery of compounds and nanoparticles into tumors", Cancer Cell, 16:510-520 (2009).
Takaoka, et al., "Integral role of IRF-5 in the gene induction programme activated by Toll-like receptors", Nature, 434:243-249 (2005).
Teesalu, et al., "C-end rule peptides mediate neuropilin-1-dependent cell, vascular, and tissue penetration", Proc. Natl. Acad. Sci. USA, 106:16157-16162 (2009).
Teesalu, et al., "Tumor-penetrating peptides", Frontiers in Oncology, 3(216):1-8 (2013).
Teesalu, et al., "Chapter two-Mapping of vascular ZIP Codes by Phage Display", Methods in Enzymology, 503:35-56 (2012).
Thoreau, et al., "Vaccine-induced tumor regression requires a dynamic cooperation between T cells and myeloid cells at the tumor site", Oncotarget, 6:27832-27846 (2015).
Tong, et al., "Nanomedicines Targeting the Tumor Microenvironment", Cancer J., 21(4):314-321 (2015).
Wang, et al., "Composite Photonic Crystals from Semiconductor Nanocrystal/Polyelectrolyte-Coated Colloidal Spheres", Chem. Mater., 15:2724-2729 (2003).
Weintraub, "Releasing the brakes", Nature, 504(7480):S6-8 (2013).
Weiss, et al., "IRF5 controls both acute and chronic inflammation", Proc. Natl. Acad. Sci. U.S.A., 112:11001-11006 (2015).
Williams, et al., "Tumor-associated macrophages: unwitting accomplices in breast cancer malignancy", NPJ Breast Cancer, 2:15025 (2016).
Zhang, et al., "Lymphatic zip codes in premalignant lesions and tumors", Cancer Res. 66:5696-5706 (2006).
Zou, "Regulatory T cells, tumour immunity and immunotherapy", Nature Reviews Immunology, 6(4):295-307 (2006).
International Search Report and Written Opinion for corresponding PCT application PCT/US2018/030498 dated Jul. 30, 2018.

* cited by examiner

FIG. 2

SEQUENCE LISTING

<160> NUMBER OF SEQ ID NOS: 19

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1

Cys Arg Val Leu Arg Ser Gly Ser Cys
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 2

Arg Val Leu Arg Ser Gly Ser
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(14)
<223> OTHER INFORMATION: D-form amino acids

<400> SEQUENCE: 3

Lys Leu Ala Lys Leu Ala Lys Lys Leu Ala Lys Leu Ala Lys
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 4

Arg Pro Ala Arg Pro Ala Arg
1               5

<210> SEQ ID NO 5
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 5

Lys Leu Ala Lys Lys Leu Ala Lys Leu Ala Lys Leu Ala
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic Pepetide

```
<400> SEQUENCE: 6

Lys Ala Ala Lys Lys Ala Ala Lys Ala Ala Lys Lys Ala Ala
1               5                   10

<210> SEQ ID NO 7
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 7

Lys Leu Gly Lys Lys Leu Gly Lys Leu Gly Lys Lys Leu Gly Lys Leu
1               5                   10                  15

Gly Lys Lys Leu Gly
            20

<210> SEQ ID NO 8
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 8

Ala Arg Ala Leu Pro Ser Gln Arg Ser Arg
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 9

Gly Gly Ser Gly Gly Ser Lys Gly
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 10

Gly Gly Arg Val Leu Arg Ser
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 11

Ser Val Ala Tyr Asp
1               5

<210> SEQ ID NO 12
<211> LENGTH: 7
<212> TYPE: PRT
<213> ORGANISM: Artificial Sequence
<220> FEATURE:
```

```
<223> OTHER INFORMATION: Synthetic Peptide

<400> SEQUENCE: 12

Arg Ser Gly Leu Arg Ser Ser
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 13

Gly Arg Leu Leu Arg Ser Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 14

Gly Arg Met Leu Arg Ser Gly
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 15

Gly Gly Ala Ser Ile Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 16

Ser Val Gly Arg Ser Met Arg Ser
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 17

Gly Arg Val Leu Arg Ser Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 18

Cys Gly Asn Lys Arg Thr Arg Gly Cys
1               5

<210> SEQ ID NO 19
<211> LENGTH: 22
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (6)..(22)
<223> OTHER INFORMATION: Xaa is any amino acid

<400> SEQUENCE: 19

Arg Val Leu Arg Ser Xaa Xaa Xaa Xaa Xaa Xaa Xaa Xaa Xaa Xaa
1               5                   10                  15

Xaa Xaa Xaa Xaa Xaa Xaa
            20
```

TUMOR ASSOCIATED MONOCYTE/MACROPHAGE BINDING PEPTIDE AND METHODS OF USE THEREOF

CROSS REFERENCE TO RELATED APPLICATIONS

This application claims the benefit of the filing date of U.S. Provisional Application No. 62/500,224, which was filed May 2, 2017. The entire content of that prior application is hereby incorporated by reference herein.

STATEMENT REGARDING FEDERALLY SPONSORED RESEARCH

This invention was made with government support under Cooperative Agreement HR0011-13-2-0017 from the Defense Advanced Research Projects Agency (DARPA) and grant CA152327 from the National Institutes of Health (NIH). The government has certain rights in the invention.

REFERENCE TO SEQUENCE LISTING

The Sequence Listing submitted as a text file named "SBMRI_17_012_ST25.txt," created on May 1, 2018 and having a size of 4,302 bytes is hereby incorporated by reference pursuant to 37 C.F.R § 1.52(e)(5).

FIELD OF THE INVENTION

The present invention relates generally to the field of molecular medicine, cancer treatment, and, more specifically, to cell and tissue-targeting peptides.

BACKGROUND OF THE INVENTION

It has been a goal to develop novel tools for targeted delivery of therapeutic and diagnostic agents to tumor-associated macrophages (TAMs). Monocytes/macrophages are the predominant myeloid cell type in many types of solid tumors (e.g., breast cancer). They are partly responsible for creating an immunosuppressive microenvironment in solid tumors, which greatly limits the clinical effectiveness of immunotherapy (Zou, *Nature Reviews Immunology* 6(4): 295-307 (2006); Weintraub, *Nature* 504(7480):56-8 (2013)). They also have some other tumor-promoting activities that thwart other cancer therapies (Noy and Pollard, Immunity 41(1):49-61 (2014)). Currently various agents are being developed to disable/modulate these activities of TAMs (Panni et al., *Immunotherapy* 5(10):1075-87 (2013); Williams et al., *NPJ Breast Cancer* 2:15025 (2016)). However, due to the abundance of macrophages in all normal organs and their important role in innate immunity, current strategies often come with side effects (Williams et al. (2016)). Therefore, there is urgent need for tools that can selectively bind and deliver therapeutic cargo to TAMs.

Phage display technology, displays of large numbers of random peptide sequences on the surface of phages, makes it possible to identify novel sequences that have affinity for cells/proteins of interest (Teesalu et al., *Methods in Enzymology* 503:35-56 (2012)). Using this platform, peptides that selectively recognize certain components in solid tumors have been discovered (Teesalu et al., *Frontiers in Oncology* 3:216 (2013); Ruoslahti et al., *Journal of Cell Biology* 188(6):759-68 (2010)).

Tumor-associated macrophages (TAMs) are a type of cell belonging to the macrophage lineage. They are found in close proximity or within tumor masses (Birbrair et al., *American Journal of Physiology Cell Physiology*. 307 (1): C25-C38 (2014); Shih et al., *Journal of Cancer Molecules* 2(3): 101-106 (2006)).TAMs are derived from circulating monocytes or resident tissue macrophages, which form the major leukocytic infiltrate found within the stroma of many tumor types. The function of TAMs is controversial as there is growing evidence for their involvement in both pro-tumor (e.g., promotion of growth and metastasis through tumor angiogenesis) as well as anti-tumor (tumoricidal and tumorostatic) processes (Birbrair et al. (2014); Bingle et al., *The Journal of Pathology*. 196 (3): 254-265 (2002); Thoreau et al., *Oncotarget* 6:27832-27846 (2015)). TAMs interact with a wide range of growth factors, cytokines and chemokines in the tumor microenvironment, which is thought to educate the TAMs and determine their specific phenotype and hence functional role as the microenvironment varies between different types of tumors. TAMs have therefore been shown to differ in their roles depending on the type of tumor with which they are associated (Lewis and Pollard, *Cancer Research*. 66 (2): 605-612 (2006)). In many tumor types TAM infiltration level has been shown to be of significant prognostic value. TAMs have been linked to poor prognosis in breast cancer, ovarian cancer, types of glioma and lymphoma; better prognosis in colon and stomach cancers and both poor and better prognoses in lung and prostate cancers (Allavena et al., *Critical Reviews in Oncology/Hematology*. 66: 1 (2008)). Macrophages that infiltrate metastatic sites have specific characteristics and are known as metastasis-associated macrophages (MAMs) (Gabrilovich, *The Journal of Experimental Medicine*. 212 (7): 976-976 (2015)).

Deep-tissue Staphyloccocus aureus (Staph. aureus) infection remains one of the most difficult therapeutic challenges today. Staph. aureus is a gram positive bacterium that predominantly infects the skin, and the respiratory system causing pneumonia; the local infections can become systemic in the most serious form of Staphylococcal disease, sepsis (Bergstrom et al., *J. Immunol*. 195, 1100-1111 (2015)). At high levels of bacterial burden in the lungs, Staphyloccocal pneumonia becomes fatal due to two major factors: (1) pathogenic activity by Staph. aureus, and (2) prolonged inflammation caused by the body's immune system. The acute inflammatory response at the site of an infection involves the secretion of cytokines by alveolar macrophages, recruiting polymorphonuclear neutrophils (PMNs) and macrophages from circulation (Johnson et al., *Microbiology and Immunology*. 5th edn, (Lippincott Williams & Wilkins, 2010)). Alveolar inflammation causes extensive bleeding and exudation that slow down vascular flow and impede breathing (Johnson et al., *Microbiology and Immunology*. 5th edn, (Lippincott Williams & Wilkins, 2010); Monton and Torres, *Monaldi. Arch. Chest Dis*. 53, 56-63 (1998)), and prolonged excretion of inflammatory cytokines drastically lowers the chances of recovery (Monton and Torres (1998)). Although the immediate inflammatory response to Staphylococcal pneumonia is necessary for rapid elimination of the threat, it must be balanced with anti-inflammatory and tissue-reparative actions to maintain lung homeostasis (Moldoveanu et al., *J. Inflamm. Res*. 2, 1-11 (2009)).

Due to toxic side effects of small molecule antibiotics such as vancomycin (Davies and Davies, *Microbiol. Mol. Biol. Rev*. 74, 417-433 (2010)) and the emergence of strains resistant to these therapeutics (Johnson et al., *Microbiology* and Immunology. 5th edn, (Lippincott Williams & Wilkins, 2010)), there is increasing emphasis on therapies that can harness the immune system to treat bacterial infections (Song et al., *Biomaterials* 33, 6889-6897 (2012); Lee et al., *Expert. Opin. Drug. Deliv.* 12, 1009-1026 (2015); Harvey et al., *Sci. Transl. Med.* 3, 78ra32 (2011); Burke et al., *J. Leukoc. Biol.* 72, 417-428 (2002)). Macrophages are one potential target for these therapies due to their dual role in inflammatory, immune stimulatory phagocytes (M1 macrophages) and as anti-inflammatory phagocytes (M2 macrophages) associated with bacterial phagocytosis and tissue repair functions (Courties et al., *J. Am. Coll. Cardiol.* 63, 1556-1566 (2014); Eames et al., *Immunobiology* 217, 1315-1324 (2012); Hall and Wei, *J. Am. Coll. Cardiol.* 63, 1567-1568 (2014); Krausgruber et al., *Nat. Immunol.* 12, 231-238 (2011); Takaoka et al., *Nature* 434, 243-249 (2005); Weiss et al., *Proc. Natl. Acad. Sci. U.S.A.* 112, 11001-11006 (2015)).

However, targeting and modulating macrophages has proven difficult. Thus, there is a need for compositions and therapeutics for targeting and effectively modulating activated macrophages.

It is an object of the present invention to provide compositions and methods for targeting and effectively modulating activated macrophages.

BRIEF SUMMARY OF THE INVENTION

Disclosed are peptides, conjugates, compositions and methods useful for targeting activated macrophages, such as tumor associated macrophages. In particular, disclosed are isolated peptides comprising an activated macrophage targeting (AMT) amino acid sequence. In some forms, the AMT amino acid sequence has the formula $X_1$—R—$X_2$-L-R—S—$X_3$, wherein $X_1$ and $X_3$ can each be, independently, zero to four amino acids, wherein $X_2$ can be one or two amino acids, wherein the amino acids of $X_1$, $X_2$, and $X_3$ can be any amino acid. In some forms, the peptide selectively binds to activated macrophages via the AMT amino acid sequence. Generally, an AMT amino acid sequence binds to a receptor on the surface of activated macrophages. As a consequence, a peptide that selectively binds to activated macrophages via the AMT amino acid sequence will be structured to have the AMT amino acid sequence exposed and available for binding to the receptor on the surface of activated macrophages.

In some forms, the peptide comprises the sequence RVLRSGS (SEQ ID NO:2), GGRVLRS (SEQ ID NO:10), RSGLRSS (SEQ ID NO:12), GRLLRSG (SEQ ID NO:13), GRMLRSG (SEQ ID NO:14), or GRVLRSS (SEQ ID NO:17). In some forms, the peptide comprises the sequence CRVLRSGSC (SEQ ID NO:1). In some forms, the peptide is cyclic. In some forms, the peptide is a modified peptide. In some forms, the peptide is a methylated peptide. In some forms, the methylated peptide comprises a methylated amino acid segment. In some forms, the peptide is N- or C-methylated in at least one position.

Also disclosed are compositions comprising one or more of the disclosed peptides. In some forms, the composition further comprises a co-composition, wherein the peptide and the co-composition are not covalently coupled or directly non-covalently associated with each other. In some forms, the composition further comprises a cargo composition, wherein the peptide and the cargo composition are covalently coupled or non-covalently associated with each other.

In some forms, the peptide selectively homes to activated macrophages. In some forms, the peptide selectively homes to tumor associated macrophages. In some forms, the co-composition or cargo composition comprises a therapeutic agent. In some forms, the co-composition or cargo composition comprises a detectable agent. In some forms, the co-composition or cargo composition comprises a carrier, vehicle, or both.

In some forms, the co-composition or cargo composition comprises a therapeutic protein, a therapeutic compound, a therapeutic composition, a cancer chemotherapeutic agent, a toxin, a cytotoxic agent, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, a pro-apototic agent, a pro-inflammatory agent, an immunostimulating agent, an anti-inflammatory agent, an immunosuppressing agent, an anti-angiogenic agent, an anti-bacterial agent, or a combination.

In some forms, the peptide is comprised in an AMT composition. In some forms, the AMT composition comprises one or more cargo compositions. In some forms, the AMT composition further comprises one or more copies of the peptide. In some forms, the peptide is comprised in an AMT conjugate. In some forms, the AMT conjugate comprises one or more cargo compositions. In some forms, the AMT conjugate comprises one or more copies of the peptide.

In some forms, the composition comprises a plurality of cargo compositions. In some forms, the composition comprises a plurality of copies of the peptide. In some forms, the composition comprises a plurality of co-compositions.

In some forms, the composition further comprises a surface molecule. In some forms, the peptide is conjugated with the surface molecule. In some forms, one or more of the conjugated peptides is indirectly conjugated to the surface molecule via a linker. In some forms, the composition further comprises a plurality of linkers. In some forms, at least one of the linkers comprises polyethylene glycol.

In some forms, the composition binds activated macrophages. In some forms, the composition is internalized in cells. In some forms, the composition reduces an inflammatory response. In some forms, the composition reduces one or more effects of an infection. In some forms, the composition increases an inflammatory response. In some forms, the composition promotes apoptosis. In some forms, the composition reduces growth or proliferation of an infectious agent. In some forms, the composition reduces tumor growth.

In some forms, the surface molecule comprises a nanoparticle, a nanoworm, an iron oxide nanoworm, an iron oxide nanoparticle, an albumin nanoparticle, a liposome, a micelle, a phospholipid, a polymer, a microparticle, or a fluorocarbon microbubble.

In some forms, the composition further comprises one or more copies of the peptide. In some forms, the composition comprises at least 100 copies of the peptide. In some forms, the composition comprises at least 1000 copies of the peptide.

In some forms, the composition further comprises one or more moieties. In some forms, the moieties are independently selected from the group consisting of a pro-apototic agent, a pro-inflammatory agent, an immunostimulating agent, an anti-inflammatory agent, an immunosuppressing agent, an anti-angiogenic agent, a pro-angiogenic agent, a cancer chemotherapeutic agent, an anti-bacterial agent, a cytotoxic agent, a polypeptide, a nucleic acid molecule, a small molecule, an image contrast agent, a fluorophore, fluorescein, rhodamine, a radionuclide, indium-111, technetium-99, carbon-11, and carbon-13.

In some forms, at least one of the moieties is a therapeutic agent. In some forms, the therapeutic agent is an anti-cancer agent. In some forms, the therapeutic agent inhibits expression of the phosphotidylinositide 3-kinase (PI3K) gamma gene. In some forms, the therapeutic agent inhibits PI3K gamma. In some forms, the therapeutic agent can be a PI3K gamma inhibitor (such as TG100-115), and TNF-alpha. In some forms, at least one of the moieties is a detectable agent. In some forms, the detectable agent is FAM.

In some forms, the composition further comprises one or more copies of the peptide and, wherein the peptides are conjugated to the liposome, wherein the peptides each comprise the sequence CRVLRSGSC (SEQ ID NO:1), wherein the peptides are cyclic.

Also disclosed are method of using the disclosed peptides, conjugates, and compositions. In some forms, the method comprises exposing activated macrophages to a disclosed composition, wherein the composition selectively binds to the activated macrophages. In some forms, the activated macrophages are in a subject. In some forms, the activated macrophages are exposed to the composition by administering the composition to the subject.

In some forms, the composition has a therapeutic effect. In some forms, the therapeutic effect comprises a reduction in inflammation, an increase in inflammation, an increase in apoptosis, a reduction in growth or proliferation of an infectious agent, an increase in speed of wound healing, reduction in amounts of scar tissue, decrease in pain, decrease in swelling, or decrease in necrosis. In some forms, the therapeutic effect comprises decrease in inflammatory immune response. In some forms, the therapeutic effect comprises increase in inflammatory response. In some forms, the therapeutic effect comprises increase in apoptosis. In some forms, the composition reduces growth or proliferation of an infectious agent.

In some forms, the subject has a disease or condition. In some forms, the disease is cancer. In some forms, the disease is microbial infection.

In some forms, the composition selectively homes to activated macrophages. In some forms, the composition selectively homes to tumor associated macrophages.

Disclosed are peptides that target tumor associated macrophages. The disclosed peptides can also mediate targeting of compounds and compositions coupled to, associated with, conjugated to, or even co-administered with the peptide. Examples of the disclosed peptides include peptides where the peptide comprises the amino acid sequence RVLRSGS (SEQ ID NO:2) and peptides consisting of RVLRSGS (SEQ ID NO:2). The disclosed peptides can be used in and with a variety of compositions and methods to, for example, enhancing targeting, delivery, or both of such compositions into or through a cell, tissue, or both. Such compositions and methods are also disclosed herein.

Disclosed are peptides where the peptide comprises the amino acid sequence RVLRSGS (SEQ ID NO:2). In some forms, the peptide can be a modified peptide. In some forms, the peptide can be a methylated peptide. In some forms, one or more of the methylated peptide can comprise a methylated amino acid segment. In some forms, the peptide can be N- or C-methylated in at least one position.

Also disclosed are compositions comprising the disclosed peptide. In some forms, the composition can further comprise a co-composition, where the peptide and the co-composition are not covalently coupled or directly non-covalently associated with each other. In some forms, the composition can further comprise a cargo composition, where the peptide and the cargo composition are covalently coupled or non-covalently associated with each other.

In some forms, the peptide can selectively home to activated macrophages. In some forms, the peptide can selectively home to tumor associated macrophages. In some forms, the peptide and the co-composition are not bound to each other. In some forms, the co-composition and/or cargo composition can comprise a therapeutic agent. In some forms, the co-composition and/or cargo composition can comprise a detectable agent. In some forms, the co-composition and/or cargo composition can comprise a carrier, vehicle, or both. In some forms, the co-composition and/or cargo composition can comprise a therapeutic protein, a therapeutic compound, a therapeutic composition, a cancer chemotherapeutic agent, a toxin, a cytotoxic agent, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, a pro-apotoptic agent, a pro-inflammatory agent, an immunostimulating agent, an anti-inflammatory agent, an immunosuppressing agent, an anti-angiogenic agent, an anti-bacterial agent, or a combination.

In some forms, the peptide can be an activatable peptide. The activatable peptide can be a protease-activatable peptide. The protein or peptide can be circular. The protein or peptide can be linear.

In some forms, the peptide can be comprised in an AMT composition. In some forms, the AMT composition can comprise one or more cargo compositions. In some forms, the AMT composition can comprise one or more homing molecules. In some forms, the peptide can be comprised in an AMT conjugate. In some forms, the AMT conjugate can comprise one or more cargo compositions. In some forms, the AMT conjugate can comprise one or more homing molecules. In some forms, the composition can comprise a plurality of cargo compositions. In some forms, the composition can comprise a plurality of copies of the peptide. In some forms, the composition can comprise a plurality of co-compositions.

In some forms, the composition can further comprise a surface molecule and a plurality of membrane perturbing molecules. In some forms, one or more of the membrane perturbing molecules can comprise the amino acid sequence $_D$(KLAKLAK)$_2$ (SEQ ID NO:3) or a conservative variant thereof, (KLAKLAK)$_2$ (SEQ ID NO:3) or a conservative variant thereof, (KLAKKLA)$_2$ (SEQ ID NO:5) or a conservative variant thereof, (KAAKKAA)$_2$ (SEQ ID NO:6) or a conservative variant thereof, or (KLGKKLG)$_3$ (SEQ ID NO:7) or a conservative variant thereof, or a combination. In some forms, one or more of the membrane perturbing molecules can comprise the amino acid sequence $_D$(KLAKLAK)$_2$ (SEQ ID NO:3), (KLAKLAK)$_2$ (SEQ ID NO:3), (KLAKKLA)$_2$ (SEQ ID NO:5), (KAAKKAA)$_2$ (SEQ ID NO:6), or (KLGKKLG)$_3$ (SEQ ID NO:7), or a combination. In some forms, one or more of the membrane perturbing molecules can comprise the amino acid sequence $_D$(KLAKLAK)$_2$ (SEQ ID NO:3) or a conservative variant thereof. In some forms, one or more of the membrane perturbing molecules can comprise the amino acid sequence $_D$(KLAKLAK)$_2$ (SEQ ID NO:3).

In some forms, the composition can further comprise one or more peptides, wherein the peptides selectively home to tumor associated macrophages. In some forms, the peptides can be conjugated with the surface molecule. In some forms, one or more of the conjugated peptides can be indirectly conjugated to the surface molecule via a linker. In some forms, the composition can further comprise a plurality of linkers. In some forms, at least one of the linkers can comprise polyethylene glycol.

In some forms, the composition can bind inside tumor blood vessels. In some forms, the composition can be internalized in cells. In some forms, the composition can reduce tumor growth.

In some forms, the surface molecule can comprise a nanoparticle, a nanoworm, an iron oxide nanoworm, an iron oxide nanoparticle, an albumin nanoparticle, a liposome, a micelle, a phospholipid, a polymer, a microparticle, or a fluorocarbon microbubble. In some forms, the composition can comprise at least 100 copies of the peptide. In some forms, the composition can comprise at least 1000 copies of the peptide. In some forms, the composition can comprise at least 10,000 copies of the peptide. In some forms, the composition can comprise at least 100 membrane perturbing molecules. In some forms, the composition can comprise at least 1000 membrane perturbing molecules. In some forms, the composition can comprise at least 10,000 membrane perturbing molecules.

In some forms, the composition, AMT composition, co-composition, or cargo composition can comprise a plurality of surface molecules, a plurality of peptides and a plurality of cargo molecules. In some forms, the composition, AMT composition, co-composition, or cargo composition can comprise one or more surface molecules, a plurality of peptides and a plurality of cargo molecules. In some forms, the composition, AMT composition, co-composition, or cargo composition can comprise a plurality of surface molecules, one or more peptides and a plurality of cargo molecules. In some forms, the composition, AMT composition, co-composition, or cargo composition can comprise a plurality of surface molecules, a plurality of peptides and one or more cargo molecules. In some forms, the composition, AMT composition, co-composition, or cargo composition can comprise one or more surface molecules, one or more peptides and a plurality of cargo molecules. In some forms, the composition, AMT composition, co-composition, or cargo composition can comprise one or more surface molecules, a plurality of peptides and one or more cargo molecules. In some forms, the composition, AMT composition, co-composition, or cargo composition can comprise a plurality of surface molecules, one or more peptides and one or more cargo molecules.

In some forms, the composition, AMT composition, co-composition, or cargo composition can comprise a surface molecule, a plurality of peptides and a plurality of cargo molecules, wherein one or more of the peptides and one or more of the cargo molecules are associated with the surface molecule. In some forms, the composition, AMT composition, co-composition, or cargo composition can comprise a surface molecule, a plurality of peptides and a plurality of cargo molecules, wherein a plurality of the plurality of peptides and a plurality of the plurality of cargo molecules are associated with the surface molecule. In some forms, the composition, AMT composition, co-composition, or cargo composition can comprise a surface molecule, a plurality of peptides and a plurality of cargo molecules, wherein the peptides and the cargo molecules are associated with the surface molecule.

In some forms, the composition, AMT composition, co-composition, or cargo composition can comprise a surface molecule, wherein the surface molecule is multivalent for peptides and cargo molecules. In some forms, the composition, AMT composition, co-composition, or cargo composition can comprise a surface molecule, wherein the surface molecule is multivalent for peptides and comprises one or more cargo molecules. In some forms, the composition, AMT composition, co-composition, or cargo composition can comprise a surface molecule, wherein the surface molecule is multivalent for cargo molecules and comprises one or more peptides. In some forms, the composition, AMT composition, co-composition, or cargo composition can comprise a surface molecule, wherein the surface molecule is multivalent for conjugates, wherein one or more of the conjugates comprise one or more peptides and one or more cargo molecules. In some forms, the composition, AMT composition, co-composition, or cargo composition can comprise a surface molecule, wherein the surface molecule is multivalent for conjugates, wherein one or more of the conjugates comprise a plurality of peptides and a plurality of cargo molecules. In some forms, the composition, AMT composition, co-composition, or cargo composition can comprise a surface molecule, wherein the surface molecule is multivalent for conjugates, wherein one or more of the conjugates comprise a peptide and a cargo molecule. In some forms, the composition, AMT composition, co-composition, or cargo composition can comprise a surface molecule, wherein the surface molecule is multivalent for conjugates, wherein each of the conjugates comprises a plurality of peptides and a plurality of cargo molecules. In some forms, the composition, AMT composition, co-composition, or cargo composition can comprise a surface molecule, wherein the surface molecule is multivalent for conjugates, wherein each of the conjugates comprises a peptide and a cargo molecule.

In some forms, the composition, AMT composition, co-composition, or cargo composition can comprise a surface molecule, wherein the surface molecule comprises one or more conjugates, wherein one or more of the conjugates comprise one or more peptides and one or more cargo molecules. In some forms, the composition, AMT composition, co-composition, or cargo composition can comprise a surface molecule, wherein the surface molecule comprises one or more conjugates, wherein one or more of the conjugates comprise a plurality of peptides and a plurality of cargo molecules. In some forms, the composition, AMT composition, co-composition, or cargo composition can comprise a surface molecule, wherein the surface molecule comprises one or more conjugates, wherein one or more of the conjugates comprise a peptide and a cargo molecule. In some forms, the composition, AMT composition, co-composition, or cargo composition can comprise a surface molecule, wherein the surface molecule comprises one or more conjugates, wherein each of the conjugates comprises a plurality of peptides and a plurality cargo molecules. In some forms, the composition, AMT composition, co-composition, or cargo composition can comprise a surface molecule, wherein the surface molecule comprises one or more conjugates, wherein each of the conjugates comprises a peptide and a cargo molecule.

In some forms, the peptides can be conjugated with the surface molecule. In some forms, one or more of the conjugated peptides can be directly conjugated to the surface molecule. In some forms, one or more of the conjugated peptides can be indirectly conjugated to the surface molecule. In some forms, one or more of the peptides can be covalently coupled to the surface molecule. In some forms, one or more of the covalently coupled peptides can be directly covalently coupled to the surface molecule. In some forms, one or more of the covalently coupled peptides can be indirectly covalently coupled to the surface molecule.

Reference to components (such as an AMT peptide and a co-composition) as not being "indirectly conjugated" means that the indirectly conjugated components are directly conjugated another component or components that intervene between the indirectly conjugated components.

In some forms, the surface molecule can comprise a nanoparticle. In some forms, the surface molecule can comprise a nanoworm. In some forms, the surface molecule can comprise an iron oxide nanoworm. In some forms, the surface molecule can comprise an iron oxide nanoparticle. In some forms, the surface molecule can comprise an albumin nanoparticle. In some forms, the surface molecule can comprise a liposome. In some forms, the surface molecule can comprise a micelle. In some forms, the surface molecule comprises a phospholipid. In some forms, the surface molecule comprises a polymer. In some forms, the surface molecule can comprise a microparticle. In some forms, the surface molecule can comprise a fluorocarbon microbubble.

In some forms, the composition, AMT composition, co-composition, or cargo composition can comprise at least 100 AMT peptides. In some forms, the composition, AMT composition, co-composition, or cargo composition can comprise at least 1000 AMT peptides. In some forms, the composition, AMT composition, co-composition, or cargo composition can comprise at least 10,000 AMT peptides.

In some forms, the composition, AMT composition, co-composition, or cargo composition can comprise at least 100 membrane perturbing molecules. In some forms, the composition, AMT composition, co-composition, or cargo composition can comprise at least 1000 membrane perturbing molecules. In some forms, the composition, AMT composition, co-composition, or cargo composition can comprise at least 10,000 membrane perturbing molecules.

In some forms, one or more of the peptides can be modified peptides. In some forms, one or more of the peptides can comprise a methylated peptide. In some forms, one or more of the methylated peptides can comprise a methylated amino acid segment. In some forms, the amino acid segment can be N- or C-methylated in at least one position.

In some forms, the composition can further comprise one or more moieties. In some forms, the moieties can be independently selected from the group consisting of, for example, a pro-apototic agent, a pro-inflammatory agent, an immunostimulating agent, an anti-inflammatory agent, an immunosuppressing agent, an anti-angiogenic agent, a pro-angiogenic agent, a cancer chemotherapeutic agent, an antibacterial agent, a cytotoxic agent, a polypeptide, a nucleic acid molecule, a small molecule, an image contrast agent, a fluorophore, fluorescein, rhodamine, a radionuclide, indium-111, technetium-99, carbon-11, and carbon-13. In some forms, at least one of the moieties can be a therapeutic agent. In some forms, the therapeutic agent can be Abraxane. In some forms, the therapeutic agent can be paclitaxel. In some forms, the therapeutic agent can be taxol. In some forms, the therapeutic agent can be doxorubicin. In some forms, the therapeutic agent can be rapamycin. In some forms, at least one of the moieties can be a detectable agent. In some forms, the detectable agent can be FAM.

In some forms, one or more of the peptides can comprise the amino acid sequence RVLRSGS (SEQ ID NO:2), and one or more of the peptides can be indirectly conjugated to the surface molecule via a linker. In some forms, at least one of the linkers can comprise polyethylene glycol.

Also disclosed are methods of enhancing targeting, delivery, or both of a co-composition into or through a cell, tissue, or both. In some forms, the method can comprising exposing the cell, tissue, or both to the co-composition and an AMT composition, thereby enhancing targeting, delivery, or both of the co-composition into or through the cell, tissue, or both. The AMT composition can comprise any of the disclosed AMT peptides or any of the disclosed compositions that comprise an AMT peptide. In some forms, the AMT composition and the co-composition are not covalently coupled or directly non-covalently associated with each other prior to exposing the cell, tissue, or both.

Also disclosed are methods of enhancing targeting, delivery, or both of a cargo composition into or through a cell, tissue, or both. In some forms, the method can comprise exposing the cell, tissue, or both to the cargo composition and an AMT composition, thereby enhancing targeting, delivery, or both of the cargo composition into or through the cell, tissue, or both. The AMT composition can comprise any of the disclosed AMT peptides or any of the disclosed compositions that comprise an AMT peptide. In some forms, the AMT composition and the cargo composition can be covalently coupled or non-covalently associated with each other.

Also disclosed are methods of enhancing targeting, delivery, or both into or through a cell, tissue, or both. In some forms, the method can comprise exposing the cell, tissue, or both to an AMT composition, thereby enhancing targeting, delivery, or both into or through the cell, tissue, or both. The AMT composition can comprise any of the disclosed AMT peptides or any of the disclosed compositions that comprise an AMT peptide.

Also disclosed are methods of enhancing internalization, penetration, or both of a co-composition into or through a cell, tissue, or both. In some forms, the method can comprising exposing the cell, tissue, or both to the co-composition and an AMT composition where the AMT composition includes CendR element, thereby enhancing internalization, penetration, or both of the co-composition into or through the cell, tissue, or both. The AMT composition can comprise any of the disclosed AMT peptides or any of the disclosed compositions that comprise an AMT peptide. In some forms, the AMT composition and the co-composition are not covalently coupled or non-covalently associated with each other prior to exposing the cell, tissue, or both.

Also disclosed are methods of enhancing internalization, penetration, or both of a cargo composition into or through a cell, tissue, or both. In some forms, the method can comprise exposing the cell, tissue, or both to the cargo composition and an AMT composition where the AMT composition includes CendR element, thereby enhancing internalization, penetration, or both of the cargo composition into or through the cell, tissue, or both. The AMT composition can comprise any of the disclosed AMT peptides or any of the disclosed compositions that comprise an AMT peptide. In some forms, the AMT composition and the cargo composition can be covalently coupled or non-covalently associated with each other.

Also disclosed are methods of enhancing internalization, penetration, or both into or through a cell, tissue, or both. In some forms, the method can comprise exposing the cell, tissue, or both to an AMT composition where the AMT composition includes CendR element, thereby enhancing internalization, penetration, or both into or through the cell, tissue, or both. The AMT composition can comprise any of the disclosed AMT peptides or any of the disclosed compositions that comprise an AMT peptide.

In some forms, the cell, tissue, or both can be in a subject. In some forms, the cell, tissue, or both can be exposed to the AMT composition and the co-composition by administering the AMT composition and the co-composition to the subject. In some forms, the cell, tissue, or both can be exposed to the AMT composition and the cargo composition by administering the AMT composition and the cargo composition to the subject. In some forms, the cell, tissue, or both can be exposed to the AMT composition by administering the AMT composition to the subject.

In some forms, the AMT composition can selectively home to activated macrophages. In some forms, the AMT composition can selectively home to tumor associated macrophages. In some forms, the AMT composition and the co-composition can be administered to the subject simultaneously. In some forms, the AMT composition and the co-composition can be administered to the subject in a single composition comprising the AMT composition and the co-composition. In some forms, the AMT composition and the co-composition can be administered to the subject in separate compositions. In some forms, the AMT composition and the co-composition can be administered to the subject at different times. In some forms, the AMT composition and the co-composition can be administered to the subject in separate compositions. In some forms, the AMT composition and the co-composition can be administered to the subject by separate routes.

In some forms, the AMT composition and the co-composition are not bound to each other. In some forms, the AMT composition, co-composition, and/or cargo composition can comprise a therapeutic agent. In some forms, the AMT composition, co-composition, and/or cargo composition can comprise a detectable agent. In some forms, the AMT composition, co-composition, and/or cargo composition can comprise a carrier, vehicle, or both. In some forms, the AMT composition, co-composition, and/or cargo composition can comprise a therapeutic protein, a therapeutic compound, a therapeutic composition, a cancer chemotherapeutic agent, a toxin, a cytotoxic agent, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, a pro-apototic agent, a pro-inflammatory agent, an immunostimulating agent, an anti-inflammatory agent, an immunosuppressing agent, an anti-angiogenic agent, a pro-angiogenic agent, an anti-bacterial agent, or a combination.

In some forms, the AMT composition can comprise one or more accessory molecules. In some forms, the cell, tissue, or both can be exposed to a plurality of peptides. In some forms, the cell, tissue, or both can be exposed to a plurality of cargo compositions. In some forms, the cell, tissue, or both can be exposed to a plurality of AMT compositions. In some forms, the cell, tissue, or both can be exposed to a plurality of co-compositions.

In some forms, the AMT composition, co-composition, and/or cargo composition can have a therapeutic effect. In some forms, the therapeutic effect can be a slowing in the increase of or a reduction of tumor burden. In some forms, the therapeutic effect can be a slowing of the increase of or reduction of tumor size. In some forms, the subject can have one or more sites to be targeted, where the AMT composition, co-composition, and/or cargo composition homes to one or more of the sites to be targeted. In some forms, the subject can have activated macrophages, where the AMT composition, co-composition, and/or cargo composition has a therapeutic effect on the tumor.

The peptide can be an activatable peptide. The peptide can be a protease-activatable peptide. The protein or peptide can be circular (cyclic) or can contain a loop. The peptide can be at the C-terminal end of the protein or peptide. The peptide can comprise a terminal carboxyl group. A blocking group can be coupled to the terminal carboxyl group. The bond coupling the blocking group and the terminal carboxyl group can be selected to be cleavable by a protease, enzyme, cleaving agent, and/or cleaving conditions present in proximity to the cell of interest. The blocking group can be coupled to the C-terminal amino acid of the peptide. The blocking group can be coupled to an amino acid of the peptide other than the C-terminal amino acid of the peptide. The blocking group can comprise or consist of an amino acid or an amino acid sequence. Also disclosed are methods of producing an activatable peptide that can be activated in proximity to a cell of interest, the method comprising forming an activatable peptide wherein a blocking group is coupled to a peptide via a cleavable bond, wherein the cleavable bond is cleavable by an enzyme, cleaving agent, and/or cleaving conditions present in proximity to the cell of interest. Also disclosed are methods of producing an activatable peptide that can be activated in proximity to a cell of interest, the method comprising forming an activatable peptide wherein a blocking group is coupled to a peptide via a cleavable bond, wherein the cleavable bond is cleavable by an enzyme, cleaving agent, and/or cleaving conditions present in proximity to the cell of interest. The cell can be in a subject. The enzyme, cleaving agent, and/or cleaving conditions that is present in proximity to the cell of interest can be identified. The enzyme, cleaving agent, and/or cleaving conditions present in proximity to the cell of interest can be identified prior to forming the activatable peptide. The cleavable bond can be selected based on the enzyme that is present in proximity to the cell of interest. The cleavable bond can be selected based on the cleaving agent present at site where the peptide is delivered, homes, travels or accumulates, such as the cell of interest. The cleavable bond can be selected based on the cleaving conditions present at site where the peptide is delivered, homes, travels or accumulates, such as the cell of interest. The cleavable bond can be selected prior to forming the activatable peptide. The peptide can comprise a terminal carboxyl group, wherein the blocking group is coupled to the terminal carboxyl group. Also disclosed are methods of producing an activatable peptide, the method comprising forming an activatable peptide wherein a blocking group is coupled to a peptide via a cleavable bond. The cleavable bond can be cleaved in any suitable way. For example, the cleavable bond can be cleaved enzymatically or non-enzymatically. For enzymatic cleavage, the cleaving enzyme can be supplied or can be present at a site where the peptide is delivered, homes, travels or accumulates. For example, the enzyme can be present in proximity to a cell to which the peptide is delivered, homes, travels, or accumulates. For non-enzymatic cleavage, the peptide can be brought into contact with a cleaving agent, can be placed in cleaving conditions, or both. A cleaving agent is any substance that can mediate or stimulate cleavage of the cleavable bond. Cleaving conditions can be any solution or environmental conditions that can mediate or stimulate cleavage of the cleavable bond.

Also disclosed are methods of forming an activatable peptide, the method comprising causing a blocking group to be covalently coupled to a peptide, wherein a bond coupling the blocking group and the peptide is cleavable. Also disclosed are methods of forming an activatable peptide, the method comprising causing a blocking group to be covalently coupled to an amino acid sequence, wherein the amino acid sequence comprises a peptide the peptide, wherein a bond coupling the blocking group and the peptide is cleavable. Also disclosed are methods of forming an activatable peptide, the method comprising (a) selecting an amino acid sequence for internalization into a cell and/or penetration of tissue, wherein the amino acid sequence comprises a peptide, and (b) causing a blocking group to be covalently coupled to the peptide, wherein a bond coupling the blocking group and the peptide is cleavable. The blocking group covalently coupled to the peptide reduces or prevents internalization into a cell and/or penetration of tissue. The blocking group covalently coupled to the peptide can reduce or prevent internalization into a cell and/or penetration of tissue compared to the same peptide with no blocking group. For example, an amino acid sequence comprising AMT sequence-cleavage site-homing module can be made and then tested for activatability (via cleavage of the cleavage site, for example). For example, a pool of peptides having the amino acid sequence RVLRS-XXXXXXXXXXXXXXXX (SEQ ID NO:19) can be tested for homing and activatability. That is, such peptides can be identified by screens using libraries. The activatable peptide can comprise the selected amino acid sequence and the blocking group. The cell can be in a subject. The enzyme, cleaving agent, and/or cleaving conditions present in proximity to the cell of interest can be identified. The enzyme, cleaving agent, and/or cleaving conditions present in proximity to the cell of interest can be identified prior to forming the activatable peptide. The cleavable bond can be selected based on the enzyme that is present in proximity to the cell of interest. The cleavable bond can be selected based on the cleaving agent present at site where the peptide is delivered, homes, travels or accumulates, such as the cell of interest. The cleavable bond can be selected based on the cleaving conditions present at site where the peptide is delivered, homes, travels or accumulates, such as the cell of interest. The cleavable bond can be selected prior to forming the activatable peptide. The peptide can comprise a terminal carboxyl group, wherein the blocking group is coupled to the terminal carboxyl group.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 2 is a graph of relative FAM-CFV binding to J774A.1 cells. FAM-CRV was mixed with PBS or biotin-CRV (50-fold excess). Error bars, SEM. **$P<0.01$ (Student's t-test).

DETAILED DESCRIPTION OF THE INVENTION

Figure 1A:
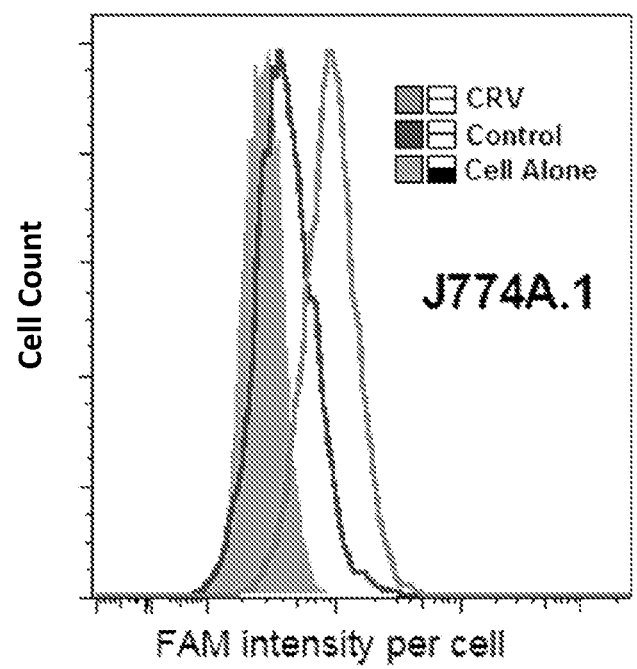
FIGS. 1A and 1B are graphs showing the binding of FAM-CRV and a FAM-labeled control peptide, ARA (J774A.1 cells; 1A) or GGSGGSKG (SEQ ID NO:9) (Raw264.7 cells; 1B) to the indicated cells. At least three independent experiments were carried out, and representative results are shown.

The disclosed method and compositions can be understood more readily by reference to the following detailed description of particular embodiments and the Examples included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

As used herein, the terms "including", "includes", "having", "has", "with", or variants thereof, are intended to be inclusive similar to the term "comprising."

The term "inhibit" means to reduce or decrease in activity or expression. This can be a complete inhibition of activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

B. General

Disclosed herein are peptides that enable targeting and delivery of compositions to activated macrophages. Targeting and delivery of compositions (including nanoparticles, drugs, detectable markers, and other compounds) and their payload into target cells can increase the effectiveness of the payload.

Targeted delivery of therapeutic or diagnostic agents to activated macrophages, such as tumor associated macrophages, can be used for more effective treatment of diseases and conditions involving activated macrophages.

Peptides that bind to activated macrophages, such as tumor associated macrophages (TAMs), in a cell type-specific and tissue-specific manner were identified using in vitro phage display on a mouse monocyte/macrophage cell line. The study lead to the discovery of a peptide with such properties, termed CRV (CRVLRSGSC; SEQ ID NO:1). The two terminal cysteines form a disulfide bond to render the peptide cyclic. CRV binds to monocyte/macrophage cell lines in vitro, and selectively homes to tumors in vivo, binding to tumor-associated macrophages.

The disclosed peptides can be used for targeted drug delivery system for tumor-associated macrophages, which are an important group of immunosuppressive cells in solid tumors. Modulation of TAM function can be used, for example, to enhance the clinical efficacy of anticancer drugs, especially such drugs that involve immunotherapy. The disclosed peptides can also be combined with imaging agents to detect TAMs.

The disclosed peptides can have two properties that are particularly useful: (1) selective binding to macrophages residing in tumors, but not in normal organs, and (2) affinity to tumor macrophages, but not macrophages in other pathological tissues, such as atherosclerosis plaques. One or both of these properties enhances the ability to target, and usefulness of targeting, macrophages in a disease-specific manner.

It has also been demonstrated that the CRV peptide targets and activates macrophages in sites of infection, such as microbial, viral, or bacterial infection. The result was markedly increased ability of the host to clear the infection. Thus, the disclosed peptides can be used to target macrophages in sites of infection, such as microbial, viral, or bacterial infection.

Other TAM-recognizing peptides were previously discovered, such as LyP-1 and TT1. The sequence and specificity profile of the disclosed CRV and AMT peptides are different from the other peptides.

Macrophages have long been considered to be important immune effector cells but also have vital homeostatic roles, which are independent of their involvement in immune responses. Macrophages are prodigious phagocytic cells that clear approximately $2 \times 10^{11}$ erythrocytes each day; this equates to almost 3 kg of iron and hemoglobin per year that is 'recycled' for the host to reuse. This clearance process is a vital metabolic contribution without which the host would not survive. Macrophages are also involved in the removal of cellular debris that is generated during tissue remodeling, and rapidly and efficiently clear cells that have undergone apoptosis. These processes occur independently of immune-cell signaling, and the removal of 'effete' or apoptotic cells seems to result in little or no production of immune mediators by unstimulated macrophages. The receptors that mediate these homeostatic clearance processes include scavenger receptors, phosphatidyl serine receptors, the thrombospondin receptor, integrins and complement receptors. In general, these receptors that mediate phagocytosis either fail to transduce signals that induce cytokine-gene transcription or actively produce inhibitory signals and/or cytokines, and most of the phagocytosis that occurs on a daily basis by macrophages is independent of other immune cells. Therefore, the primary role of macrophages is not to function as elite immune effector cell, but instead as a common 'janitorial' cell, the main function of which is to clear the interstitial environment of extraneous cellular material.

Necrosis that results from trauma or stress also generates cellular debris that must be cleared by macrophages. In contrast to the examples cited above, the clearance of this debris markedly alters the physiology of macrophages. In many cases the debris from necrosis is loaded with endogenous danger signals, such as heat-shock proteins, nuclear proteins (including HMGB1; high-mobility group protein), histones, DNA and other nucleotides, and components of the extracellular matrix that are cleaved by cellular proteases. Phagocytosis of these components by macrophages leads to dramatic changes in their physiology, including alterations in the expression of surface proteins and the production of cytokines and pro-inflammatory mediators. The alterations in macrophage surface-protein expression in response to these stimuli could potentially be used to identify biochemical markers that are unique to these altered cells.

Macrophages can be activated by cytokines such as interferon-gamma (IFN-gamma) and bacterial endotoxins, such as lipopolysaccharide (LPS). Activated macrophages undergo many changes which allow them to kill invading bacteria or infected cells. They release toxic chemicals and proteins which have toxic effects on other cells.

Activated macrophages are products of a cell-mediated immune response. They can also be transiently generated in response to innate stimuli following stress or viral infections. Some pathogens have developed the ability to interfere with IFNγ signaling and prevent efficient macrophage activation. These classically activated macrophages are vital components of host defense, but their activation must be tightly controlled because the cytokines and mediators that they produce can lead to host-tissue damage. Indeed, classically activated macrophages are key mediators of the immunopathology that occurs during several autoimmune diseases, including rheumatoid arthritis and inflammatory bowel disease.

Activated macrophages are larger, have increased metabolism, increased levels of lysosomal proteins, and a greater ability to phagocytosis and kill microbes. Activated macrophages also release proteases, neutrophil chemotatic factors; reactive oxygen species such as nitric oxide and superoxide; cytokines such as tumor necrosis factor-alpha (TNF-alpha), interleukin one and eight (IL-1 and IL-8), eicosanoids, as well as growth factors. These products of activated macrophages result in the tissue destruction which is a hallmark of inflammation. In some cases (such as cancer), an increase in tissue destruction (i.e., destruction of tumors) is desirable. In these cases, stimulation of an immune response is desirable. In the case of activated macrophages, this can be by, for example, inhibiting M1 macrophages or one or more immune suppressing effects of M1 macrophages, stimulating M2 macrophages or one or more immunostimulatory effects of M2 macrophages, or a combination of any of these. In other cases (such as infections that cause too great an immune reaction), an decrease in immune response is desirable. In the case of activated macrophages, this can be by, for example, stimulating M1 macrophages or one or more immune suppressing effects of M1 macrophages, inhibiting M2 macrophages or one or more immunostimulatory effects of M2 macrophages, or a combination of any of these.

Disclosed are peptides, conjugates, compositions and methods useful for targeting activated macrophages, such as tumor associated macrophages. In particular, disclosed are isolated peptides comprising an activated macrophage targeting (AMT) amino acid sequence. In some forms, the AMT amino acid sequence comprises or consists of RVLRSGS (SEQ ID NO:2). In some forms, the peptide selectively binds to activated macrophages via the AMT amino acid sequence. Generally, an AMT amino acid sequence binds to a receptor on the surface of activated macrophages. As a consequence, a peptide that selectively binds to activated macrophages via the AMT amino acid sequence will be structured to have the AMT amino acid sequence exposed and available for binding to the receptor on the surface of activated macrophages.

In some forms, the peptide comprises the sequence CRVLRSGSC (SEQ ID NO:1). In some forms, the peptide is cyclic. In some forms, the peptide is a modified peptide. In some forms, the peptide is a methylated peptide. In some forms, the methylated peptide comprises a methylated amino acid segment. In some forms, the peptide is N- or C-methylated in at least one position.

Also disclosed are compositions comprising one or more of the disclosed peptides. In some forms, the composition further comprises a co-composition, wherein the peptide and the co-composition are not covalently coupled or directly non-covalently associated with each other. In some forms, the composition further comprises a cargo composition, wherein the peptide and the cargo composition are covalently coupled or non-covalently associated with each other.

In some forms, the peptide selectively homes to activated macrophages. In some forms, the peptide selectively homes to tumor associated macrophages. In some forms, the co-composition or cargo composition comprises a therapeutic agent. In some forms, the co-composition or cargo composition comprises a detectable agent. In some forms, the co-composition or cargo composition comprises a carrier, vehicle, or both.

In some forms, the co-composition or cargo composition comprises a therapeutic protein, a therapeutic compound, a therapeutic composition, a cancer chemotherapeutic agent, a toxin, a cytotoxic agent, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, a pro-apototic agent, a pro-inflammatory agent, an immunostimulating agent, an anti-inflammatory agent, an immunosuppressing agent, an anti-angiogenic agent, an anti-bacterial agent, or a combination.

In some forms, the peptide is comprised in an AMT composition. In some forms, the AMT composition comprises one or more cargo compositions. In some forms, the AMT composition further comprises one or more copies of the peptide. In some forms, the peptide is comprised in an AMT conjugate. In some forms, the AMT conjugate comprises one or more cargo compositions. In some forms, the AMT conjugate comprises one or more copies of the peptide.

In some forms, the composition comprises a plurality of cargo compositions. In some forms, the composition comprises a plurality of copies of the peptide. In some forms, the composition comprises a plurality of co-compositions.

In some forms, the composition further comprises a surface molecule. In some forms, the peptide is conjugated with the surface molecule. In some forms, one or more of the conjugated peptides is indirectly conjugated to the surface molecule via a linker. In some forms, the composition further comprises a plurality of linkers. In some forms, at least one of the linkers comprises polyethylene glycol.

In some forms, the composition binds activated macrophages. In some forms, the composition is internalized in cells. In some forms, the composition reduces an inflammatory response. In some forms, the composition increases an inflammatory response. In some forms, the composition promotes apoptosis. In some forms, the composition reduces growth or proliferation of an infectious agent. In some forms, the composition reduces tumor growth.

In some forms, the surface molecule comprises a nanoparticle, a nanoworm, an iron oxide nanoworm, an iron oxide nanoparticle, an albumin nanoparticle, a liposome, a micelle, a phospholipid, a polymer, a microparticle, or a fluorocarbon microbubble.

In some forms, the composition further comprises one or more copies of the peptide. In some forms, the composition comprises at least 100 copies of the peptide. In some forms, the composition comprises at least 1000 copies of the peptide.

In some forms, the composition further comprises one or more moieties. In some forms, the moieties are independently selected from the group consisting of a pro-apototic agent, a pro-inflammatory agent, an immunostimulating agent, an anti-inflammatory agent, an immunosuppressing agent, an anti-angiogenic agent, a pro-angiogenic agent, a cancer chemotherapeutic agent, an anti-bacterial agent, a cytotoxic agent, a polypeptide, a nucleic acid molecule, a small molecule, an image contrast agent, a fluorophore, fluorescein, rhodamine, a radionuclide, indium-111, technetium-99, carbon-11, and carbon-13.

In some forms, at least one of the moieties is a therapeutic agent. In some forms, the therapeutic agent is an anti-cancer agent. In some forms, the therapeutic agent inhibits expression of the phosphotidylinositide 3-kinase (PI3K) gamma gene. In some forms, the therapeutic agent inhibits PI3K gamma. In some forms, the therapeutic agent can be a PI3K gamma inhibitor (such as TG100-115), and TNF-alpha. In some forms, at least one of the moieties is a detectable agent. In some forms, the detectable agent is FAM.

In some forms, the composition further comprises one or more copies of the peptide and, wherein the peptides are conjugated to the liposome, wherein the peptides each comprise the sequence CRVLRSGSC (SEQ ID NO:1), wherein the peptides are cyclic.

Also disclosed are method of using the disclosed peptides, conjugates, and compositions. In some forms, the method comprises exposing activated macrophages to a disclosed composition, wherein the composition selectively binds to the activated macrophages. In some forms, the activated macrophages are in a subject. In some forms, the activated macrophages are exposed to the composition by administering the composition to the subject.

In some forms, the composition has a therapeutic effect. In some forms, the therapeutic effect comprises a reduction in inflammation, an increase in inflammation, an increase in apoptosis, a reduction in growth or proliferation of an infectious agent, an increase in speed of wound healing, reduction in amounts of scar tissue, decrease in pain, decrease in swelling, or decrease in necrosis. In some forms, the therapeutic effect comprises decrease in inflammatory immune response. In some forms, the composition increases an inflammatory response. In some forms, the composition promotes apoptosis. In some forms, the composition reduces growth or proliferation of an infectious agent. In some forms, the subject has a disease or condition. In some forms, the disease is cancer. In some forms, the disease is microbial infection. In some forms, the disease is atherosclerosis.

In some forms, the composition selectively homes to activated macrophages. In some forms, the composition selectively homes to tumor associated macrophages.

Various compositions can be internalized through the CendR mechanism. The CendR pathway can also be used for exit of compositions of interest from the vasculature and their spread into tissue. The C-terminal element can cause spread of compositions from the vasculature (and thus can be spread into tumor tissue from an intravenous injection, for example). CendR elements can also be used to mediate passage of compositions of interest through other CendR-capable membranes, such as mucous membranes and the blood-brain barrier. As used herein, "tissue penetration" and "penetration of tissue" refer to passage into or through a tissue beyond or through the outer or a first layer of cells or through a tissue membrane. Such passage or penetration through tissue (which can also be referred to as extravasation and tissue penetration) can be a function of, for example, cell internalization and passage between cells in the tissue. Throughout this application, when the term "tissue penetration" is used, it is understood that such penetration can also extend to other barriers and CendR-capable membranes found throughout the body, such as the blood brain barrier.

In the case of the disclosed AMT peptides, the peptides can provide both homing to activated macrophages and cell internalization and tissue penetration at the site of accumulation. Unlike the known cell-penetrating peptides, CendR element function is position-dependent—it is inactive when present in positions other than the C-terminus of the peptide.

Disclosed are AMT compositions, AMT conjugates, AMT molecules, AMT proteins, and AMT peptides. AMT peptides are the basic feature of AMT compositions, AMT conjugates, AMT molecules, AMT proteins, and the like. AMT compositions are any composition, conglomeration, conjugate, molecule, protein, peptide, etc. that comprises an AMT peptide. AMT conjugates are associations, whether covalent or non-covalent, of an AMT peptide and one or more other elements, peptides, proteins, compounds, molecules, agents, compounds, etc. For example, an AMT conjugate can comprise an AMT peptide, AMT protein, AMT compound, AMT molecule, etc. AMT molecules are molecules that comprise an AMT peptide. For example, an AMT molecule can comprise an AMT protein, AMT peptide, etc. In general, AMT peptides, AMT proteins, AMT molecules, and AMT conjugates are all forms of AMT compositions. AMT compounds, AMT peptides and AMT proteins can be forms of AMT molecules. Unless the context indicates otherwise, reference to an AMT composition is intended to refer to AMT compositions, AMT molecules, AMT proteins, AMT peptides, and the like. An AMT component is any molecule, peptide, protein, compound, conjugate, composition, etc. that comprises an AMT peptide. Examples of AMT components include, for example, AMT compositions, AMT molecules, AMT proteins, and AMT peptides.

AMT components can comprise one or more AMT peptides. Where an AMT element comprises two or more AMT peptides, it is useful for the AMT component to be designed to allow some or all of the AMT peptides to be exposed at the C-terminus of a protein or peptide. This can be accomplished in numerous ways in, for example, conjugates and compositions. This can also be accomplished in, for example, branching peptides and proteins.

Disclosed are CRV compositions, CRV conjugates, CRV molecules, CRV proteins, and CRV peptides. CRV peptides are the basic feature of CRV compositions, CRV conjugates, CRV molecules, CRV proteins, and the like. CRV compositions are any composition, conglomeration, conjugate, molecule, protein, peptide, etc. that comprises a CRV peptide. CRV conjugates are associations, whether covalent or non-covalent, of a CRV peptide and one or more other elements, peptides, proteins, compounds, molecules, agents, compounds, etc. For example, a CRV conjugate can comprise a CRV peptide, CRV protein, CRV compound, CRV molecule, etc. CRV molecules are molecules that comprise a CRV peptide. For example, a CRV molecule can comprise a CRV protein, CRV peptide, etc. In general, CRV peptides, CRV proteins, CRV molecules, and CRV conjugates are all forms of CRV compositions. CRV compounds, CRV peptides and CRV proteins can be forms of CRV molecules. Unless the context indicates otherwise, reference to a CRV composition is intended to refer to CRV compositions, CRV molecules, CRV proteins, CRV peptides, and the like. A CRV component is any molecule, peptide, protein, compound, conjugate, composition, etc. that comprises a CRV peptide. Examples of CRV components include, for example, CRV compositions, CRV molecules, CRV proteins, and CRV peptides.

CRV components can comprise one or more CRV peptides. Where a CRV element comprises two or more CRV peptides, it is useful for the CRV component to be designed to allow some or all of the CRV peptides to be exposed at the C-terminus of a protein or peptide. This can be accomplished in numerous ways in, for example, conjugates and compositions. This can also be accomplished in, for example, branching peptides and proteins.

Disclosed are peptides that target tumor associated macrophages. The disclosed peptides can also mediate targeting and delivery of compounds and compositions coupled to, associated with, conjugated to, or even co-administered with the peptide. The disclosed peptides generally can have the sequence $X_1$—R—$X_2$-L-R—S—$X_3$. $X_1$ and $X_3$ can each be, independently, zero to four amino acids, where the amino acids of $X_1$ and $X_3$ can be any amino acid. $X_2$ can be one or two amino acids, and where the amino acids of $X_2$ can be any amino acid.

In some forms, $X_1$ can be zero, one, two, or three amino acids. In some forms $X_1$ can be absent or any one amino acid chosen from C, G, or S. In some forms $X_1$ can be absent or any two amino acids independently chosen from C, G, or S. In some forms $X_1$ can be absent or any three amino acids independently chosen from C, G, or S. In some forms $X_1$ can be absent, C, or C followed by one amino acid chosen from G or S. In some forms $X_1$ can be absent, C, or C followed by any two amino acids independently chosen from G or S. In some forms $X_1$ can be absent or any one amino acid chosen from G or S. In some forms $X_1$ can be absent or any two amino acids independently chosen from G or S. In some forms $X_1$ can be absent or any three amino acids independently chosen from G or S.

In some forms $X_1$ can be absent, C, CG, CGG, CS, CGS, CSG, CSS, CSC, CGC, S, G, SG, GS, SS, GG, CC, CCC, SC, or GC. In some forms $X_1$ can be absent, C, CG, CGG, CS, CGS, CSG, CSS, CSC, CGC, S, G, SG, GS, SS, GG, CC, or CCC. In some forms $X_1$ can be absent, C, CG, CGG, CS, CGS, CSG, CSS, CSC, CGC, S, G, SG, GS, SS, or GG. In some forms $X_1$ can be absent, C, CG, CGG, CS, CGS, CSG, CSS, CSC, CGC, S, G, SG, or GS. In some forms $X_1$ can be absent, C, CG, CGG, CS, CGS, CSG, CSS, CSC, CGC, S, or G. In some forms $X_1$ can be absent, C, CG, CGG, CS, CGS, CSG, or CSS. In some forms $X_1$ can be absent, C, CG, CGG, CS, or CGS. In some forms $X_1$ can be absent, C, CG, or CGG.

In some forms, $X_3$ can be zero, one, two, or three amino acids. In some forms $X_3$ can be absent or any one amino acid chosen from C, G, or S. In some forms $X_3$ can be absent or any two amino acids independently chosen from C, G, or S. In some forms $X_3$ can be absent or any three amino acids independently chosen from C, G, or S. In some forms $X_3$ can be absent, C, or C following one amino acid chosen from G or S. In some forms $X_3$ can be absent, C, or C following any two amino acids independently chosen from G or S. In some forms $X_3$ can be absent or any one amino acid chosen from G or S. In some forms $X_3$ can be absent or any two amino acids independently chosen from G or S. In some forms $X_3$ can be absent or any three amino acids independently chosen from G or S.

In some forms $X_3$ can be absent, SC, GC, GSC, C, SGC, SSC, GGC, S, G, SG, GS, SS, GG, CC, CCC, CS, or CG. In some forms $X_3$ can be absent, SC, GC, GSC, C, SGC, SSC, GGC, S, G, SG, GS, SS, GG, CC, or CCC. In some forms $X_3$ can be absent, SC, GC, GSC, C, SGC, SSC, GGC, S, G, SG, GS, SS, or GG. In some forms $X_3$ can be absent, SC, GC, GSC, C, SGC, SSC, GGC, S, G, SG, or GS. In some forms $X_3$ can be absent, SC, GC, GSC, C, SGC, SSC, GGC, S, or G. In some forms $X_3$ can be absent, SC, GC, GSC, C, or SGC. In some forms $X_3$ can be absent, SC, GC, or GSC.

In some forms, $X_2$ can be one or two amino acids. In some forms $X_2$ can be any one amino acid chosen from V, L, M, S, I, G, A, T, C, or P. In some forms $X_3$ can be or any two amino acids independently chosen from V, L, M, S, I, G, A, T, C, or P. In some forms $X_3$ can be S or S followed by one amino acid chosen from V, L, M, I, G, A, T, C, or P. In some forms $X_3$ can be any one amino acid chosen from V, L, M. In some forms $X_3$ can be absent or any two amino acids independently chosen from V, L, M, S, I, G, A, or T. In some forms $X_3$ can be absent or any two amino acids independently chosen from V, L, M, S, I, or G. In some forms $X_3$ can be absent or any two amino acids independently chosen from V, L, M, or S.

In some forms $X_2$ can be V, L, M, SG, S, I, G, A, T, C, P, VG, LG, MG, IG, GG, AG, TG, CG, or PG. In some forms $X_2$ can be V, L, M, SG, S, I, G, A, T, C, P, VG, LG, MG, IG, GG, AG, or TG. In some forms $X_2$ can be V, L, M, SG, S, I, G, A, T, C, P, VG, LG, MG, IG, or GG. In some forms $X_2$ can be V, L, M, SG, S, I, G, A, T, C, P, VG, LG, or MG. In some forms $X_2$ can be V, L, M, SG, S, I, G, A, T, C, P, VG. In some forms $X_2$ can be V, L, M, SG, S, I, G, A, T, or C. In some forms $X_2$ can be V, L, M, SG, S, I, G, or A. In some forms $X_2$ can be V, L, M, SG, S, or I. In some forms $X_2$ can be V, L, M, or SG.

The various sequences and various sets of sequences disclosed for $X_1$, $X_2$, or $X_3$ can be used in an AMT peptide in any combination with the various sequences and various sets of sequences disclosed for the other two of $X_1$, $X_2$, and $X_3$.

Examples of the disclosed peptides include the amino acid sequence CRVLRSGSC (SEQ ID NO:1) or the amino acid sequence RVLRSGS (SEQ ID NO:2) and peptides consisting of CRVLRSGSC (SEQ ID NO:1) or RVLRSGS (SEQ ID NO:2). The disclosed peptides can be used in and with a variety of compositions and methods to, for example, mediate targeting and delivery of such compositions to activated macrophages. Such compositions and methods are also disclosed herein.

Disclosed are peptides where the peptide comprises the amino acid sequence RVLRSGS (SEQ ID NO:2). The amino acid sequence RVLRSGS (SEQ ID NO:2) is referred to herein as the AMT amino acid sequence. The AMT amino acid sequence consists of the amino acid sequence RVLRSGS (SEQ ID NO:2). Peptides that include, comprise, or consist of the amino acid sequence RVLRSGS (SEQ ID NO:2) can be referred to as AMT peptides. The amino acid sequence RVLRSGS (SEQ ID NO:2) is comprised in an AMT peptide.

A special form of AMT peptide is a CRV peptide. A CRV peptide has, includes, comprises, or consists of the amino acid sequence CRVLRSGSC (SEQ ID NO:1). The amino acid sequence CRVLRSGSC (SEQ ID NO:1) is referred to herein as the CRV amino acid sequence. The CRV amino acid sequence consists of the amino acid sequence CRVLRSGSC (SEQ ID NO:1). Peptides that include, comprise, or consist of the amino acid sequence CRVLRSGSC (SEQ ID NO:1) can be referred to as CRV peptides. The amino acid sequence CRVLRSGSC (SEQ ID NO:1) is comprised in a CRV peptide.

Because of the relationship between the AMT amino acid sequence and the CRV amino acid sequence, CRV compositions, CRV conjugates, CRV molecules, CRV proteins, and CRV peptides. CRV peptides are the basic feature of CRV compositions, CRV conjugates, CRV molecules, CRV proteins, and the like are all also AMT compositions, AMT conjugates, AMT molecules, AMT proteins, and AMT peptides. AMT peptides are the basic feature of AMT compositions, AMT conjugates, AMT molecules, AMT proteins, and the like, respectively.

In some forms, the peptide can be a modified peptide. In some forms, the peptide can be a methylated peptide. In some forms, one or more of the methylated peptide can comprise a methylated amino acid segment. In some forms, the peptide can be N- or C-methylated in at least one position.

AMT peptides are peptides comprising the amino acid sequence RVLRSGS (SEQ ID NO:2). AMT peptides can be composed of standard amino acids with standard peptide linkages or can be embodied in other than standard amino acids and/or with other than standard peptide linkages. AMT peptides can include modifications to the peptide, amino acids, and/or linkages. Examples of suitable modifications known to those in the art and are described elsewhere herein.

Disclosed are compositions comprising the disclosed AMT peptide. In some forms, the composition can further comprise a co-composition, where the peptide and the co-composition are not covalently coupled or directly non-covalently associated with each other. In some forms, the composition can further comprise a cargo composition, where the peptide and the cargo composition are covalently coupled or non-covalently associated with each other.

In some forms, the peptide can selectively home to activated macrophages. In some forms, the peptide can selectively home to tumor associated macrophages. In some forms, the peptide and the co-composition are not bound to each other. In some forms, the co-composition and/or cargo composition can comprise a therapeutic agent. In some forms, the co-composition and/or cargo composition can comprise a detectable agent. In some forms, the co-composition and/or cargo composition can comprise a carrier, vehicle, or both. In some forms, the co-composition and/or cargo composition can comprise a therapeutic protein, a therapeutic compound, a therapeutic composition, a cancer chemotherapeutic agent, a toxin, a cytotoxic agent, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, a pro-apototic agent, a pro-inflammatory agent, an immunostimulating agent, an anti-inflammatory agent, an immunosuppressing agent, an anti-angiogenic agent, an anti-bacterial agent, or a combination.

In some forms, the peptide can be comprised in an AMT composition. In some forms, the AMT composition can comprise one or more cargo compositions. In some forms, the AMT composition can comprise one or more peptides. In some forms, the peptide can be comprised in an AMT conjugate. In some forms, the AMT conjugate can comprise one or more cargo compositions. In some forms, the AMT conjugate can comprise one or more peptides. In some forms, the composition can comprise a plurality of cargo compositions. In some forms, the composition can comprise a plurality of copies of the peptide. In some forms, the composition can comprise a plurality of co-compositions.

In some forms, the composition can further comprise one or more peptides, wherein the peptides selectively home to tumor associated macrophages.

In some forms, one or more of the peptides can comprise the amino acid sequence RVLRSGS (SEQ ID NO:2) or a conservative derivative thereof. In some forms, one or more of the peptides can comprise the amino acid sequence RVLRSGS (SEQ ID NO:2) or a conservative variant thereof. In some forms. In some forms, all of the one or more peptides can comprise the amino acid sequence RVLRSGS (SEQ ID NO:2) or a conservative derivative thereof.

In some forms, one or more of the conjugated peptides can be indirectly conjugated to the surface molecule via a linker. In some forms, the composition can further comprise a plurality of linkers. In some forms, at least one of the linkers can comprise polyethylene glycol.

In some forms, the composition can bind inside tumor blood vessels. In some forms, the composition can be internalized in cells. In some forms, the composition can reduce tumor growth.

In some forms, the surface molecule can comprise a nanoparticle, a nanoworm, an iron oxide nanoworm, an iron oxide nanoparticle, an albumin nanoparticle, a liposome, a micelle, a phospholipid, a polymer, a microparticle, or a fluorocarbon microbubble. In some forms, the composition can comprise at least 100 copies of the peptide. In some forms, the composition can comprise at least 1000 copies of the peptide. In some forms, the composition can comprise at least 10,000 copies of the peptide.

In some forms, the composition, AMT composition, co-composition, or cargo composition can comprise a plurality of surface molecules, a plurality of peptides and a plurality of cargo molecules. In some forms, the composition, AMT composition, co-composition, or cargo composition can comprise one or more surface molecules, a plurality of peptides and a plurality of cargo molecules. In some forms, the composition, AMT composition, co-composition, or cargo composition can comprise a plurality of surface molecules, one or more peptides and a plurality of cargo molecules. In some forms, the composition, AMT composition, co-composition, or cargo composition can comprise a plurality of surface molecules, a plurality of peptides and one or more cargo molecules. In some forms, the composition, AMT composition, co-composition, or cargo composition can comprise one or more surface molecules, one or more peptides and a plurality of cargo molecules. In some forms, the composition, AMT composition, co-composition, or cargo composition can comprise one or more surface molecules, a plurality of peptides and one or more cargo molecules. In some forms, the composition, AMT composition, co-composition, or cargo composition can comprise a plurality of surface molecules, one or more peptides and one or more cargo molecules.

In some forms, the composition, AMT composition, co-composition, or cargo composition can comprise a surface molecule, a plurality of peptides and a plurality of cargo molecules, wherein one or more of the peptides and one or more of the cargo molecules are associated with the surface molecule. In some forms, the composition, AMT composition, co-composition, or cargo composition can comprise a surface molecule, a plurality of peptides and a plurality of cargo molecules, wherein a plurality of the plurality of peptides and a plurality of the plurality of cargo molecules are associated with the surface molecule. In some forms, the composition, AMT composition, co-composition, or cargo composition can comprise a surface molecule, a plurality of peptides and a plurality of cargo molecules, wherein the peptides and the cargo molecules are associated with the surface molecule.

In some forms, the composition, AMT composition, co-composition, or cargo composition can comprise a surface molecule, wherein the surface molecule is multivalent for peptides and cargo molecules. In some forms, the composition, AMT composition, co-composition, or cargo composition can comprise a surface molecule, wherein the surface molecule is multivalent for peptides and comprises one or more cargo molecules. In some forms, the composition, AMT composition, co-composition, or cargo composition can comprise a surface molecule, wherein the surface molecule is multivalent for cargo molecules and comprises one or more peptides. In some forms, the composition, AMT composition, co-composition, or cargo composition can comprise a surface molecule, wherein the surface molecule is multivalent for conjugates, wherein one or more of the conjugates comprise one or more peptides and one or more cargo molecules. In some forms, the composition, AMT composition, co-composition, or cargo composition can comprise a surface molecule, wherein the surface molecule is multivalent for conjugates, wherein one or more of the conjugates comprise a plurality of peptides and a plurality of cargo molecules. In some forms, the composition, AMT composition, co-composition, or cargo composition can comprise a surface molecule, wherein the surface molecule is multivalent for conjugates, wherein one or more of the conjugates comprise a peptide and a cargo molecule. In some forms, the composition, AMT composition, co-composition, or cargo composition can comprise a surface molecule, wherein the surface molecule is multivalent for conjugates, wherein each of the conjugates comprises a plurality of peptides and a plurality of cargo molecules. In some forms, the composition, AMT composition, co-composition, or cargo composition can comprise a surface molecule, wherein the surface molecule is multivalent for conjugates, wherein each of the conjugates comprises a peptide and a cargo molecule. As used herein, a component that is stated to be "multivalent for" one or more other components refers to a component that has a plurality of the other components associated with, conjugated to and/or covalent coupled to the first component.

In some forms, the composition, AMT composition, co-composition, or cargo composition can comprise a surface molecule, wherein the surface molecule comprises one or more conjugates, wherein one or more of the conjugates comprise one or more peptides and one or more cargo molecules. In some forms, the composition, AMT composition, co-composition, or cargo composition can comprise a surface molecule, wherein the surface molecule comprises one or more conjugates, wherein one or more of the conjugates comprise a plurality of peptides and a plurality of cargo molecules. In some forms, the composition, AMT composition, co-composition, or cargo composition can comprise a surface molecule, wherein the surface molecule comprises one or more conjugates, wherein one or more of the conjugates comprise a peptide and a cargo molecule. In some forms, the composition, AMT composition, co-composition, or cargo composition can comprise a surface molecule, wherein the surface molecule comprises one or more conjugates, wherein each of the conjugates comprises a plurality of peptides and a plurality cargo molecules. In some forms, the composition, AMT composition, co-composition, or cargo composition can comprise a surface molecule, wherein the surface molecule comprises one or more conjugates, wherein each of the conjugates comprises a peptide and a cargo molecule.

In some forms, the peptides can be conjugated with the surface molecule. In some forms, one or more of the conjugated peptides can be directly conjugated to the surface molecule. In some forms, one or more of the conjugated peptides can be indirectly conjugated to the surface molecule. In some forms, one or more of the peptides can be covalently coupled to the surface molecule. In some forms, one or more of the covalently coupled peptides can be directly covalently coupled to the surface molecule. In some forms, one or more of the covalently coupled peptides can be indirectly covalently coupled to the surface molecule.

In some forms, the surface molecule can comprise a liposome. In some forms, the surface molecule can comprise a nanoparticle. In some forms, the surface molecule can comprise a nanoworm. In some forms, the surface molecule can comprise an iron oxide nanoworm. In some forms, the surface molecule can comprise an iron oxide nanoparticle. In some forms, the surface molecule can comprise an albumin nanoparticle. In some forms, the surface molecule can comprise a micelle. In some forms, the surface molecule comprises a phospholipid. In some forms, the surface molecule comprises a polymer. In some forms, the surface molecule can comprise a microparticle. In some forms, the surface molecule can comprise a fluorocarbon microbubble.

In some forms, the composition, AMT composition, co-composition, or cargo composition can comprise at least 100 AMT peptides. In some forms, the composition, AMT composition, co-composition, or cargo composition can comprise at least 1000 AMT peptides. In some forms, the composition, AMT composition, co-composition, or cargo composition can comprise at least 10,000 AMT peptides.

In some forms, the composition, AMT composition, co-composition, or cargo composition can comprise at least 100 membrane perturbing molecules. In some forms, the composition, AMT composition, co-composition, or cargo composition can comprise at least 1000 membrane perturbing molecules. In some forms, the composition, AMT composition, co-composition, or cargo composition can comprise at least 10,000 membrane perturbing molecules.

In some forms, one or more of the peptides can be modified peptides. In some forms, one or more of the peptides can comprise a methylated peptide. In some forms, one or more of the methylated peptides can comprise a methylated amino acid segment. In some forms, the amino acid segment can be N- or C-methylated in at least one position.

In some forms, one or more of the membrane perturbing molecules can be modified membrane perturbing molecules. In some forms, one or more of the membrane perturbing molecules can comprise a methylated membrane perturbing molecule. In some forms, one or more of the methylated membrane perturbing molecules can comprise a methylated amino acid segment. In some forms, the amino acid segment can be N- or C-methylated in at least one position.

In some forms, the composition can further comprise one or more moieties. In some forms, the moieties can be independently selected from the group consisting of, for example, a pro-apoptotic agent, a pro-inflammatory agent, an immunostimulating agent, an anti-inflammatory agent, an immunosuppressing agent, an anti-angiogenic agent, a pro-angiogenic agent, a cancer chemotherapeutic agent, an anti-bacterial agent, a cytotoxic agent, a polypeptide, a nucleic acid molecule, a small molecule, an image contrast agent, a fluorophore, fluorescein, rhodamine, a radionuclide, indium-111, technetium-99, carbon-11, and carbon-13. In some forms, at least one of the moieties can be a therapeutic agent. In some forms, the therapeutic agent can be Abraxane. In some forms, the therapeutic agent can be paclitaxel. In some forms, the therapeutic agent can be taxol. In some forms, the therapeutic agent can be doxorubicin. In some forms, the therapeutic agent can be rapamycin. In some forms, at least one of the moieties can be a detectable agent. In some forms, the detectable agent can be FAM. In some forms, the moiety inhibits expression of the phosphotidylinositide 3-kinase (PI3K) gamma gene. In some forms, the moiety inhibits PI3K gamma. In some forms, the moiety can be a PI3K gamma inhibitor (such as TG100-115), and TNF-alpha.

In some forms, one or more of the peptides can comprise the amino acid sequence RVLRSGS (SEQ ID NO:2) and one or more of the peptides can be indirectly conjugated to the surface molecule via a linker. In some forms, at least one of the linkers can comprise polyethylene glycol.

Also disclosed are methods of enhancing targeting, delivery, or both of a co-composition into or through a cell, tissue, or both. In some forms, the method can comprising exposing the cell, tissue, or both to the co-composition and an AMT composition, thereby enhancing targeting, delivery, or both of the co-composition into or through the cell, tissue, or both. The AMT composition can comprise any of the disclosed AMT peptides or any of the disclosed compositions that comprise an AMT peptide. In some forms, the AMT composition and the co-composition are not covalently coupled or directly non-covalently associated with each other prior to exposing the cell, tissue, or both.

Also disclosed are methods of enhancing targeting, delivery, or both of a cargo composition into or through a cell, tissue, or both. In some forms, the method can comprise exposing the cell, tissue, or both to the cargo composition and an AMT composition, thereby enhancing targeting, delivery, or both of the cargo composition into or through the cell, tissue, or both. The AMT composition can comprise any of the disclosed AMT peptides or any of the disclosed compositions that comprise an AMT peptide. In some forms, the AMT composition and the cargo composition can be covalently coupled or non-covalently associated with each other.

Also disclosed are methods of enhancing targeting, delivery, or both into or through a cell, tissue, or both. In some forms, the method can comprise exposing the cell, tissue, or both to an AMT composition, thereby enhancing targeting, delivery, or both into or through the cell, tissue, or both. The AMT composition can comprise any of the disclosed AMT peptides or any of the disclosed compositions that comprise an AMT peptide.

In some forms, the cell, tissue, or both can be in a subject. In some forms, the cell, tissue, or both can be exposed to the AMT composition and the co-composition by administering the AMT composition and the co-composition to the subject. In some forms, the cell, tissue, or both can be exposed to the AMT composition and the cargo composition by administering the AMT composition and the cargo composition to the subject. In some forms, the cell, tissue, or both can be exposed to the AMT composition by administering the AMT composition to the subject.

In some forms, the AMT composition can selectively home to activated macrophages. In some forms, the AMT composition can selectively home to tumor associated macrophages. In some forms, the AMT composition and the co-composition can be administered to the subject simultaneously. In some forms, the AMT composition and the co-composition can be administered to the subject in a single composition comprising the AMT composition and the co-composition. In some forms, the AMT composition and the co-composition can be administered to the subject in separate compositions. In some forms, the AMT composition and the co-composition can be administered to the subject at different times. In some forms, the AMT composition and the co-composition can be administered to the subject in separate compositions. In some forms, the AMT composition and the co-composition can be administered to the subject by separate routes.

In some forms, the AMT composition and the co-composition are not bound to each other. In some forms, the AMT composition, co-composition, and/or cargo composition can comprise a therapeutic agent. In some forms, the AMT composition, co-composition, and/or cargo composition can comprise a detectable agent. In some forms, the AMT composition, co-composition, and/or cargo composition can comprise a carrier, vehicle, or both. In some forms, the AMT composition, co-composition, and/or cargo composition can comprise a therapeutic protein, a therapeutic compound, a therapeutic composition, a pro-apototic agent, a pro-inflammatory agent, an immunostimulating agent, an anti-inflammatory agent, an immunosuppressing agent, an anti-angiogenic agent, a pro-angiogenic agent, a cancer chemotherapeutic agent, a toxin, an anti-bacterial agent, a cytotoxic agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination.

In some forms, the AMT composition can comprise one or more accessory molecules. In some forms, the cell, tissue, or both can be exposed to a plurality of peptides. In some forms, the cell, tissue, or both can be exposed to a plurality of cargo compositions. In some forms, the cell, tissue, or both can be exposed to a plurality of AMT compositions. In some forms, the cell, tissue, or both can be exposed to a plurality of co-compositions.

In some forms, the AMT composition, co-composition, and/or cargo composition can have a therapeutic effect. In some forms, the therapeutic effect can be a slowing in the increase of or a reduction of tumor burden. In some forms, the therapeutic effect can be a slowing of the increase of or reduction of tumor size. In some forms, the subject can have one or more sites to be targeted, where the AMT composition, co-composition, and/or cargo composition homes to one or more of the sites to be targeted. In some forms, the subject can have activated macrophages, where the AMT composition, co-composition, and/or cargo composition has a therapeutic effect on the tumor.

Multiple different AMT peptides, AMT compounds, AMT conjugates, AMT compositions, or a combination can be used together. Similarly, multiple different co-compositions, multiple different cargo compositions, or a combination can be used together. Where such multiple different AMT peptides, AMT compounds, AMT conjugates, AMT compositions, or a combination are used together, they can be used with a single type of co-composition, a single type of cargo composition, multiple different co-compositions, multiple different cargo compositions, or a combination. Similarly, when multiple different co-compositions, multiple different cargo compositions, or a combination can be used together, they can be used with a single type of AMT peptide, AMT compound, AMT conjugate, AMT composition, or with multiple different AMT peptides, AMT compounds, AMT conjugates, AMT compositions, or a combination.

For example, an RVLRSGS (SEQ ID NO:2) can be used together with one or multiple different AMT peptides, AMT compounds, AMT conjugates, AMT compositions, or a combination, one or multiple different co-compositions, multiple different cargo compositions, or a combination, or any combination of these. In such combinations, the RVLRSGS (SEQ ID NO:2) itself can be combined in the same conjugate or composition with one or more cargo compositions, one or more accessory molecules, etc.

The cell, tissue, or both can be exposed to combinations of different AMT components and combinations of different co-compositions by administering the AMT components and the co-compositions to the subject. One or more of the AMT components and one or more of the co-compositions can be administered to the subject simultaneously. One or more of the AMT components and one or more of the co-compositions can be administered to the subject in one or more single compositions comprising the AMT component(s) and the co-composition(s). One or more of the AMT components and one or more of the co-compositions can be administered to the subject in one or more separate compositions. One or more of the AMT components and one or more of the co-compositions can be administered to the subject at different times. The AMT composition and the co-composition can be administered to the subject in one or more separate compositions. One or more of the AMT components and one or more of the co-compositions can be administered to the subject by one or more separate routes. In some forms, the AMT composition and the co-composition are not bound to each other.

The cell, tissue, or both can be exposed to combinations of different AMT components and combinations of different cargo compositions by administering the AMT components and the cargo compositions to the subject. One or more of the AMT components and one or more of the cargo compositions can be administered to the subject simultaneously. One or more of the AMT components and one or more of the cargo compositions can be administered to the subject in one or more single compositions comprising the AMT component(s) and the cargo composition(s). One or more of the AMT components and one or more of the cargo compositions can be administered to the subject in one or more separate compositions. One or more of the AMT components and one or more of the cargo compositions can be administered to the subject at different times. The AMT composition and the cargo composition can be administered to the subject in one or more separate compositions. One or more of the AMT components and one or more of the cargo compositions can be administered to the subject by one or more separate routes.

The AMT peptide can be comprised in an amino acid sequence in a protein or peptide. In some forms, the protein or peptide can be targeted, delivered, or both to an activated macrophage when the amino acid sequence is present in the protein or peptide but not when the amino acid sequence is not present in the protein or peptide. In some forms, the protein or peptide can be targeted, delivered, or both to an activated macrophage when the amino acid sequence is present in the protein or peptide but not when the amino acid sequence is not present in the protein or peptide. In some forms, the amino acid sequence is the only functional homing molecule in the protein or peptide. The AMT peptide can be associated with one or more accessory molecules. For example, an accessory molecule can be a part of an amino acid sequence, a protein, or a peptide that comprises the AMT peptide. As another example, the accessory molecule can be covalently coupled or non-covalently associated with the AMT peptide or an amino acid sequence, a protein, or a peptide that comprises the AMT peptide. The accessory molecule can be separate from or overlapping with the AMT peptide. For example, some accessory molecules are amino acid sequences. This can allow the amino acid sequence consisting of the AMT peptide to overlap the amino acid sequence that consists of the accessory amino acid sequence. Alternatively the accessory peptide can be a separate entity that does not overlap with the AMT peptide. In some forms, the accessory molecule can comprise a sequence in, for example, an AMT peptide that binds to a specific receptor distinct from the receptor for the AMT peptide.

The amino acid sequence can comprise one or more accessory peptides. The protein or peptide can comprise one or more accessory peptides. In some forms, the co-composition does not comprise an accessory molecule. The co-composition can comprise one or more accessory molecules. In some forms, the co-composition does not comprise an accessory peptide. The co-composition can comprise one or more accessory peptides. The co-composition can selectively home to activated macrophages. In some forms, the co-composition does not selectively home to tumor associated macrophages. The co-composition can selectively home to tumor associated macrophages. In some forms, the cargo composition does not comprise an accessory molecule. The cargo composition can comprise one or more accessory molecules. In some forms, the cargo composition does not comprise an accessory peptide. The cargo composition can comprise one or more accessory peptides. The cargo composition can selectively home to activated macrophages. In some forms, the cargo composition does not selectively home to tumor associated macrophages. The cargo composition can selectively home to tumor associated macrophages.

A peptide can be an activatable peptide. The activatable peptide can be a protease-activatable peptide. The AMT peptide can be an activatable AMT peptide. The activatable AMT peptide can be a protease-activatable AMT peptide. The AMT peptide can be at the C-terminal end of the protein or peptide. The AMT conjugate can be an activatable AMT conjugate. The activatable AMT conjugate can be a protease-activatable AMT conjugate. The AMT conjugate can be at the C-terminal end of the protein or peptide. The AMT composition can be an activatable AMT composition. The activatable AMT composition can be a protease-activatable AMT composition. The AMT composition can be at the C-terminal end of the protein or peptide.

The AMT peptide can be associated with one or more therapeutic agents. For example, a therapeutic agent can be a part of an amino acid sequence, a protein, or a peptide that comprises the AMT peptide. As another example, the therapeutic agent can be covalently coupled or non-covalently associated with the AMT peptide or an amino acid sequence, a protein, or a peptide that comprises the AMT peptide. The therapeutic agent can be separate from or overlapping with the AMT peptide. For example, some therapeutic agents are amino acid sequences. This can allow the amino acid sequence consisting of the AMT peptide to overlap the amino acid sequence that consists of the therapeutic amino acid sequence. Alternatively the therapeutic agent can be a separate entity that does not overlap with the AMT peptide. In some forms, the therapeutic agent can comprise a sequence in, for example, a peptide that binds to a specific receptor distinct from the receptor for the AMT peptide.

The disclosed peptides home to specific cells (activated macrophages) and many homing molecules home to the vasculature of the target tissue. However, for the sake of convenience homing is referred to in some places herein as homing to the tissue associated with the macrophages, or with the vasculature, to which the peptide or homing peptide may actually home. Thus, for example, a homing peptide that homes to tumor associated macrophages can be referred to herein as homing to tumor tissue or to tumor cells. By including or associating a peptide or homing peptide with, for example, a protein, peptide, amino acid sequence, co-composition, or cargo composition, the protein, peptide, amino acid sequence, co-composition, or cargo composition can be targeted or can home to the target of the peptide or homing peptide. In this way, the protein, peptide, amino acid sequence, co-composition, or cargo composition, or can be said to home to the target of the peptide or homing peptide. For convenience and unless otherwise indicated, reference to homing of a protein, peptide, amino acid sequence, co-composition, cargo composition, etc. is intended to indicate that the protein, peptide, amino acid sequence, co-composition, cargo composition, etc. includes or is associated with an appropriate peptide or homing peptide.

In some forms, the AMT peptide and the co-composition are not covalently coupled or directly non-covalently associated with each other. In some forms, the co-composition does not comprise a peptide. The co-composition can comprise one or more peptides. In some forms, the co-composition does not comprise an AMT peptide or a homing peptide. The co-composition can comprise one or more AMT peptides or homing peptides. The co-composition can selectively home to activated macrophages. In some forms, the co-composition does not selectively home to tumor associated macrophages. The co-composition can selectively home to tumor associated macrophages.

In some forms, the AMT peptide and the cargo composition are not covalently coupled or directly non-covalently associated with each other. In some forms, the cargo composition does not comprise a peptide. The cargo composition can comprise one or more peptides. In some forms, the cargo composition does not comprise an AMT peptide or a homing peptide. The cargo composition can comprise one or more AMT peptides or homing peptides. The cargo composition can selectively home to activated macrophages. In some forms, the cargo composition does not selectively home to tumor associated macrophages. The cargo composition can selectively home to tumor associated macrophages.

The AMT peptide can be the only functional homing peptide in the AMT composition, conjugate, molecule, protein, peptide, etc. The selected amino acid sequence can be the only functional homing peptide in the AMT composition, conjugate, molecule, protein, peptide, etc.

Disclosed herein is a method of forming an AMT composition, the method comprising selecting an amino acid sequence for homing to activated macrophages, and causing an AMT peptide to be covalently coupled to or non-covalently associated with the selected amino acid sequence, wherein the AMT composition comprises the selected amino acid sequence and the coupled or associated AMT peptide.

Disclosed is a method of making an AMT composition comprising: (a) selecting an amino acid sequence for homing to activated macrophages, (b) causing an AMT peptide to be covalently coupled to or non-covalently associated with the selected amino acid sequence, wherein the AMT composition comprises the selected amino acid sequence and the coupled or associated AMT peptide.

Also disclosed is a method of delivering a co-composition into a cell, the method comprising: exposing the cell to an AMT composition and the co-composition, wherein the AMT composition can then enter the cell, thereby delivering the co-composition into the cell.

Also disclosed is a method of causing a co-composition to penetrate tissue, the method comprising: exposing the tissue to an AMT composition and the co-composition, wherein the AMT composition can then enter and exit cells in the tissue, thereby causing the co-composition to penetrate the tissue.

Also disclosed is a method of delivering a cargo composition into a cell, the method comprising: exposing the cell to an AMT composition and the cargo composition, wherein the AMT composition can then enter the cell, thereby delivering the cargo composition into the cell.

Also disclosed is a method of causing a cargo composition to penetrate tissue, the method comprising: exposing the tissue to an AMT composition and the cargo composition, wherein the AMT composition can then enter and exit cells in the tissue, thereby causing the cargo composition to penetrate the tissue.

Also disclosed is a method of delivering a cargo composition into a cell, the method comprising: exposing the cell to an AMT composition and the cargo composition, wherein the AMT composition comprises the cargo composition, wherein the AMT composition can then enter the cell, thereby delivering the cargo composition into the cell.

Further disclosed is a method of causing a cargo composition to penetrate tissue, the method comprising: exposing the tissue to the cargo composition and an AMT composition comprising an activatable AMT peptide, wherein the AMT composition comprises the cargo composition, whereupon a cleaving agent activates the activatable AMT peptide of the AMT composition, wherein the AMT composition can then enter and pass cells in the tissue, thereby causing the cargo composition to penetrate the tissue.

Cells that can internalize an AMT peptide can be identified by (a) exposing a cell to an AMT peptide; and (b) determining if the AMT peptide was internalized. The cell can be in an assay, for example. Cells that can internalize an activatable peptide can be identified by (a) exposing a cell to an activatable peptide; (b) determining if the activatable peptide was internalized. The activatable peptide can be unblocked before exposure to the cell, but does not need to be. This can be used to test the blocking ability of the blocker, for example.

Subjects harboring activated macrophages, can be identified as a candidate for RVL-based therapy by (a) exposing tissue from the subject to an AMT peptide; and (b) determining if the AMT peptide binds to the tissue, wherein a bound AMT peptide identifies the subject as being a candidate for RVL-based therapy.

In some forms, the AMT peptide and the co-composition are not covalently coupled or directly non-covalently associated with each other. In some forms, the AMT conjugate and the co-composition are not covalently coupled or directly non-covalently associated with each other. In some forms, the AMT composition and the co-composition are not covalently coupled or directly non-covalently associated with each other. In some forms, the AMT peptide and the cargo composition are covalently coupled or non-covalently associated with each other. In some forms, the AMT conjugate and the cargo composition are covalently coupled or non-covalently associated with each other. In some forms, the AMT composition and the cargo composition are covalently coupled or non-covalently associated with each other.

Disclosed are compositions comprising an AMT peptide and a co-composition. Also disclosed are compositions comprising an AMT conjugate and a co-composition. Also disclosed are compositions comprising an AMT composition and a co-composition. Disclosed are compositions comprising an AMT peptide and a co-composition, wherein the AMT peptide and the co-composition are not covalently coupled or directly non-covalently associated with each other. Also disclosed are compositions comprising an AMT conjugate and a co-composition, wherein the AMT conjugate and the co-composition are not covalently coupled or directly non-covalently associated with each other. Also disclosed are compositions comprising an AMT composition and a co-composition, wherein the AMT composition and the co-composition are not covalently coupled or directly non-covalently associated with each other.

Disclosed are compositions comprising an AMT peptide and one or more co-compositions. Also disclosed are compositions comprising an AMT conjugate and one or more co-composition. Also disclosed are compositions comprising an AMT composition and one or more co-compositions. Disclosed are compositions comprising an AMT peptide and one or more co-compositions, wherein the AMT peptide and at least one of the co-compositions are not covalently coupled or directly non-covalently associated with each other. Also disclosed are compositions comprising an AMT conjugate and one or more co-compositions, wherein the AMT conjugate and at least one of the co-compositions are not covalently coupled or directly non-covalently associated with each other. Also disclosed are compositions comprising an AMT composition and one or more co-compositions, wherein the AMT composition and at least one of the co-compositions are not covalently coupled or directly non-covalently associated with each other.

Disclosed are compositions comprising an AMT peptide and a cargo composition. Also disclosed are compositions comprising an AMT conjugate and a cargo composition. Also disclosed are compositions comprising an AMT composition and a cargo composition. Disclosed are compositions comprising an AMT peptide and a cargo composition, wherein the AMT peptide and the cargo composition are covalently coupled or non-covalently associated with each other. Also disclosed are compositions comprising an AMT conjugate and a cargo composition, wherein the AMT conjugate and the cargo composition are covalently coupled or non-covalently associated with each other. Also disclosed are compositions comprising an AMT composition and a cargo composition, wherein the AMT composition and the cargo composition are covalently coupled or non-covalently associated with each other.

Disclosed are compositions comprising an AMT peptide and one or more cargo compositions. Also disclosed are compositions comprising an AMT conjugate and one or more cargo composition. Also disclosed are compositions comprising an AMT composition and one or more cargo compositions. Disclosed are compositions comprising an AMT peptide and one or more cargo compositions, wherein the AMT peptide and at least one of the cargo compositions are covalently coupled or non-covalently associated with each other. Also disclosed are compositions comprising an AMT conjugate and one or more cargo compositions, wherein the AMT conjugate and at least one of the cargo compositions are covalently coupled or non-covalently associated with each other. Also disclosed are compositions comprising an AMT composition and one or more cargo compositions, wherein the AMT composition and at least one of the cargo compositions are covalently coupled or non-covalently associated with each other.

Also disclosed are compositions comprising an AMT peptide, an accessory molecule, and a co-composition, wherein the AMT peptide and the co-composition are not covalently coupled or directly non-covalently associated with each other, wherein the AMT peptide and the accessory molecule are covalently coupled or non-covalently associate with each other. Also disclosed are compositions comprising an AMT conjugate, an accessory molecule, and a co-composition, wherein the AMT conjugate and the co-composition are not covalently coupled or directly non-covalently associated with each other, wherein the AMT conjugate and the accessory molecule are covalently coupled or non-covalently associate with each other. Also disclosed are compositions comprising an AMT composition, an accessory molecule, and a co-composition, wherein the AMT composition and the co-composition are not covalently coupled or directly non-covalently associated with each other, wherein the AMT composition and the accessory molecule are covalently coupled or non-covalently associate with each other. Also disclosed are compositions comprising an AMT peptide, an accessory molecule, and a co-composition, wherein the AMT peptide and the co-composition are not covalently coupled or directly non-covalently associated with each other, wherein the AMT peptide comprises the accessory molecule. Also disclosed are compositions comprising an AMT conjugate, an accessory molecule, and a co-composition, wherein the AMT conjugate and the co-composition are not covalently coupled or directly non-covalently associated with each other, wherein the AMT conjugate comprises the accessory molecule. Also disclosed are compositions comprising an AMT composition, an accessory molecule, and a co-composition, wherein the AMT composition and the co-composition are not covalently coupled or directly non-covalently associated with each other, wherein the AMT composition comprises the accessory molecule. In these compositions, the accessory molecule can be or can comprise an accessory peptide. In these compositions, the composition can comprise one or more co-compositions and/or one or more accessory molecules, wherein the AMT peptide, AMT conjugate, or AMT composition and at least one of the co-compositions are not covalently coupled or directly non-covalently associated with each other, wherein the AMT peptide, AMT conjugate, or AMT composition and at least one of the accessory molecules are covalently coupled or non-covalently associated with each other.

Also disclosed are compositions comprising an AMT peptide, a homing molecule, and a co-composition, wherein the AMT peptide and the co-composition are not covalently coupled or directly non-covalently associated with each other, wherein the AMT peptide and the homing molecule are covalently coupled or non-covalently associate with each other. Also disclosed are compositions comprising an AMT conjugate, a homing molecule, and a co-composition, wherein the AMT conjugate and the co-composition are not covalently coupled or directly non-covalently associated with each other, wherein the AMT conjugate and the homing molecule are covalently coupled or non-covalently associate with each other. Also disclosed are compositions comprising an AMT composition, a homing molecule, and a co-composition, wherein the AMT composition and the co-composition are not covalently coupled or directly non-covalently associated with each other, wherein the AMT composition and the homing molecule are covalently coupled or non-covalently associate with each other. Also disclosed are compositions comprising an AMT peptide, a homing molecule, and a co-composition, wherein the AMT peptide and the co-composition are not covalently coupled or directly non-covalently associated with each other, wherein the AMT peptide comprises the homing molecule. Also disclosed are compositions comprising an AMT conjugate, a homing molecule, and a co-composition, wherein the AMT conjugate and the co-composition are not covalently coupled or directly non-covalently associated with each other, wherein the AMT conjugate comprises the homing molecule. Also disclosed are compositions comprising an AMT composition, a homing molecule, and a co-composition, wherein the AMT composition and the co-composition are not covalently coupled or directly non-covalently associated with each other, wherein the AMT composition comprises the homing molecule. In these compositions, the homing molecule can be or can comprise a homing peptide. In these compositions, the composition can comprise one or more co-compositions and/or one or more homing molecules, wherein the AMT peptide, AMT conjugate, or AMT composition and at least one of the co-compositions are not covalently coupled or directly non-covalently associated with each other, wherein the AMT peptide, AMT conjugate, or AMT composition and at least one of the homing molecules are covalently coupled or non-covalently associated with each other.

Also disclosed are compositions comprising an AMT peptide, an accessory molecule, and a cargo composition, wherein the AMT peptide and the cargo composition are covalently coupled or non-covalently associated with each other, wherein the AMT peptide and the accessory molecule are covalently coupled or non-covalently associate with each other. Also disclosed are compositions comprising an AMT conjugate, an accessory molecule, and a cargo composition, wherein the AMT conjugate and the cargo composition are covalently coupled or non-covalently associated with each other, wherein the AMT conjugate and the accessory molecule are covalently coupled or non-covalently associate with each other. Also disclosed are compositions comprising an AMT composition, an accessory molecule, and a cargo composition, wherein the AMT composition and the cargo composition are covalently coupled or non-covalently associated with each other, wherein the AMT composition and the accessory molecule are covalently coupled or non-covalently associate with each other. Also disclosed are compositions comprising an AMT peptide, an accessory molecule, and a cargo composition, wherein the AMT peptide and the cargo composition are covalently coupled or non-covalently associated with each other, wherein the AMT peptide comprises the accessory molecule. Also disclosed are compositions comprising an AMT conjugate, an accessory molecule, and a cargo composition, wherein the AMT conjugate and the cargo composition are covalently coupled or non-covalently associated with each other, wherein the AMT conjugate comprises the accessory molecule. Also disclosed are compositions comprising an AMT composition, an accessory molecule, and a cargo composition, wherein the AMT composition and the cargo composition are covalently coupled or non-covalently associated with each other, wherein the AMT composition comprises the accessory molecule. In these compositions, the accessory molecule can be or can comprise an accessory peptide. In these compositions, the composition can comprise one or more cargo compositions and/or one or more accessory molecules, wherein the AMT peptide, AMT conjugate, or AMT composition and at least one of the cargo compositions are covalently coupled or non-covalently associated with each other, wherein the AMT peptide, AMT conjugate, or AMT composition and at least one of the accessory molecules are covalently coupled or non-covalently associated with each other.

Also disclosed are compositions comprising an AMT peptide, a peptide, and a cargo composition, wherein the AMT peptide and the cargo composition are covalently coupled or non-covalently associated with each other, wherein the AMT peptide and the peptide are covalently coupled or non-covalently associate with each other. Also disclosed are compositions comprising an AMT conjugate, a peptide, and a cargo composition, wherein the AMT conjugate and the cargo composition are covalently coupled or non-covalently associated with each other, wherein the AMT conjugate and the peptide are covalently coupled or non-covalently associate with each other. Also disclosed are compositions comprising an AMT composition, a peptide, and a cargo composition, wherein the AMT composition and the cargo composition are covalently coupled or non-covalently associated with each other, wherein the AMT composition and the peptide are covalently coupled or non-covalently associate with each other. Also disclosed are compositions comprising an AMT peptide, a peptide, and a cargo composition, wherein the AMT peptide and the cargo composition are covalently coupled or non-covalently associated with each other, wherein the AMT peptide comprises the peptide. Also disclosed are compositions comprising an AMT conjugate, a peptide, and a cargo composition, wherein the AMT conjugate and the cargo composition are covalently coupled or non-covalently associated with each other, wherein the AMT conjugate comprises the peptide. Also disclosed are compositions comprising an AMT composition, a peptide, and a cargo composition, wherein the AMT composition and the cargo composition are covalently coupled or non-covalently associated with each other, wherein the AMT composition comprises the peptide. In these compositions, the peptide can be or can comprise a homing peptide. In these compositions, the composition can comprise one or more cargo compositions and/or one or more peptides, wherein the AMT peptide, AMT conjugate, or AMT composition and at least one of the cargo compositions are not covalently coupled or directly non-covalently associated with each other, wherein the AMT peptide, AMT conjugate, or AMT composition and at least one of the peptides are covalently coupled or non-covalently associated with each other.

Also disclosed are compositions comprising a protein or peptide and a co-composition, wherein the protein or peptide comprises an AMT peptide and an accessory peptide, wherein the AMT peptide and the co-composition are not covalently coupled or directly non-covalently associated with each other. Also disclosed are compositions comprising a protein or peptide and a co-composition, wherein the protein or peptide comprises an amino acid sequence, wherein the amino acid sequence comprises an AMT peptide and an accessory peptide, wherein the AMT peptide and the co-composition are not covalently coupled or directly non-covalently associated with each other. In these compositions, the composition can comprise one or more co-compositions and/or one or more accessory peptides, wherein the protein or peptide and at least one of the co-compositions are not covalently coupled or directly non-covalently associated with each other, wherein the protein or peptide and at least one of the accessory peptides are covalently coupled or non-covalently associated with each other.

Also disclosed are compositions comprising a protein or peptide and a co-composition, wherein the protein or peptide comprises an AMT peptide and a homing peptide, wherein the AMT peptide and the co-composition are not covalently coupled or directly non-covalently associated with each other. Also disclosed are compositions comprising a protein or peptide and a co-composition, wherein the protein or peptide comprises an amino acid sequence, wherein the amino acid sequence comprises an AMT peptide and a homing peptide, wherein the AMT peptide and the co-composition are not covalently coupled or directly non-covalently associated with each other. In these compositions, the composition can comprise one or more co-compositions and/or one or more homing peptides, wherein the protein or peptide and at least one of the co-compositions are not covalently coupled or directly non-covalently associated with each other, wherein the protein or peptide and at least one of the homing peptides are covalently coupled or non-covalently associated with each other.

Also disclosed are compositions comprising a protein or peptide and a cargo composition, wherein the protein or peptide comprises an AMT peptide and an accessory peptide, wherein the AMT peptide and the cargo composition are covalently coupled or non-covalently associated with each other. Also disclosed are compositions comprising a protein or peptide and a cargo composition, wherein the protein or peptide comprises an amino acid sequence, wherein the amino acid sequence comprises an AMT peptide and an accessory peptide, wherein the AMT peptide and the cargo composition are covalently coupled or non-covalently associated with each other. In these compositions, the composition can comprise one or more cargo compositions and/or one or more accessory peptides, wherein the protein or peptide and at least one of the cargo compositions are covalently coupled or non-covalently associated with each other, wherein the protein or peptide and at least one of the accessory peptides are covalently coupled or non-covalently associated with each other.

Also disclosed are compositions comprising a protein or peptide and a cargo composition, wherein the protein or peptide comprises an AMT peptide and a homing peptide, wherein the AMT peptide and the cargo composition are covalently coupled or non-covalently associated with each other. Also disclosed are compositions comprising a protein or peptide and a cargo composition, wherein the protein or peptide comprises an amino acid sequence, wherein the amino acid sequence comprises an AMT peptide and a homing peptide, wherein the AMT peptide and the cargo composition are covalently coupled or non-covalently associated with each other. In these compositions, the composition can comprise one or more cargo compositions and/or one or more homing peptides, wherein the protein or peptide and at least one of the cargo compositions are not covalently coupled or directly non-covalently associated with each other, wherein the protein or peptide and at least one of the homing peptides are covalently coupled or non-covalently associated with each other.

As used herein, reference to components (such as an AMT peptide and a co-composition) as being "not covalently coupled" means that the components are not connected via covalent bonds (for example, that the AMT peptide and the co-composition are not connected via covalent bonds). That is, there is no continuous chain of covalent bonds between, for example, the AMT peptide and the co-composition. Conversely, reference to components (such as an AMT peptide and a cargo composition) as being "covalently coupled" means that the components are connected via covalent bonds (for example, that the AMT peptide and the cargo composition are connected via covalent bonds). That is, there is a continuous chain of covalent bonds between, for example, the AMT peptide and the cargo composition. Components can be covalently coupled either directly or indirectly. Direct covalent coupling refers to the presence of a covalent bond between atoms of each of the components. Indirect covalent coupling refers to the absence of a covalent bond between atoms of each of the components. That is, some other atom or atoms not belonging to either of the coupled components intervenes between atoms of the components. Both direct and indirect covalent coupling involve a continuous chain of covalent bonds.

Non-covalent association refers to association of components via non-covalent bonds and interactions. A non-covalent association can be either direct or indirect. A direct non-covalent association refers to a non-covalent bond involving atoms that are each respectively connected via a chain of covalent bonds to the components. Thus, in a direct non-covalent association, there is no other molecule intervening between the associated components. An indirect non-covalent association refers to any chain of molecules and bonds linking the components where the components are not covalently coupled (that is, there is a least one separate molecule other than the components intervening between the components via non-covalent bonds).

Reference to components (such as an AMT peptide and a co-composition) as not being "non-covalently associated" means that there is no direct or indirect non-covalent association between the components. That is, for example, no atom covalently coupled to an AMT peptide is involved in a non-covalent bond with an atom covalently coupled to a co-composition. Within this meaning, an AMT peptide and a co-composition can be together in a composition where they are indirectly associated via multiple intervening non-covalent bonds while not being non-covalently associated as that term is defined herein. For example, an AMT peptide and a co-composition can be mixed together in a carrier where they are not directly non-covalently associated. An AMT peptide and a co-composition that are referred to as not indirectly non-covalently associated cannot be mixed together in a continuous composition. Reference to components (such as an AMT peptide and a co-composition) as not being "directly non-covalently associated" means that there is no direct non-covalent association between the components (an indirect non-covalent association may be present). Reference to components (such as an AMT peptide and a co-composition) as not being "indirectly non-covalently associated" means that there is no direct or indirect non-covalent association between the components.

It is understood that components can be non-covalently associated via multiple chains and paths including both direct and indirect non-covalent associations. For the purposes of these definitions, the presence a single direct non-covalent association makes the association a direct non-covalent association even if there are also indirect non-covalent associations present. Similarly, the presence of a covalent connection between components means the components are covalently coupled even if there are also non-covalent associations present. It is also understood that covalently coupled components that happened to lack any non-covalent association with each other are not considered to fall under the definition of components that are not non-covalently associated.

In some forms, the co-composition does not comprise a peptide. The co-composition can comprise a peptide. In some forms, the co-composition does not comprise a homing peptide. The co-composition can comprise a homing peptide. The co-composition can selectively home to activated macrophages. In some forms, the co-composition does not selectively home to tumor associated macrophages. The co-composition can selectively home to tumor associated macrophages. In some forms, the co-composition does not comprise an accessory molecule. The co-composition can comprise an accessory molecule. In some forms, the co-composition does not comprise an accessory peptide. The co-composition can comprise an accessory peptide. The co-composition can selectively home to activated macrophages.

The AMT peptide can be associated with one or more accessory molecules. For example, an accessory molecule can be a part of an amino acid sequence, protein, peptide, conjugate, or composition that comprises the AMT peptide. As another example, the accessory molecule can be covalently coupled or non-covalently associated with the AMT peptide or an amino acid sequence, protein, peptide, conjugate, or composition that comprises the AMT peptide. Accessory molecules can be any molecule, compound, component, etc. that has a useful function and that can be used in combination with an AMT composition, AMT conjugate, AMT molecule, AMT protein, and/or AMT peptide. Examples of useful accessory molecules include peptides, targeting molecules, affinity ligands, cell penetrating molecules, endosomal escape molecules, subcellular targeting molecules, nuclear targeting molecules. Different accessory molecules can have similar or different functions from each other. Accessory molecules having similar functions, different functions, or both, can be associated an AMT composition, AMT conjugate, AMT molecule, AMT protein, and/or AMT peptide.

The accessory molecule can be separate from or overlapping with the AMT peptide. For example, some accessory molecules are amino acid sequences. This can allow the amino acid sequence consisting of the AMT peptide to overlap the amino acid sequence that consists of the accessory amino acid sequence. For example, iRGD, LyP-1, iNGR, and RGR peptides each contain both an accessory sequence and AMT sequence overlapping with one another in the peptide. Alternatively the accessory molecule can be a separate entity that does not overlap with the AMT peptide. In some forms, the accessory molecule can comprise a sequence in, for example, a peptide that binds to a specific receptor distinct from the receptor for the AMT peptide.

The AMT peptide can be associated with one or more accessory molecules. For example, an accessory molecule can be a part of an amino acid sequence, protein, peptide, conjugate, or composition that comprises the AMT peptide. As another example, the accessory molecule can be covalently coupled or non-covalently associated with the AMT peptide or an amino acid sequence, protein, peptide, conjugate, or composition that comprises the AMT peptide. The AMT conjugate can be associated with one or more accessory molecules. For example, an accessory molecule can be a part of a conjugate or composition that comprises the AMT conjugate. As another example, the accessory molecule can be covalently coupled or non-covalently associated with the AMT conjugate or a conjugate or composition that comprises the AMT conjugate. The AMT composition can be associated with one or more accessory molecules. For example, an accessory molecule can be a part of a composition that comprises the AMT composition. As another example, the accessory molecule can be covalently coupled or non-covalently associated with the AMT composition or a composition that comprises the AMT composition.

The amino acid sequence can be associated with one or more accessory molecules. For example, an accessory molecule can be a part of an amino acid sequence, protein, peptide, conjugate, or composition that comprises the amino acid sequence. As another example, the accessory molecule can be covalently coupled or non-covalently associated with the amino acid sequence or an amino acid sequence, protein, peptide, conjugate, or composition that comprises the amino acid sequence. The protein or peptide can be associated with one or more accessory molecules. For example, an accessory molecule can be a part of a protein, peptide, conjugate, or composition that comprises the peptide. As another example, the accessory molecule can be covalently coupled or non-covalently associated with the peptide or a protein, peptide, conjugate, or composition that comprises the peptide. For example, an accessory molecule can be a part of a protein, conjugate, or composition that comprises the protein. As another example, the accessory molecule can be covalently coupled or non-covalently associated with the protein or a protein, conjugate, or composition that comprises the protein. The conjugate can be associated with one or more accessory molecules. For example, an accessory molecule can be a part of a conjugate or composition that comprises the conjugate. As another example, the accessory molecule can be covalently coupled or non-covalently associated with the conjugate or a conjugate or composition that comprises the conjugate. The composition can be associated with one or more accessory molecules. For example, an accessory molecule can be a part of a composition that comprises the composition. As another example, the accessory molecule can be covalently coupled or non-covalently associated with the composition or a composition that comprises the composition.

The AMT peptide can be associated with one or more peptides. For example, a peptide can be a part of an amino acid sequence, protein, peptide, conjugate, or composition that comprises the AMT peptide. As another example, the peptide can be covalently coupled or non-covalently associated with the AMT peptide or an amino acid sequence, protein, peptide, conjugate, or composition that comprises the AMT peptide. The peptide can be separate from or overlapping with the AMT peptide. For example, some peptides are amino acid sequences. This can allow the amino acid sequence consisting of the AMT peptide to overlap the amino acid sequence that consists of the homing amino acid sequence. Alternatively the peptide can be a separate entity that does not overlap with the AMT peptide. In some forms, the peptide can comprise a sequence in, for example, an AMT peptide that binds to a specific receptor distinct from the receptor for the AMT peptide.

The AMT peptide can be associated with one or more peptides. For example, a peptide can be a part of an amino acid sequence, protein, peptide, conjugate, or composition that comprises the AMT peptide. As another example, the peptide can be covalently coupled or non-covalently associated with the AMT peptide or an amino acid sequence, protein, peptide, conjugate, or composition that comprises the AMT peptide. The AMT conjugate can be associated with one or more peptides. For example, a peptide can be a part of a conjugate or composition that comprises the AMT conjugate. As another example, the peptide can be covalently coupled or non-covalently associated with the AMT conjugate or a conjugate or composition that comprises the AMT conjugate. The AMT composition can be associated with one or more peptides. For example, a peptide can be a part of a composition that comprises the AMT composition. As another example, the peptide can be covalently coupled or non-covalently associated with the AMT composition or a composition that comprises the AMT composition.

The amino acid sequence can be associated with one or more peptides. For example, a peptide can be a part of an amino acid sequence, protein, peptide, conjugate, or composition that comprises the amino acid sequence. As another example, the peptide can be covalently coupled or non-covalently associated with the amino acid sequence or an amino acid sequence, protein, peptide, conjugate, or composition that comprises the amino acid sequence. The protein or peptide can be associated with one or more peptides. For example, a peptide can be a part of a protein, peptide, conjugate, or composition that comprises the peptide. As another example, the peptide can be covalently coupled or non-covalently associated with the peptide or a protein, peptide, conjugate, or composition that comprises the peptide. For example, a peptide can be a part of a protein, conjugate, or composition that comprises the protein. As another example, the peptide can be covalently coupled or non-covalently associated with the protein or a protein, conjugate, or composition that comprises the protein. The conjugate can be associated with one or more peptides. For example, a peptide can be a part of a conjugate or composition that comprises the conjugate. As another example, the peptide can be covalently coupled or non-covalently associated with the conjugate or a conjugate or composition that comprises the conjugate. The composition can be associated with one or more peptides. For example, a peptide can be a part of a composition that comprises the composition. As another example, the peptide can be covalently coupled or non-covalently associated with the composition or a composition that comprises the composition.

The amino acid sequence can be selected for homing to activated macrophages.

The protein or peptide can be selected for homing to activated macrophages. The conjugate can be selected for homing to activated macrophages. The composition can be selected for homing to activated macrophages.

The AMT peptide, AMT conjugate, AMT composition, amino acid sequence, protein or peptide, conjugate, composition, co-composition, cargo composition, or a combination can selectively home to activated macrophages. The AMT peptide, AMT conjugate, AMT composition, amino acid sequence, protein or peptide, conjugate, composition, co-composition, cargo composition, or a combination can selectively home to tumor associated macrophages. The AMT peptide, AMT conjugate, AMT composition, amino acid sequence, protein or peptide, conjugate, composition, co-composition, cargo composition, or a combination can selectively home to one or more particular types of tumor. The AMT peptide, AMT conjugate, AMT composition, amino acid sequence, protein or peptide, conjugate, composition, co-composition, cargo composition, or a combination can selectively home to the vasculature of one or more particular types of tumor. The AMT peptide, AMT conjugate, AMT composition, amino acid sequence, protein or peptide, conjugate, composition, co-composition, cargo composition, or a combination can selectively home to one or more particular stages of a tumor or cancer. The AMT peptide, AMT conjugate, AMT composition, amino acid sequence, protein or peptide, conjugate, composition, co-composition, cargo composition, or a combination can selectively home to the vasculature of one or more particular stages of a tumor or cancer. The AMT peptide, AMT conjugate, AMT composition, amino acid sequence, protein or peptide, conjugate, composition, co-composition, cargo composition, or a combination can selectively home to one or more particular stages of one or more particular types of tumor. The AMT peptide, AMT conjugate, AMT composition, amino acid sequence, protein or peptide, conjugate, composition, co-composition, cargo composition, or a combination can selectively home to the vasculature of one or more different stages of one or more particular types of tumor.

The AMT peptide, AMT conjugate, AMT composition, amino acid sequence, protein or peptide, conjugate, composition, co-composition, cargo composition, or a combination can selectively home to lung tissue. The AMT peptide, AMT conjugate, AMT composition, amino acid sequence, protein or peptide, conjugate, composition, co-composition, cargo composition, or a combination can selectively home to lung vasculature. The AMT peptide, AMT conjugate, AMT composition, amino acid sequence, protein or peptide, conjugate, composition, co-composition, cargo composition, or a combination can selectively home to heart tissue. The AMT peptide, AMT conjugate, AMT composition, amino acid sequence, protein or peptide, conjugate, composition, co-composition, cargo composition, or a combination can selectively home to heart vasculature. The AMT peptide, AMT conjugate, AMT composition, amino acid sequence, protein or peptide, conjugate, composition, co-composition, cargo composition, or a combination can selectively home to brain cells, brain stem cells, brain tissue, and/or brain vasculature, kidney cells, kidney stem cells, kidney tissue, and/or kidney vasculature, skin cells, skin stem cells, skin tissue, and/or skin vasculature, lung cells, lung tissue, and/or lung vasculature, pancreatic cells, pancreatic tissue, and/or pancreatic vasculature, intestinal cells, intestinal tissue, and/or intestinal vasculature, adrenal gland cells, adrenal tissue, and/or adrenal vasculature, retinal cells, retinal tissue, and/or retinal vasculature, liver cells, liver tissue, and/or liver vasculature, prostate cells, prostate tissue, and/or prostate vasculature, endometriosis cells, endometriosis tissue, and/or endometriosis vasculature, ovary cells, ovary tissue, and/or ovary vasculature, tumor cells, tumors, tumor blood vessels, and/or tumor vasculature, bone cells, bone tissue, and/or bone vasculature, bone marrow cells, bone marrow tissue, and/or bone marrow vasculature, cartilage cells, cartilage tissue, and/or cartilage vasculature, stem cells, embryonic stem cells, pluripotent stem cells, induced pluripotent stem cells, adult stem cells, hematopoietic stem cells, neural stem cells, mesenchymal stem cells, mammary stem cells, endothelial stem cells, olfactory adult stem cells, neural crest stem cells, cancer stem cells, blood cells, erythrocytes, platelets, leukocytes, granulocytes, neutrophils, eosinphils, basophils, lymphoid cells, lymphocytes, monocytes, wound vasculature, vasculature of injured tissue, vasculature of inflamed tissue, atherosclerotic plaques, or a combination.

AMT compositions, AMT conjugates, AMT molecules, AMT proteins, and AMT peptides can be designed and produced in any suitable manner. For example, the AMT peptide in the disclosed AMT compositions, AMT conjugates, AMT molecules, and AMT proteins can be designed or produced by selecting an amino acid sequence for homing to activated macrophages.

The peptide can be an activatable peptide. The activatable peptide can be a protease-activatable peptide. The protease-activatable peptide can be activatable by a serine protease, plasmin, a plasminogen activator, urokinase, a proprotein convertase, a furin, a carboxypeptidase, carboxypeptidase A, a glutamate-specific carboxypeptidase, a proline-specific carboxypeptidase, PSMA, or a combination.

The AMT peptide can be comprised in an amino acid sequence. The amino acid sequence can be comprised in a protein or peptide. The AMT peptide can be comprised in a protein or peptide. In some forms, the protein or peptide can be homing to activated macrophages when the amino acid sequence is present in the protein or peptide but not when the amino acid sequence is not present in the protein or peptide. In some forms, the protein or peptide can be homing to activated macrophages when the amino acid sequence is present in the protein or peptide but not when the amino acid sequence is not present in the protein or peptide. In some forms, the protein or peptide can be internalized into a cell and penetrate tissue when the AMT amino acid sequence is present in the protein or peptide but not when the AMT amino acid sequence is not present in the protein or peptide.

In some forms, the AMT amino acid sequence can be internalized into a cell, penetrate tissue, or both without being associated with the co-composition. In some forms, the AMT amino acid sequence can be internalized into a cell, penetrate tissue, or both without being associated with the cargo composition. In some forms, the AMT amino acid sequence can penetrate tissue without being associated with the co-composition. In some forms, the AMT amino acid sequence can penetrate tissue without being associated with the cargo composition. In some forms, the AMT amino acid sequence can be internalized into a cell and penetrate tissue without being associated with the co-composition. In some forms, the AMT amino acid sequence can be internalized into a cell and penetrate tissue without being associated with the cargo composition. In some forms, the AMT amino acid sequence can be the only functional internalization element in the protein or peptide.

In some forms, the internalization, penetration, or both of the co-composition or cargo composition into or through a cell, tissue, or both can be enhanced when the AMT amino acid sequence is present in the protein or peptide but not when the amino acid sequence is not present in the protein or peptide. In some forms, the penetration of the co-composition or cargo composition into or through tissue can be enhanced when the AMT amino acid sequence is present in the protein or peptide but not when the amino acid sequence is not present in the protein or peptide. In some forms, the internalization and penetration of the co-composition or cargo composition into or through a cell and tissue can be enhanced when the AMT amino acid sequence is present in the protein or peptide but not when the amino acid sequence is not present in the protein or peptide. In some forms, the internalization, penetration, or both of the co-composition or cargo composition into or through a cell, tissue, or both can be enhanced when the AMT peptide is present in the protein or peptide but not when the AMT peptide is not present in the protein or peptide. In some forms, the penetration of the co-composition or cargo composition into or through tissue can be enhanced when the AMT peptide is present in the protein or peptide but not when the AMT peptide is not present in the protein or peptide. In some forms, the internalization and penetration of the co-composition or cargo composition into or through a cell and tissue can be enhanced when the AMT peptide is present in the protein or peptide but not when the AMT peptide is not present in the protein or peptide.

The amino acid sequence can be associated with one or more accessory molecules. The protein or peptide can be associated with one or more accessory molecules. One or more of the accessory molecules can be independently a peptide, a targeting molecule, an affinity ligand, a cell penetrating peptide, an endosomal escape molecule, a subcellular targeting molecule, a nuclear targeting molecule, or a combination. One or more of the accessory molecules can be peptides. One or more of the peptides can be independently an RGD peptide, iRGD, LyP-1 peptide, NGR peptide, iNGR, RGR peptide, HER2 binding peptide, or a combination.

The amino acid sequence can be selected for homing to activated macrophages.

The AMT peptide can be comprised in an AMT composition. The AMT composition can comprise one or more accessory molecules. The AMT composition can comprise one or more cargo compositions. The AMT composition can comprise one or more peptides. The AMT peptide can be comprised in an AMT conjugate. The AMT conjugate can comprise one or more accessory molecules. The AMT conjugate can comprise one or more cargo compositions. The AMT conjugate can comprise one or more peptides.

The cell, tissue, or both can be exposed to a plurality of accessory molecules. The cell, tissue, or both can be exposed to a plurality of peptides. The cell, tissue, or both can be exposed to a plurality of cargo compositions. The cell, tissue, or both can be exposed to a plurality of AMT peptides. The cell, tissue, or both can be exposed to a plurality of co-compositions.

As used herein, "selecting an amino acid sequence for homing to activated macrophages" refers to selecting, identifying designing or otherwise categorizing an amino acid sequence with the specific intention of targeting to an activated macrophage of a protein or peptide that is comprised of the amino acid sequence. Thus, for example, selecting an amino acid sequence for some purpose or capability other than homing to activated macrophages of a protein or peptide that is comprised of the amino acid sequence and in the absence of an intention of homing to activated macrophages of a protein or peptide that is comprised of the amino acid sequence does not constitute "selecting an amino acid sequence for homing to activated macrophages." Selecting an amino acid sequence for some purpose or capability as well as for homing to activated macrophages of a protein or peptide that is comprised of the amino acid sequence does constitute "selecting an amino acid sequence for homing to activated macrophages." Thus, the presence of additional goals or purposes does not alter that selection of an amino acid sequence at least with the specific intention of homing to activated macrophages of a protein or peptide that is comprised of the amino acid sequence constitutes "selecting an amino acid sequence for homing to activated macrophages."

As used herein, unless the context indicates otherwise, "selecting a co-composition for homing to activated macrophages" refers to selecting, identifying designing or otherwise categorizing a co-composition and an AMT composition, AMT conjugate, AMT molecule, AMT protein, or AMT peptide with the specific intention of homing to activated macrophages of both the co-composition and the AMT composition, AMT conjugate, AMT molecule, AMT protein, or AMT peptide. Thus, for example, selecting a co-composition for some purpose or capability other than homing to activated macrophages in combination with entry of a selected AMT composition, AMT conjugate, AMT molecule, AMT protein, or AMT peptide and in the absence of an intention of homing to activated macrophages of both the co-composition and the AMT composition, AMT conjugate, AMT molecule, AMT protein, or AMT peptide does not constitute "selecting co-composition for homing to activated macrophages." Selecting a co-composition for some purpose or capability as well as for homing to activated macrophages of the co-composition does constitute "selecting co-composition for homing to activated macrophages." Thus, the presence of additional goals or purposes does not alter that selection of a co-composition at least with the specific intention of homing to activated macrophages of a co-composition constitutes "selecting a co-composition for homing to activated macrophages."

As used herein, unless the context indicates otherwise, "selecting a cargo composition for homing to activated macrophages" refers to selecting, identifying designing or otherwise categorizing a cargo composition and an AMT composition, AMT conjugate, AMT molecule, AMT protein, or AMT peptide with the specific intention of homing to activated macrophages of both the cargo composition and the AMT composition, AMT conjugate, AMT molecule, AMT protein, or AMT peptide. Thus, for example, selecting a cargo composition for some purpose or capability other than homing to activated macrophages in combination with entry of a selected AMT composition, AMT conjugate, AMT molecule, AMT protein, or AMT peptide and in the absence of an intention of homing to activated macrophages of both the cargo composition and the AMT composition, AMT conjugate, AMT molecule, AMT protein, or AMT peptide does not constitute "selecting cargo composition for homing to activated macrophages." Selecting a cargo composition for some purpose or capability as well as for homing to activated macrophages of the cargo composition does constitute "selecting cargo composition for homing to activated macrophages." Thus, the presence of additional goals or purposes does not alter that selection of a cargo composition at least with the specific intention of homing to activated macrophages of a cargo composition constitutes "selecting a cargo composition for homing to activated macrophages."

As used herein, "causing a compound or composition to be covalently coupled or directly non-covalently associated" with something else refers to any action that results in a compound or composition that is not covalently coupled or directly non-covalently associated with the something else becoming or coming into the state of being covalently coupled or directly non-covalently associated with the something else. As an example, covalently coupling an accessory molecule to an AMT peptide constitutes "causing an accessory molecule to be covalently coupled or directly non-covalently associated" with the AMT peptide. As another example, an AMT peptide that starts as a nonexistent concept and then is synthesized as part of a composition that includes the thing to which the AMT peptide is to be coupled or associated constitutes "causing an AMT peptide to be covalently coupled or directly non-covalently associated" with the thing. For example, synthesis of a peptide that includes both an amino acid sequence of interest and an amino acid sequence comprising a C-terminal element constitutes causing the amino acid sequence of interest to be covalently coupled or directly non-covalently associated with the amino acid sequence comprising a C-terminal element. However, and in general, synthesis of a protein or peptide that naturally includes both the amino acid sequence of interest and an amino acid sequence comprising a C-terminal element can be excluded as a process of "causing the amino acid sequence of interest to be covalently coupled or directly non-covalently associated" with the amino acid sequence comprising a C-terminal element.

As used herein, "causing a co-composition to be covalently coupled or directly non-covalently associated" with something else refers to any action that results in a co-composition that is not covalently coupled or directly non-covalently associated with the something else becoming or coming into the state of being covalently coupled or directly non-covalently associated with the something else. More clearly, "causing a co-composition to be covalently coupled or directly non-covalently associated" with something else refers to any action that results in a co-composition and the something else becoming or coming into the state of being covalently coupled or directly non-covalently associated. As an example, covalently coupling a co-composition to another co-composition constitutes "causing a co-composition to be covalently coupled or directly non-covalently associated" with the other co-composition. As another example, a co-composition that starts as a nonexistent concept and then is synthesized as part of a composition that includes the thing to which the co-composition is to be coupled or directly associated constitutes "causing a co-composition to be covalently coupled or directly non-covalently associated" with the thing.

As used herein, "causing a cargo composition to be covalently coupled or directly non-covalently associated" with something else refers to any action that results in a cargo composition that is not covalently coupled or directly non-covalently associated with the something else becoming or coming into the state of being covalently coupled or non-covalently associated with the something else. More clearly, "causing a cargo composition to be covalently coupled or directly non-covalently associated" with something else refers to any action that results in a cargo composition and the something else becoming or coming into the state of being covalently coupled or directly non-covalently associated. As an example, covalently coupling a cargo composition to another cargo composition constitutes "causing a cargo composition to be covalently coupled or directly non-covalently associated" with the other cargo composition. As another example, a cargo composition that starts as a nonexistent concept and then is synthesized as part of a composition that includes the thing to which the cargo composition is to be coupled or directly associated constitutes "causing a cargo composition to be covalently coupled or directly non-covalently associated" with the thing.

AMT peptides can be composed of, for example, amino acids, amino acid analogs, peptide analogs, amino acid mimetics, peptide mimetics, etc. Although structures, design, etc. of AMT peptides is described herein in terms of amino acids and peptides composed of amino acids for convenience, it is understood that analogous analogs, mimetics, modified forms, etc. of amino acids and peptides can also be used as AMT peptides and designed using similar principles.

Any component, such as the components disclosed herein, can overlap, be adjacent to, and/or be upstream, downstream, or both of a peptide, such as an AMT peptide. Examples of such components include accessory molecules, homing molecules, protease cleavage sites, etc. It is useful to have some components coupled to or associated with a peptide, such as an AMT peptide to be downstream (C-terminal) of the peptide. For example, activatable peptide having an accessory protein or a homing peptide downstream of the peptide (and thus downstream from the cleavage site for activation) will be separated from the peptide when it is activated. As another example, activatable peptides having an accessory molecule or a homing molecule downstream of the peptide (and thus downstream from the cleavage site for activation) will be separated from the peptide when it is activated. This can have some advantages such as making the peptide function more efficient or reducing the chance for extraneous effects of the eliminated component.

As used herein, "activatable peptide" refers to a peptide, such as a LyP-1 peptide, having a molecule, moiety, nanoparticle, compound or other composition covalently coupled to the peptide, such as to the terminal carboxyl group of the peptide, where the molecule, moiety, nanoparticle, compound or other composition can block the function of the peptide (such as an internalization and/or tissue penetration function) and where the molecule, moiety, nanoparticle, compound or other composition can be removed (to expose the terminal carboxy group of the peptide, for example). For example, the activatable peptide can be on the C-terminal end of the protein or peptide, and can prevent the peptide from being internalized and/or from penetrating tissue. The molecule, nanoparticle, moiety, compound or other composition covalently coupled to the peptide can be referred to as the "blocking group."

An activatable peptide can be blocked from internalization into a cell, from tissue penetration, or both. Generally, an activatable peptide will be blocked from both internalization into a cell and penetration of tissue. Such activatable peptides can be referred to as activatable internalization and penetrating peptides.

The cleavable bond of an activatable peptide, such as an activatable AMT peptide, can be cleaved in any suitable way. For example, the cleavable bond can be cleaved enzymatically or non-enzymatically. For enzymatic cleavage, the cleaving enzyme can be supplied or can be present at a site where the peptide is delivered, homes, travels or accumulates. For example, the enzyme can be present in proximity to a cell to which the peptide is delivered, homes, travels, or accumulates. For non-enzymatic cleavage, the peptide can be brought into contact with a cleaving agent, can be placed in cleaving conditions, or both. A cleaving agent is any substance that can mediate or stimulate cleavage of the cleavable bond. A non-enzymatic cleaving agent is any cleaving agent except enzymes. Cleaving conditions can be any solution or environmental conditions that can mediate or stimulate cleavage of the cleavable bond. For example, some labile bonds can be cleaved in acid conditions, alkaline conditions, in the presence of a reactive group, etc. Non-enzymatic cleaving conditions are any cleaving conditions except the presence of enzymes. Non-agent cleaving conditions are any cleaving conditions except the presence of cleaving agents.

Activatable peptides, such as an activatable AMT peptides, can be activatable in broad or narrow circumstances. Generally, activatable peptides are activatable relative to a specific agent or group of agents that can activate the peptides. Thus, for example, a particular activatable peptide may only be activatable by certain proteases. Such a peptide can be referred to as an activatable peptide but can also be referred to as being activatable by the particular proteases.

A "protease-activatable peptide" (or "protease-activated peptide") refers to an activatable peptide where the blocking group is coupled to the peptide via a peptide bond and where the peptide bond can be cleaved by a protease. Cleavage of this peptide bond in a protease-activatable peptide makes the peptide capable of a function, such as internalization into a cell and/or of tissue penetration.

"Internalization" refers to passage through a plasma membrane or other biological barrier. "Penetration" refers to passage into and through a cell, tissue, or other biological barrier. Penetration generally involves and includes internalization. The disclosed AMT peptides generally promote and allow internalization (such as internalization into a cell).

By "internalization into a cell" is meant that that a component is capable of penetrating or passing through the plasma membrane, thereby being internalized into the cell. This internalization can occur with, for example, 10, 20, 30, 40, 50, 60, 70, 80, 90, or 100% efficiency for a given component and a given cell. By "permeable" is meant the ability and/or condition of cells and/or tissues to allow compositions, conjugates, molecules, etc. in proximity to the cells and/or tissues to enter and or pass through the cells and/or tissues.

As used herein, "tissue penetration" and "penetration of tissue" refer to passage into or through a tissue beyond or through the outer or a first layer of cells or through a tissue membrane. Such passage or penetration through tissue (which can also be referred to as extravasation and tissue penetration) can be a function of, for example, cell internalization and passage between cells in the tissue.

Subjects harboring activated macrophages, can be identified as a candidate for RVL-based therapy by, for example, (a) exposing tissue from the subject to an AMT peptide; and (b) determining if the AMT peptide bound to the tissue, wherein binding to the tissue identifies the subject as being a candidate for RVL-based therapy. Any form or type of AMT peptide, AMT peptide, AMT protein, AMT conjugate, or AMT composition can be used in these methods.

The co-composition can be, for example, a nanoparticle, or a molecule, or complex of molecules with therapeutic or diagnostic applications. Therapeutic co-compositions that can be targeted with AMT peptides include but are not limited to a nanoparticle, a molecule, a complex of molecules, a pro-apototic agent, an immunomodulatory agent, a pro-inflammatory agent, an immunostimulating agent, an anti-inflammatory agent, an immunosuppressing agent, an anti-angiogenic agent, a pro-angiogenic agent, a cancer chemotherapeutic agent, an anti-bacterial agent, a cytotoxic agent, a pro-cell survival agent, a cell differentiating agent, a neuroprotective agent, an anti-arthritic agent, an anti-viral agent, or a combination of these. Therapeutic co-compositions that can be targeted with AMT peptides include but are not limited to a therapeutic protein, a therapeutic compound, a therapeutic composition, a pro-apototic agent, an immunomodulatory agent, a pro-inflammatory agent, an immunostimulating agent, an anti-inflammatory agent, an immunosuppressing agent, an anti-angiogenic agent, a pro-angiogenic agent, a cancer chemotherapeutic agent, a toxin, an anti-bacterial agent, a cytotoxic agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination. Diagnostic co-compositions that can be targeted with AMT peptides include but are not limited to a nanoparticle, a molecule, a complex of molecules, a MRI imaging agent, a radioimaging agent, an optical imaging agent, a molecular tag (such as biotin), a fluorophore, an epitope tag (that can, for example, be detected using a specific molecular assay), or a combination of these.

The cargo composition can be, for example, a nanoparticle, or a molecule, or complex of molecules with therapeutic or diagnostic applications. Therapeutic cargo compositions that can be targeted with AMT peptides include but are not limited to a nanoparticle, a molecule, a complex of molecules, a pro-apototic agent, an immunomodulatory agent, a pro-inflammatory agent, an immunostimulating agent, an anti-inflammatory agent, an immunosuppressing agent, an anti-angiogenic agent, a pro-angiogenic agent, a cancer chemotherapeutic agent, an anti-bacterial agent, a cytotoxic agent, a pro-cell survival agent, a cell differentiating agent, a neuroprotective agent, an anti-arthritic agent, an anti-viral agent, or a combination of these. Therapeutic cargo compositions that can be targeted with AMT peptides include but are not limited to a therapeutic protein, a therapeutic compound, a therapeutic composition, a pro-apoptotic agent, an immunomodulatory agent, a pro-inflammatory agent, an immunostimulating agent, an anti-inflammatory agent, an immunosuppressing agent, an anti-angiogenic agent, a pro-angiogenic agent, a cancer chemotherapeutic agent, a toxin, an anti-bacterial agent, a cytotoxic agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination. Diagnostic cargo compositions that can be targeted with AMT peptides include but are not limited to a nanoparticle, a molecule, a complex of molecules, a MRI imaging agent, a radioimaging agent, an optical imaging agent, a molecular tag (such as biotin), a fluorophore, an epitope tag (that can, for example, be detected using a specific molecular assay), or a combination of these.

The disclosed peptides can be in isolated form. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The AMT peptide can have a length of up to 10, 20, 30, 40, 50, 100, 150, 200, 250, 300, 400, 500, 1000 or 2000 residues. In particular embodiments, an AMT peptide can have a length of at least 7, 8, 9, 10, 15, 20, 25, 30, 40, 50, 60, 70, 80, 90, 100 or 200 residues. In further embodiments, an AMT peptide can have a length of 7 to 200 residues, 7 to 100 residues, 7 to 90 residues, 7 to 80 residues, 7 to 70 residues, 7 to 60 residues, 7 to 50 residues, 7 to 40 residues, 7 to 30 residues, 7 to 20 residues, 7 to 15 residues, 7 to 10 residues, 8 to 200 residues, 8 to 100 residues, 8 to 90 residues, 8 to 80 residues, 8 to 70 residues, 8 to 60 residues, 8 to 50 residues, 8 to 40 residues, 8 to 30 residues, 8 to 20 residues, 8 to 15 residues, 8 to 10 residues, 9 to 200 residues, 9 to 100 residues, 9 to 90 residues, 9 to 80 residues, 9 to 70 residues, 9 to 60 residues, 9 to 50 residues, 9 to 40 residues, 9 to 30 residues, 9 to 20 residues, 9 to 15 residues, 9 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

A protein or peptide containing an AMT peptide can have a length of up to 50, 100, 150, 200, 250, 300, 400, 500, 1000 or 2000 residues. In particular embodiments, the protein or peptide portion of an AMT composition can have a length of at least 10, 20, 30, 40, 50, 60, 70, 80, 90, 100 or 200 residues. In further embodiments, the protein or peptide containing an AMT peptide can have a length of 7 to 200 residues, 7 to 100 residues, 7 to 90 residues, 7 to 80 residues, 7 to 70 residues, 7 to 60 residues, 7 to 50 residues, 7 to 40 residues, 7 to 30 residues, 7 to 20 residues, 7 to 15 residues, 7 to 10 residues, 8 to 200 residues, 8 to 100 residues, 8 to 90 residues, 8 to 80 residues, 8 to 70 residues, 8 to 60 residues, 8 to 50 residues, 8 to 40 residues, 8 to 30 residues, 8 to 20 residues, 8 to 15 residues, 8 to 10 residues, 9 to 200 residues, 9 to 100 residues, 9 to 90 residues, 9 to 80 residues, 9 to 70 residues, 9 to 60 residues, 9 to 50 residues, 9 to 40 residues, 9 to 30 residues, 9 to 20 residues, 9 to 15 residues, 9 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

The AMT conjugate can have a length of up to 50, 100, 150, 200, 250, 300, 400, 500, 1000 or 2000 residues. In particular embodiments, an AMT conjugate can have a length of at least 10, 20, 30, 40, 50, 60, 70, 80, 90, 100 or 200 residues. In further embodiments, an AMT conjugate can have a length of 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

The protein or peptide portion of an AMT composition can have a length of up to 50, 100, 150, 200, 250, 300, 400, 500, 1000 or 2000 residues. In particular embodiments, the protein or peptide portion of an AMT composition can have a length of at least 10, 20, 30, 40, 50, 60, 70, 80, 90, 100 or 200 residues. In further embodiments, the protein or peptide portion of an AMT composition can have a length of 7 to 200 residues, 7 to 100 residues, 7 to 90 residues, 7 to 80 residues, 7 to 70 residues, 7 to 60 residues, 7 to 50 residues, 7 to 40 residues, 7 to 30 residues, 7 to 20 residues, 7 to 15 residues, 7 to 10 residues, 8 to 200 residues, 8 to 100 residues, 8 to 90 residues, 8 to 80 residues, 8 to 70 residues, 8 to 60 residues, 8 to 50 residues, 8 to 40 residues, 8 to 30 residues, 8 to 20 residues, 8 to 15 residues, 8 to 10 residues, 9 to 200 residues, 9 to 100 residues, 9 to 90 residues, 9 to 80 residues, 9 to 70 residues, 9 to 60 residues, 9 to 50 residues, 9 to 40 residues, 9 to 30 residues, 9 to 20 residues, 9 to 15 residues, 9 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

The AMT composition can have a length of up to 50, 100, 150, 200, 250, 300, 400, 500, 1000 or 2000 residues. In particular embodiments, an AMT composition can have a length of at least 10, 20, 30, 40, 50, 60, 70, 80, 90, 100 or 200 residues. In further embodiments, an AMT composition can have a length of 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

AMT (and other) peptides can be stabilized against proteolysis. For example, the stability and activity of peptides, such as tumor-homing peptides CREKA (Simberg et al., 2007), by protecting some of the peptide bonds with N-methylation or C-methylation. The most important bond to protect in order to enhance activity is the R-G bond because it would prevent a cleavage that would inactivate both the integrin-binding and AMT activities. Accessory peptides and homing peptides can also or similarly be stabilized against proteolysis.

The disclosed AMT peptides (and other AMT forms) and co-compositions can be administered together or separately; in the same form and manner or in different forms and/or manners; at the same time or at different times; with the AMT peptide (or other AMT form) administered first or second. Administration can be, for example, co-administration (at the same time and by the same or different route/means/form), separate administration (parallel administration by the same or different route/means/form), sequential administration (at different times by the same or different route/means/form), etc. When the co-composition and AMT peptide (or other AMT form) are administered at different times, a variety of different delays can be used between the administrations. For example, the AMT peptide (or other AMT form) can be administered 1, 2, 3, 4, 5, 6, 7, 8, 9, 10, 11, 12, 13, 15, 20, 30, 40, 45, 50, 60, 70, 80, 90, 100, 110, or 120 minutes or more before administering a co-composition. The AMT peptide (or other AMT form) can be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours or more before administering a co-composition. The AMT peptide (or other AMT form) can be administered 1, 2, 3, 4, 5, 6, or 7 days or more before administering a co-composition. The AMT peptide (or other AMT form) can be administered 1, 2, 3, 4, 5, 6, 7, 8, 9, 10, 11, 12, 13, 15, 20, 30, 40, 45, 50, 60, 70, 80, 90, 100, 110, or 120 minutes or more after administering a co-composition. The AMT peptide (or other AMT form) can be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours or more after administering a co-composition. The AMT peptide (or other AMT form) can be administered 1, 2, 3, 4, 5, 6, or 7 days or more after administering a co-composition.

The AMT peptide (or other AMT form) can be administered within 1, 2, 3, 4, 5, 6, 7, 8, 9, 10, 11, 12, 13, 15, 20, 30, 40, 45, 50, 60, 70, 80, 90, 100, 110, or 120 minutes before administering a co-composition. The AMT peptide (or other AMT form) can be administered within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours before administering a co-composition. The AMT peptide (or other AMT form) can be administered within 1, 2, 3, 4, 5, 6, or 7 days before administering a co-composition. The AMT peptide (or other AMT form) can be administered within 1, 2, 3, 4, 5, 6, 7, 8, 9, 10, 11, 12, 13, 15, 20, 30, 40, 45, 50, 60, 70, 80, 90, 100, 110, or 120 minutes after administering a co-composition. The AMT peptide (or other AMT form) can be administered within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours after administering a co-composition. The AMT peptide (or other AMT form) can be administered within 1, 2, 3, 4, 5, 6, or 7 days after administering a co-composition. Administration within the same day or hour is particularly useful.

The AMT composition, AMT conjugate, AMT molecule, AMT protein, or AMT peptide and the co-composition can be administered to the subject simultaneously. By simultaneously is meant during overlapping or contiguous time periods. The AMT composition, AMT conjugate, AMT molecule, AMT protein, or AMT peptide and the co-composition can be administered to the subject in a single composition comprising the AMT composition, AMT conjugate, AMT molecule, AMT protein, or AMT peptide and the co-composition. The AMT composition, AMT conjugate, AMT molecule, AMT protein, or AMT peptide and the co-composition can be administered to the subject in separate compositions. The AMT peptide and the co-composition can be administered to the subject at different times. The AMT peptide and the co-composition can be administered to the subject in separate compositions. By separate compositions is meant compositions that are not mixed or in contact with each other (except as may occur following administration). The AMT peptide and the co-composition can be administered to the subject by separate routes. By separate routes is meant in separate locations, by different means or mode, or both.

AMT peptides can be made in the form of stabilized peptides and/or formulated as long-circulating forms. For example, a polyethylene glycol conjugate can be used. AMT peptides and/or co-compositions can also be administered over a period of time. For example, AMT peptides and/or co-compositions can be delivered with an osmotic pump. This can extend the permeability of the target cells and tissues. Modified forms of AMT peptides can be used. For example, AMT peptides can be methylated (which can stabilize the peptides against proteolysis). Stability against cleavage is desirable, except for bonds to be cleaved to activate a peptide. Modifications to AMT peptides generally should leave them functional or capable of function after activation. A peptide with a structural difference from naturally occurring forms of peptides can be considered a modified peptide.

It is understood that there are numerous amino acid and peptide analogs which can be incorporated into the disclosed AMT compositions, conjugates, molecules, proteins, peptides, and elements. For example, there are numerous D amino acids or other non-natural amino acids which can be used. The opposite stereoisomers of naturally occurring peptides are disclosed, as well as the stereo isomers of peptide analogs. These amino acids can readily be incorporated into polypeptide chains by chemical synthesis or by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology &

Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—$CH$=$CH$— (cis and trans), —$COCH_2$—$CH(OH)CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CH H_2$—S); Hann J. Chem. Soc Perkin Trans. I 307-314 (1982) (—$CH$—$CH$—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—$CH(OH)CH_2$—); Holladay et al. Tetrahedron. Lett 24:4401-4404 (1983) (—$C(OH)CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides as long as activity is preserved. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Disclosed are polyfunctional AMT compositions which, in addition to the AMT peptide, contain, for example, an accessory peptide, an accessory peptide fused to the AMT peptide, an accessory molecule covalently coupled to or non-covalently associated with the AMT peptide, a cargo composition fused to the AMT peptide, and/or a cargo composition covalently coupled to or non-covalently associated with the AMT peptide. Additional compounds having separate functions can be added to the composition. Such polyfunctional conjugates have at least two functions conferred by different portions of the composition and can, for example, display anti-inflammatory activity or pro-apoptotic activity in addition to selective homing activity.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as that from which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

The disclosed peptides can be validated by, for example, testing in vitro macrophage binding, and in vivo homing. A peptide can be screened or tested for the binding and homing ability of AMT peptides by, for example, testing in vitro macrophage binding, and in vivo homing. For example, specific binding to activated macrophages can be tested by assessing binding of the peptide to an activated macrophage or an appropriate test cell or cell line. For example, specific binding to activated macrophages can be tested or assessed using cells of the cell lines J774A.1 and RAW264.7. Specificity of binding to the activated macrophage or appropriate test cell can be tested or assessed by comparing the binding observed in a control cell, such as a cell that is not an activated macrophage or an appropriate test cell. Preferably, such a control cell is a non-activated macrophage. Testing peptides for a lack of homing to activated macrophages in a non-human animal can also be sued as a control.

A peptide can be screened or tested for the by assessing homing to the target and effectively delivery of the cargo molecules in a non-human animal. Generally, the peptide can be tested as part of an AMT composition or AMT conjugate but with the test peptide used in place of the AMT peptide. A peptide useful as an AMT peptide can be identified, for example, when, in such a screen or test, the test composition homes to the target and effectively delivers the cargo molecules.

Synthetic peptides can be used to show that the activities associated with the selected phage are reproduced by the peptide the phage displays. Techniques for this are well known (e.g. Zhang et al., 2005; Simberg et al., 2007; Karmali et al., 2008). The peptides generally can be labeled with a fluorophore to allow detection in tissues, and both the free peptide and a multimeric conjugate on nanoparticles (which more closely resembles the multivalent presentation on phage) can be tested.

As used herein in reference to a peptide, the term "cyclic" means a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof.

A peptide also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (orn), α,β-diamino-propionic acid, γ-amino-adipic acid (Adp) and M-(aminomethyl)benzoic acid (Mamb). Cyclization additionally can be effected, for example, through the formation of a lysinonorleucine bond between lysine (Lys) and leucine (Leu) residues or a dityrosine bond between two tyrosine (Tyr) residues. The skilled person understands that these and other bonds can be included in a cyclic peptide.

A variety of peptides can be used in the disclosed compositions, conjugates and methods. Such peptides include, without limitation, AMT and CRV peptides as disclosed herein. The disclosed compounds, compositions, conjugates and methods can include or use the disclosed peptides in various forms, including AMT peptides and peptidomimetics as disclosed. For convenience of expression, in many places herein the use or inclusion of peptides will be recited. It is understood that, in such cases, it is considered that peptides in various forms can also be used or included in the same or similar ways as is described in terms of AMT peptides, and such use and inclusion is specifically contemplated and disclosed thereby.

By "selectively binds," in the context of a molecule that binds to a target molecule or component, is meant that the molecule binds preferentially to the target as compared to non-target. For example, the molecule can bind preferentially to a target receptor, as compared to other receptors and proteins. Selective binding to, for example, activated macrophages generally is characterized by at least a two-fold greater binding to activated macrophages, as compared to several tissue types of non-activated macrophages and other cells and tissues. A molecule can be characterized by, for example, 5-fold, 10-fold, 20-fold or more preferential binding to the target as compared to one or more non-targets. For example, a molecule can be characterized by, for example, 5-fold, 10-fold, 20-fold or more preferential binding to tumor associated macrophages as compared to several or many other non-activated macrophages, or as compared to all non-tumoral tissue. As another example, a molecule can be characterized by, for example, 5-fold, 10-fold, 20-fold or more preferential binding to activated macrophages as compared to non-activated macrophages, or as compared to-most or all other cells and tissues. Thus, it is understood that, in some cases, a molecule *binds, in part, to one or more non-targets in addition to binding to the target.

Binding of a molecule to a target via a component generally means that the component is bound to or a part of the target, that the molecule binds to the components, and that, thereby, the molecule is indirectly bound to or associated with the target.

The term "homing molecule" as used herein, means any molecule that selectively homes in vivo to specific cells or specific tissue in preference to normal tissue. Similarly, the term "homing peptide" or "homing peptidomimetic" means a peptide that selectively homes in vivo to specific cells or specific tissue in preference to normal tissue. It is understood that a homing molecule that selectively homes in vivo to specific cells or specific tissue or can exhibit preferential homing to specific cells or specific tissue. The disclosed AMT and CRV peptides are examples of homing molecules that home to activated macrophages.

By "selectively homes" is meant that, in vivo, the homing molecule binds preferentially to the target as compared to non-target. For example, the homing molecule can bind preferentially to activated macrophages, as compared to non-activated macrophages. Selective homing to, for example, activated macrophages generally is characterized by at least a two-fold greater localization around activated macrophages, as compared to several tissue types of non-activated macrophages and other cells and tissues. A homing molecule can be characterized by, for example, 5-fold, 10-fold, 20-fold or more preferential localization to the target as compared to one or more non-targets. For example, a homing molecule can be characterized by, for example, 5-fold, 10-fold, 20-fold or more preferential localization to tumor associated macrophages as compared to several or many other non-activated macrophages, or as compared to all non-tumoral tissue. As another example, a homing molecule can be characterized by, for example, 5-fold, 10-fold, 20-fold or more preferential localization to activated macrophages as compared to non-activated macrophages, or as compared to-most or all other cells and tissues. Thus, it is understood that, in some cases, a homing molecule homes, in part, to one or more normal organs in addition to homing to the target tissue. Selective homing can also be referred to as targeting. The molecules, proteins, cells, tissues, etc. that are targeted by homing molecules can be referred to as targeted molecules, proteins, cells, tissues, etc.

Binding in the context of a homing molecule recognizing and/or binding to its target can refer to both covalent and non-covalent binding, for example where a homing molecule can bind, attach or otherwise couple to its target by covalent and/or non-covalent binding. Binding can be either high affinity or low affinity, preferably high affinity. Examples of binding forces that can be useful include, but are not limited to, covalent bonds, dipole interactions, electrostatic forces, hydrogen bonds, hydrophobic interactions, ionic bonds, and/or van der Waals forces.

Surface molecules can be associated with and arranged in the compositions in a variety of configurations. In some forms, surface molecules can be associated with, conjugated to, and/or covalently coupled to a plurality of peptides, a plurality of cargo molecules, or both. In some forms, surface molecules can be associated with, conjugated to, and/or covalently coupled to a plurality of peptides, wherein the peptides can be associated with, conjugated to, and/or covalently coupled to a plurality of cargo molecules. In some forms, surface molecules can be associated with, conjugated to, and/or covalently coupled to a plurality of cargo molecules, wherein the cargo molecules can be associated with, conjugated to, and/or covalently coupled to a plurality of peptides. Combinations of these combinations can also be used.

The surface molecules, alternatively referred to as a surface particles, disclosed herein can be conjugated with peptides and cargo molecules in such a way that the composition is delivered to a target. The surface molecule can be any substance that can be used with the peptides and cargo molecules, and is not restricted by size or substance. Examples include, but are not limited to, nanoparticles (such as iron oxide nanoparticles or albumin nanoparticles), liposomes, small organic molecules, microparticles, or microbubbles, such as fluorocarbon microbubbles. The term surface molecule is used to identify a component of the disclosed composition but is not intended to be limiting. In particular, the disclosed surface molecules are not limited to substances, compounds, compositions, particles or other materials composed of a single molecule. Rather, the disclosed surface molecules are any substance(s), compound(s), composition(s), particle(s) and/or other material(s) that can be conjugated with a plurality of peptides and cargo molecules such that at least some of the peptides and/or cargo molecules are presented and/or accessible on the surface of the surface molecule. A variety of examples of suitable surface molecules are described and disclosed herein.

The surface molecule can be detectable, or can be a therapeutic agent such as an agent that affects or regulates macrophages. In some forms, the therapeutic agent inhibits expression of the phosphotidylinositide 3-kinase (PI3K) gamma gene. In some forms, the therapeutic agent inhibits PI3K gamma. In some forms, the therapeutic agent can be a PI3K gamma inhibitor (such as TG100-115), and TNF-alpha. The section herein which discusses cargo molecules and moieties that can be detectable or therapeutic also applies to the surface molecule.

The term "nanoparticle" refers to a nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, nanoworms, fullerene-like materials, inorganic nanotubes, dendrimers (such as with covalently attached metal chelates), nanofibers, nanohoms, nanoonions, nanorods, nanoropes and quantum dots. A nanoparticle can produce a detectable signal, for example, through absorption and/or emission of photons (including radio frequency and visible photons) and plasmon resonance.

Microspheres (or microbubbles) can also be used with the methods disclosed herein. Microspheres containing chromophores have been utilized in an extensive variety of applications, including photonic crystals, biological labeling, and flow visualization in microfluidic channels. See, for example, Y. Lin, et al., Appl. Phys Lett. 2002, 81, 3134; D. Wang, et al., Chem. Mater. 2003, 15, 2724; X. Gao, et al., J. Biomed. Opt. 2002, 7, 532; M. Han, et al., Nature Biotechnology. 2001, 19, 631; V. M. Pai, et al., Mag. & Magnetic Mater. 1999, 194, 262, each of which is incorporated by reference in its entirety. Both the photostability of the chromophores and the monodispersity of the microspheres can be important.

Nanoparticles, such as, for example, metal nanoparticles, metal oxide nanoparticles, or semiconductor nanocrystals can be incorporated into microspheres. The optical, magnetic, and electronic properties of the nanoparticles can allow them to be observed while associated with the microspheres and can allow the microspheres to be identified and spatially monitored. For example, the high photostability, good fluorescence efficiency and wide emission tunability of colloidally synthesized semiconductor nanocrystals can make them an excellent choice of chromophore. Unlike organic dyes, nanocrystals that emit different colors (i.e. different wavelengths) can be excited simultaneously with a single light source. Colloidally synthesized semiconductor nanocrystals (such as, for example, core-shell CdSe/ZnS and CdS/ZnS nanocrystals) can be incorporated into microspheres. The microspheres can be monodisperse silica microspheres.

The nanoparticle can be a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897,945 and 6,759,199, each of which is incorporated by reference in its entirety.

The nanoparticles can be comprised of cargo molecules and a carrier protein (such as albumin). Such nanoparticles are useful, for example, to deliver hydrophobic or poorly soluble compounds. Nanoparticles of poorly water soluble drugs (such as taxane) have been disclosed in, for example, U.S. Pat. Nos. 5,916,596; 6,506,405; and 6,537,579 and also in U.S. Pat. Pub. No. 2005/0004002A1.

In forms, the nanoparticles can have an average or mean diameter of no greater than about 1000 nanometers (nm), such as no greater than about any of 900, 800, 700, 600, 500, 400, 300, 200, and 100 nm. In some forms, the average or mean diameters of the nanoparticles can be no greater than about 200 nm. In some forms, the average or mean diameters of the nanoparticles can be no greater than about 150 nm. In some forms, the average or mean diameters of the nanoparticles can be no greater than about 100 nm. In some forms, the average or mean diameter of the nanoparticles can be about 20 to about 400 nm. In some forms, the average or mean diameter of the nanoparticles can be about 40 to about 200 nm. In some embodiments, the nanoparticles are sterile-filterable.

The nanoparticles can be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

Examples of suitable carrier proteins include proteins normally found in blood or plasma, which include, but are not limited to, albumin, immunoglobulin including IgA, lipoproteins, apolipoprotein B, alpha-acid glycoprotein, beta-2-macroglobulin, thyroglobulin, transferin, fibronectin, factor VII, factor VIII, factor IX, factor X, and the like. In some embodiments, the carrier protein is non-blood protein, such as casein, alpha-lactalbumin, and beta-lactoglobulin. The carrier proteins may either be natural in origin or synthetically prepared. In some embodiments, the pharmaceutically acceptable carrier comprises albumin, such as human serum albumin. Human serum albumin (HSA) is a highly soluble globular protein of $M_r$ 65 K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, JAMA 237:355-360, 460-463 (1977)) and Houser et al., Surgery, Gynecology and Obstetrics, 150:811-816 (1980)) and in conjunction with exchange transfusion in the treatment of neonatal hyperbilirubinemia (see, e.g., Finlayson, Seminars in Thrombosis and Hemostasis, 6:85-120 (1980)). Other albumins are contemplated, such as bovine serum albumin Use of such non-human albumins could be appropriate, for example, in the context of use of these compositions in non-human mammals, such as the veterinary (including domestic pets and agricultural context).

Carrier proteins (such as albumin) in the composition generally serve as a carrier for the hydrophobic cargo molecules, i.e., the carrier protein in the composition makes the cargo molecules more readily suspendable in an aqueous medium or helps maintain the suspension as compared to compositions not comprising a carrier protein. This can avoid the use of toxic solvents (or surfactants) for solubilizing the cargo molecules, and thereby can reduce one or more side effects of administration of the cargo molecules into an individual (such as a human). Thus, in some embodiments, the composition described herein can be substantially free (such as free) of surfactants, such as Cremophor (including Cremophor EL® (BASF)). In some embodiments, the composition can be substantially free (such as free) of surfactants. A composition is "substantially free of Cremophor" or "substantially free of surfactant" if the amount of Cremophor or surfactant in the composition is not sufficient to cause one or more side effect(s) in an individual when the composition is administered to the individual.

The amount of carrier protein in the composition described herein will vary depending on other components in the composition. In some embodiments, the composition, co-composition, cargo composition, and/or AMT composition can comprise a carrier protein in an amount that is sufficient to stabilize the cargo molecules in an aqueous suspension, for example, in the form of a stable colloidal suspension (such as a stable suspension of nanoparticles). In some embodiments, the carrier protein is in an amount that reduces the sedimentation rate of the cargo molecules in an aqueous medium. For particle-containing compositions, the amount of the carrier protein also depends on the size and density of nanoparticles of the cargo molecules.

Methods of making nanoparticle compositions are known in the art. For example, nanoparticles containing cargo molecules and carrier protein (such as albumin) can be prepared under conditions of high shear forces (e.g., sonication, high pressure homogenization, or the like). These methods are disclosed in, for example, U.S. Pat. Nos. 5,916,596; 6,506,405; and 6,537,579 and also in U.S. Pat. Pub. No. 2005/0004002A1.

Briefly, the hydrophobic carrier molecules can be dissolved in an organic solvent, and the solution can be added to a human serum albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride and chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

The nanoparticle can also be, for example, a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Targeting molecules can be attached to the disclosed compositions and/or carriers. For example, the targeting molecules can be antibodies or fragments thereof, ligands for specific receptors, or other proteins specifically binding to the surface of the cells to be targeted.

"Liposome" as the term is used herein refers to a structure comprising an outer lipid bi- or multi-layer membrane surrounding an internal aqueous space. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 μm. These MLVs were first described by Bangham, et al., J Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilamnellar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 μm. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., Biochim et Biophys Acta 298:1015-1019 (1973) and the ether injection technique of Deamer, et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. I, Chapter 7, pg. 79-107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., Biochim et Biophys Acta 728:339-348 (1983), these multivesicular liposomes are spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles, having a diameter of 2-15 μm, are described in Callo, et al., Cryobiology 22(3):251-267 (1985).

Mezei, et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. I, II & III (1984). This and the aforementioned references describing various lipid vesicles suitable for use in the invention are incorporated herein by reference.

"Micelle" as used herein refers to a structure comprising an outer lipid monolayer. Micelles can be formed in an aqueous medium when the Critical Micelle Concentration (CMC) is exceeded. Small micelles in dilute solution at approximately the critical micelle concentration (CMC) are generally believed to be spherical. However, under other conditions, they may be in the shape of distorted spheres, disks, rods, lamellae, and the like. Micelles formed from relatively low molecular weight amphiphile molecules can have a high CMC so that the formed micelles dissociate rather rapidly upon dilution. If this is undesired, amphiphile molecules with large hydrophobic regions can be used. For example, lipids with a long fatty acid chain or two fatty acid chains, such as phospholipids and sphingolipids, or polymers, specifically block copolymers, can be used.

Polymeric micelles have been prepared that exhibit CMCs as low as $10^{-6}$ M (molar). Thus, they tend to be very stable while at the same time showing the same beneficial characteristics as amphiphile micelles. Any micelle-forming polymer presently known in the art or as such may become known in the future may be used in the disclosed compositions and methods. Examples of micelle-forming polymers include, without limitation, methoxy poly(ethylene glycol)-b-poly(ε-caprolactone), conjugates of poly(ethylene glycol) with phosphatidyl-ethanolamine, poly(ethylene glycol)-b-polyesters, poly(ethylene glycol)-b-poly(L-aminoacids), poly(N-vinylpyrrolidone)-bl-poly(orthoesters), poly(N-vinylpyrrolidone)-b-polyanhydrides and poly(N-vinylpyrrolidone)-b-poly(alkyl acrylates).

Micelles can be produced by processes conventional in the art. Examples of such are described in, for example, Liggins (Liggins, R. T. and Burt, H. M., "Polyether-polyester diblock copolymers for the preparation of paclitaxel loaded polymeric micelle formulations." Adv. Drug Del. Rev. 54: 191-202, (2002)); Zhang, et al. (Zhang, X. et al., "Development of amphiphilic diblock copolymers as micellar carriers of taxol." Int. J. Pharm. 132: 195-206, (1996)); and Churchill (Churchill, J. R., and Hutchinson, F. G., "Biodegradable amphipathic copolymers." U.S. Pat. No. 4,745,160, (1988)). In one such method, polyether-polyester block copolymers, which are amphipathic polymers having hydrophilic (polyether) and hydrophobic (polyester) segments, are used as micelle forming carriers.

Another type of micelle can be formed using, for example, AB-type block copolymers having both hydrophilic and hydrophobic segments, as described in, for example, Tuzar (Tuzar, Z. and Kratochvil, P., "Block and graft copolymer micelles in solution.", Adv. Colloid Interface Sci. 6:201-232, (1976)); and Wilhelm, et al. (Wilhelm, M. et al., "Poly(styrene-ethylene oxide) block copolymer micelle formation in water: a fluorescence probe study.", Macromolecules 24: 1033-1040 (1991)). These polymeric micelles are able to maintain satisfactory aqueous stability. These micelles, in the range of approximately <200 nm in size, are effective in reducing non-selective RES scavenging and show enhanced permeability and retention.

Further, U.S. Pat. No. 5,929,177 to Kataoka, et al. describes a polymeric molecule which is usable as, inter alia, a drug delivery carrier. The micelle is formed from a block copolymer having functional groups on both of its ends and which comprises hydrophilic/hydrophobic segments. The polymer functional groups on the ends of the block copolymer include amino, carboxyl and mercapto groups on the .alpha.-terminal and hydroxyl, carboxyl group, aldehyde group and vinyl group on the .omega.-terminal. The hydrophilic segment comprises polyethylene oxide, while the hydrophobic segment is derived from lactide, lactone or (meth)acrylic acid ester.

Further, for example, poly(D,L-lactide)-b-methoxypolyethylene glycol (MePEG:PDLLA) diblock copolymers can be made using MePEG 1900 and 5000. The reaction can be allowed to proceed for 3 hr at 160° C., using stannous octoate (0.25%) as a catalyst. However, a temperature as low as 130° C. can be used if the reaction is allowed to proceed for about 6 hr, or a temperature as high as 190° C. can be used if the reaction is carried out for only about 2 hr.

As another example, N-isopropylacrylamide ("IPAAm") (Kohjin, Tokyo, Japan) and dimethylacrylamide ("DMAAm") (Wako Pure Chemicals, Tokyo, Japan) can be used to make hydroxyl-terminated poly(IPAAm-co-DMAAm) in a radical polymerization process, using the method of Kohori, F. et al. (1998). (Kohori, F. et al., "Preparation and characterization of thermally Responsive block copolymer micelles comprising poly(N-isopropylacrylamide-b-D,L-lactide)." J. Control. Rel. 55: 87-98, (1998)). The obtained copolymer can be dissolved in cold water and filtered through two ultrafiltration membranes with a 10,000 and 20,000 molecular weight cut-off. The polymer solution is first filtered through a 20,000 molecular weight cut-off membrane. Then the filtrate was filtered again through a 10,000 molecular weight cut-off membrane. Three molecular weight fractions can be obtained as a result, a low molecular weight, a middle molecular weight, and a high molecular weight fraction. A block copolymer can then be synthesized by a ring opening polymerization of D,L-lactide from the terminal hydroxyl group of the poly(IPAAm-co-DMAAm) of the middle molecular weight fraction. The resulting poly(IPAAm-co-DMAAm)-b-poly(D,L-lactide) copolymer can be purified as described in Kohori, F. et al. (1999). (Kohori, F. et al., "Control of adriamycin cytotoxic activity using thermally responsive polymeric micelles composed of poly(N-isopropylacrylamide-co-N,N-dimethylacrylamide)-b-poly(D,L-lacide).—", Colloids Surfaces B: Biointerfaces 16: 195-205, (1999)).

Examples of block copolymers from which micelles can be prepared which can be used to coat a support surface are found in U.S. Pat. No. 5,925,720, to Kataoka, et al., U.S. Pat. No. 5,412,072 to Sakarai, et al., U.S. Pat. No. 5,410,016 to Kataoka, et al., U.S. Pat. No. 5,929,177 to Kataoka, et al., U.S. Pat. No. 5,693,751 to Sakurai, et al., U.S. Pat. No. 5,449,513 to Yokoyama, et al., WO 96/32434, WO 96/33233 and WO 97/0623, the contents of all of which are incorporated by reference. Modifications thereof which are prepared by introducing thereon a suitable functional group (including an ethyleneically unsaturated polymerizable group) are also examples of block copolymers from which micelles of the present invention are preferably prepared. Preferable block copolymers are those disclosed in the above-mentioned patents and or international patent publications. If the block copolymer has a sugar residue on one end of the hydrophilic polymer segment, as in the block copolymer of WO 96/32434, the sugar residue should preferably be subjected to Malaprade oxidation so that a corresponding aldehyde group may be formed.

Lipids are synthetically or naturally-occurring molecules which includes fats, waxes, sterols, prenol lipids, fat-soluble vitamins (such as vitamins A, D, E and K), glycerolipids, monoglycerides, diglycerides, triglycerides, glycerophospholipids, sphingolipids, phospholipids, fatty acids monoglycerides, saccharolipids and others. Lipids can be hydrophobic or amphiphilic small molecules; the amphiphilic nature of some lipids allows them to form structures such as monolayers, vesicles, micelles, liposomes, bi-layers or membranes in an appropriate environment i.e. aqueous environment. Any of a number of lipids can be used as amphiphile molecules, including amphipathic, neutral, cationic, and anionic lipids. Such lipids can be used alone or in combination, and can also include bilayer stabilizing components such as polyamide oligomers (see, e.g., U.S. Pat. No. 6,320,017, "Polyamide Oligomers", by Ansell), peptides, proteins, detergents, lipid-derivatives, such as PEG coupled to phosphatidylethanolamine and PEG conjugated to ceramides (see, U.S. Pat. No. 5,885,613). In a preferred embodiment, cloaking agents, which reduce elimination of liposomes by the host immune system, can also be included, such as polyamide-oligomer conjugates, e.g., ATTA-lipids, (see, U.S. patent application Ser. No. 08/996,783, filed Feb. 2, 1998) and PEG-lipid conjugates (see, U.S. Pat. Nos. 5,820,873, 5,534,499 and 5,885,613).

Any of a number of neutral lipids can be included, referring to any of a number of lipid species which exist either in an uncharged or neutral zwitterionic form at physiological pH, including diacylphosphatidylcholine, diacylphosphatidylethanolamine, ceramide, sphingomyelin, cephalin, cholesterol, cerebrosides, and diacylglycerols.

Cationic lipids, carry a net positive charge at physiological pH, can readily be used as amphiphile molecules. Such lipids include, but are not limited to, N,N-dioleyl-N,N-dimethylammonium chloride ("DODAC"); N-(2,3-dioleyloxy) propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3.beta.-(N—(N',N-dimethylaminoethane)-carbamoyl)cholesterol ("DC-Chol"), N-(1-(2,3-dioleyloxy)propyl)-N-2-(sperminecarboxamido) ethyl)-N,N-dimethyl-ammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as LIPOFECTIN (including DOTMA and DOPE, available from GIBCO/BRL), LIPOFECTAMINE (comprising DOSPA and DOPE, available from GIBCO/BRL), and TRANSFECTAM (comprising DOGS, in ethanol, from Promega Corp.).

Anionic lipids can be used as amphiphile molecules and include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

Amphipathic lipids can also be suitable amphiphile molecules. "Amphipathic lipids" refer to any suitable material, wherein the hydrophobic portion of the lipid material orients into a hydrophobic phase, while the hydrophilic portion orients toward the aqueous phase. Such compounds include, but are not limited to, fatty acids, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lyso-phosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and O-acyloxyacids, can also be used. Additionally, such amphipathic lipids can be readily mixed with other lipids, such as triglycerides and sterols. Zwitterionic lipids are a form of amphipathic lipid.

Sphingolipids are fatty acids conjugated to the aliphatic amino alcohol sphingosine. The fatty acid can be covalently bond to sphingosine via an amide bond. Any amino acid as described above can be covalently bond to sphingosine to form a sphingolipid. A sphingolipid can be further modified by covalent bonding through the α-hydroxyl group. The modification can include alkyl groups, alkenyl groups, alkynyl groups, aromatic groups, heteroaromatic groups, cyclyl groups, heterocyclyl groups, phosphonic acid groups. Non-limiting examples of shingolipids are N-acylsphingosine, N-Acylsphingomyelin, Forssman antigen.

Saccharolipids are compounds that contain both fatty acids and sugars. The fatty acids are covalently bonded to a sugar backbone. The sugar backbone can contain one or more sugars. The fatty acids can bond to the sugars via either amide or ester bonds. The sugar can be any sugar base. The fatty acid can be any fatty acid as described elsewhere herein. The provided compositions can comprise either natural or synthetic saccharolipids. Non-limiting saccharolipids are UDP-3-O-(β-hydroxymyristoyl)-GlcNAc, lipid IV A, Kdo2-lipid A.

The disclosed compositions, co-compositions, cargo compositions, and AMT compositions can include one or more cargo molecules. Generally, the disclosed compositions can include a plurality of cargo molecules. The disclosed compositions can include a single type of cargo molecule or a plurality of different types of cargo molecules. Thus, for example, the disclosed compositions can include a plurality of different types of cargo molecules where a plurality of one or more of the different types of cargo molecules can be present.

Cargo molecules can be any compound, molecule, conjugate, composition, etc. that is desired to be delivered using the disclosed compositions. For example, the cargo molecules can be therapeutic agents, detectable agents, or a combination. For example, the cargo molecules can be pro-apototic molecules, immunomodulatory molecules, pro-inflammatory molecules, immunostimulating molecules, anti-inflammatory molecules, immunosuppressing molecules, pro-apoptotic molecules, pore-generating molecules, antimicrobial molecules, mitochondria-affecting molecules, mitochondria-targeted molecules, or a combination. Examples of some useful cargo molecules are described below and elsewhere herein. In some forms, the therapeutic agent inhibits expression of the phosphotidylinositide 3-kinase (PI3K) gamma gene. In some forms, the therapeutic agent inhibits PI3K gamma. In some forms, the therapeutic agent can be a PI3K gamma inhibitor (such as TG100-115), and TNF-alpha.

Cargo molecules can be associated with and arranged in the compositions in a variety of configurations. In some forms, cargo molecules can be associated with, conjugated to, and/or covalently coupled to a plurality of surface molecules. In some forms, cargo molecules can be associated with, conjugated to, and/or covalently coupled to a plurality of peptides. In some forms, cargo molecules can be associated with, conjugated to, and/or covalently coupled to a plurality of peptides, wherein the peptides can be associated with, conjugated to, and/or covalently coupled to a plurality of surface molecules. Combinations of these combinations can also be used.

Membrane perturbing molecules include molecules that can disrupt membranes, that can form pores in membranes, that can make membranes leaky, that can be targeted to or affect intracellular membranes or organelles, such mitochondria or lysosomes. Some forms of membrane perturbing molecules can be pro-apoptotic while others can be non-apoptotic. Some forms of membrane perturbing molecules can be pro-apoptotic for only some types of cells.

In some forms, the composition can further comprise a surface molecule and a plurality of membrane perturbing molecules. In some forms, one or more of the membrane perturbing molecules can comprise the amino acid sequence $_D$(KLAKLAK)$_2$ (SEQ ID NO:3) or a conservative variant thereof, (KLAKLAK)$_2$ (SEQ ID NO:3) or a conservative variant thereof, (KLAKKLA)$_2$ (SEQ ID NO:5) or a conservative variant thereof, (KAAKKAA)$_2$ (SEQ ID NO:6) or a conservative variant thereof, or (KLGKKLG)$_3$ (SEQ ID NO:7) or a conservative variant thereof, or a combination. In some forms, one or more of the membrane perturbing molecules can comprise the amino acid sequence $_D$(KLAKLAK)$_2$ (SEQ ID NO:3), (KLAKLAK)$_2$ (SEQ ID NO:3), (KLAKKLA)$_2$ (SEQ ID NO:5), (KAAKKAA)$_2$ (SEQ ID NO:6), or (KLGKKLG)$_3$ (SEQ ID NO:7), or a combination. In some forms, one or more of the membrane perturbing molecules can comprise the amino acid sequence $_D$(KLAKLAK)$_2$ (SEQ ID NO:3) or a conservative variant thereof. In some forms, one or more of the membrane perturbing molecules can comprise the amino acid sequence $_D$(KLAKLAK)$_2$ (SEQ ID NO:3).

A plurality of modified and/or unmodified membrane perturbing molecules can each be independently selected from, for example, an amino acid segment comprising a modified or unmodified form of the amino acid sequence of a homing peptide, an amino acid segment comprising a modified or unmodified form of the amino acid sequence $_D$(KLAKLAK)$_2$ (SEQ ID NO:3), (KLAKLAK)$_2$ (SEQ ID NO:3), (KLAKKLA)$_2$ (SEQ ID NO:5), (KAAKKAA)$_2$ (SEQ ID NO:6), (KLGKKLG)$_3$ (SEQ ID NO:7), or a combination. A plurality of the membrane perturbing molecules can each independently comprise an amino acid segment comprising a modified or unmodified form of the amino acid sequence of a homing peptide.

The composition, co-composition, cargo composition, and/or AMT composition can comprise a sufficient number and composition of membrane perturbing molecules (modified or not) such that the composition has a membrane perturbing effect on the target. In one example, sufficiency of the number and composition of modified and/or unmodified membrane perturbing molecules can be determined by assessing membrane disruption, apoptosis, and/or therapeutic effect on the target.

The composition, co-composition, cargo composition, and/or AMT composition can comprise any number of modified and/or unmodified membrane perturbing molecules. By way of example, the composition, co-composition, cargo composition, and/or AMT composition can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more modified and/or unmodified membrane perturbing molecules. The composition can also comprise any number in between those numbers listed above.

Membrane perturbing molecules can be associated with and arranged in the compositions in a variety of configurations. In some forms, membrane perturbing molecules can be associated with, conjugated to, and/or covalently coupled to a plurality of surface molecules. In some forms, membrane perturbing molecules can be associated with, conjugated to, and/or covalently coupled to a plurality of homing molecules. In some forms, membrane perturbing molecules can be associated with, conjugated to, and/or covalently coupled to a plurality of homing molecules, wherein the homing molecules can be associated with, conjugated to, and/or covalently coupled to a plurality of surface molecules. Combinations of these combinations can also be used.

The disclosed membrane perturbing molecules can include modified forms of membrane perturbing molecules. The membrane perturbing molecules can have any useful modification. For example, some modifications can stabilize the membrane perturbing molecule. For example, the disclosed membrane perturbing molecules include methylated membrane perturbing molecules. Methylated membrane perturbing molecules are particularly useful when the membrane perturbing molecule includes a protein, peptide or amino acid segment. For example, a membrane perturbing molecule can be a modified membrane perturbing molecule, where, for example, the modified membrane perturbing molecule includes a modified amino acid segment or amino acid sequence. For example, a modified membrane perturbing molecule can be a methylated membrane perturbing molecule, where, for example, the methylated membrane perturbing molecule includes a methylated amino acid segment or amino acid sequence. Other modifications can be used, either alone or in combination. Where the membrane perturbing molecule is, or includes, a protein, peptide, amino acid segment and/or amino acid sequences, the modification can be to the protein, peptide, amino acid segment, amino acid sequences and/or any amino acids in the protein, peptide, amino acid segment and/or amino acid sequences Amino acid and peptide modifications are known to those of skill in the art, some of which are described below and elsewhere herein. Methylation is a particularly useful modification for the disclosed membrane perturbing molecules. Using modified forms of membrane perturbing molecules can increase their effectiveness.

The disclosed compositions, surface molecules, cargo molecules, peptides, proteins, amino acid sequences, etc. can comprise one or more internalization elements, tissue penetration elements, or both. Internalization elements and tissue penetration elements can be incorporated into or fused with other peptide components of the composition, such as peptide homing molecules and peptide cargo molecules.

Internalization elements are molecules, often peptides or amino acid sequences, that allow the internalization element and components with which it is associated, to pass through biological membranes. Tissue penetration elements are molecules, often peptides or amino acid sequences, that allow the tissue penetration element and components with which it is associated to passage into and through tissue. Some molecules, such as AMT peptides and CendR elements, function as both internalization elements and tissue penetration elements.

Internalization elements include, for example, cell-penetrating peptides (CPPs) and CendR elements. Peptides that are internalized into cells are commonly referred to as cell-penetrating peptides. There are two main classes of such peptides: hydrophobic and cationic (Zorko and Langel, 2005). The cationic peptides, which are commonly used to introduce nucleic acids, proteins into cells, include the prototypic cell-penetrating peptides (CPP), Tat, and penetratin (Derossi et al., 1998; Meade and Dowdy, 2007). A herpes virus protein, VP22, is capable of both entering and exiting cells and carrying a payload with it (Elliott and O'Hare, 1997; Brewis et al., 2003).

Association of the components of the disclosed compositions can be aided or accomplished via molecules, conjugates and/or compositions. Where such molecules, conjugates and/or compositions are other than AMT peptides, surface molecules, homing molecules, accessory molecules, co-compositions, cargo compositions, or cargo molecules (such as membrane perturbing molecules, internalization elements, tissue penetration elements, and moieties), they can be referred to herein as linkers. Such linkers can be any molecule, conjugate, composition, etc. that can be used to associate components of the disclosed compositions. Generally, linkers can be used to associate components other than surface molecules to surface molecules. Useful linkers include materials that are biocompatible, have low bioactivity, have low antigenicity, etc. That is, such useful linker materials can serve the linking/association function without adding unwanted bioreactivity to the disclosed compositions. Many such materials are known and used for similar linking and association functions. Polymer materials are a particularly useful form of linker material. For example, polyethylene glycols can be used.

Linkers are useful for achieving useful numbers and densities of the components (such as peptides and accessory molecules) on surface molecules. For example, linkers of fibrous form are useful for increasing the number of components per surface molecule or per a given area of the surface molecule. Similarly, linkers having a branching form are useful for increasing the number of components per surface molecule or per a given area of the surface molecule. Linkers can also have a branching fibrous form.

Sufficiency of the number and composition of peptides in the composition can be determined by assessing homing to the target and effectively delivery of the cargo molecules in a non-human animal. The composition, co-composition, cargo composition, and/or AMT composition can comprise a sufficient number and composition of peptides (modified or not) such that the composition homes to the target and effectively delivers the cargo molecules. In one example, sufficiency of the number and composition of modified and/or unmodified peptides can be determined by assessing cargo delivery and/or therapeutic effect on the target.

The composition, co-composition, cargo composition, and/or AMT composition can comprise a sufficient density and composition of peptides such that the composition homes to the target and effectively delivers the cargo molecules. Sufficiency of the density and composition of peptides can be determined by assessing cargo delivery and/or therapeutic effect on the target in a non-human animal.

The density of peptides on a surface molecule can be described in any suitable manner. For example, the density can be expressed as the number of peptides per, for example, a given area, surface area, volume, unit, subunit, arm, etc. of the surface molecule. The density can also be relative to, for example, the area, surface area, volume, unit, subunit, arm, etc. of the entire surface molecule or to the area, surface area, volume, unit, subunit, arm, etc. of a portion of the surface molecule. For example, a sufficient density of peptide can be present in a portion of the surface molecule. Thus, a composition having a sufficient density of peptides can have a threshold density (or above) for the entire surface molecule or for just one or more portions of the surface molecule. Unless otherwise stated, densities refer to average density over the designated portion of the surface molecule. For example, a density of 1 peptide per square nM of the surface molecule refers to an average density of the peptides over the entire surface molecule. As another example, a density of 1 peptide per square nM of a portion of the surface molecule refers to an average density of the peptides over just that portion of the surface molecule.

The density can be measured or calculated in any suitable manner. For example, the number or amount of peptides present on a surface molecule or group of surface molecules can be measured by, for example, detecting the level or intensity of signal produced by labeled peptides and calculating the density based on the structural characteristics of the surface molecule.

The density or threshold density of peptides can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 peptides per square nM of the entire or a portion of the surface molecule. The composition can also comprise any density in between those densities listed above.

The density or threshold density of peptides can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 peptides per square μM of the entire or a portion of the surface molecule. The composition can also comprise any density in between those densities listed above.

The density or threshold density of peptides can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 peptides per cubic nM of the entire or a portion of the surface molecule. The composition can also comprise any density in between those densities listed above.

The density or threshold density of peptides can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 peptides per cubic µM of the entire or a portion of the surface molecule. The composition can also comprise any density in between those densities listed above.

Such density measures and considerations can be applied as well to any of the components of the disclosed compositions other than the peptides.

The number of peptides on a surface molecule can be described in any suitable manner. For example, the number can be expressed as the number of peptides per, for example, a given area, surface area, volume, unit, subunit, arm, etc. of the surface molecule. The number can also be relative to, for example, the area, surface area, volume, unit, subunit, arm, etc. of the entire surface molecule or to the area, surface area, volume, unit, subunit, arm, etc. of a portion of the surface molecule. For example, a sufficient number of peptide can be present in a portion of the surface molecule. Thus, a composition having a sufficient number of peptides can have a threshold number (or above) for the entire surface molecule or for just one or more portions of the surface molecule.

The number can be measured or calculated in any suitable manner. For example, the number or amount of peptides present on a surface molecule or group of surface molecules can be measured by, for example, detecting the level or intensity of signal produced by labeled peptides and calculating the number based on the structural characteristics of the surface molecule.

The number or threshold number of peptides can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 peptides on the surface molecule. The composition can also comprise any number in between those numbers listed above.

The number or threshold number of peptides can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 peptides per square nM of the entire or a portion of the surface molecule. The composition can also comprise any number in between those numbers listed above.

The number or threshold number of peptides can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 peptides per square µM of the entire or a portion of the surface molecule. The composition can also comprise any number in between those numbers listed above.

The number or threshold number of peptides can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 peptides per cubic nM of the entire or a portion of the surface molecule. The composition can also comprise any number in between those numbers listed above.

The number or threshold number of peptides can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 peptides per cubic µM of the entire or a portion of the surface molecule. The composition can also comprise any number in between those numbers listed above.

Such numbers can be applied as well to any of the components of the disclosed compositions other than the peptides.

Disclosed are linkers for associating components of the disclosed compositions. Such linkers can be any molecule, conjugate, composition, etc. that can be used to associate components of the disclosed compositions. Generally, linkers can be used to associate components other than surface molecules to surface molecules. Useful linkers include materials that are biocompatible, have low bioactivity, have low antigenicity, etc. That is, such useful linker materials can serve the linking/association function without adding unwanted bioreactivity to the disclosed compositions. Many such materials are known and used for similar linking and association functions. Polymer materials are a particularly useful form of linker material. For example, polyethylene glycols can be used.

Linkers are useful for achieving useful numbers and densities of the components (such as peptides and accessory molecules) on surface molecules. For example, linkers of fibrous form are useful for increasing the number of components per surface molecule or per a given area of the surface molecule. Similarly, linkers having a branching form are useful for increasing the number of components per surface molecule or per a given area of the surface molecule. Linkers can also have a branching fibrous form.

Linkers of different lengths can be used to bind the disclosed components to surface molecules and to each other. A flexible linker can function well even if relatively short, while a stiffer linker can be longer to allow effective exposure and density. The length of a linker can refer to the number of atoms in a continuous covalent chain between the attachment points on the components being linked or to the length (in nanometers, for example) of a continuous covalent chain between the attachment points on the components being linked. Unless the context clearly indicates otherwise, the length refers to the shortest continuous covalent chain between the attachment points on the components being linked not accounting for side chains, branches, or loops. Due to flexibility of the linker, all of the linkers may not have same distance from the surface molecule. Thus linkers with different chain lengths can make the resulting composition more effective (by increasing density, for example). Branched linkers bearing multiple components also allow attachment of more than one component at a given site of the surface molecule. Useful lengths for linkers include at least, up to, about, exactly, or between 10, 15, 20, 25, 30, 35, 40, 45, 50, 60, 70, 80, 90, 100, 120, 140, 150, 160, 180, 200, 250, 300, 350, 400, 450, 500, 550, 600, 650, 700, 750, 800, 850, 900, 950, 1,000, 2,000, 3,000, 4,000, 5,000, 6,000, 7,000, 8,000, 9,000, and 10,000 atoms. Useful lengths for linkers include at least, up to, about, exactly, or between 10, 15, 20, 25, 30, 35, 40, 45, 50, 60, 70, 80, 90, 100, 120, 140, 150, 160, 180, 200, 250, 300, 350, 400, 450, 500, 550, 600, 650, 700, 750, 800, 850, 900, 950, 1,000, 2,000, 3,000, 4,000, 5,000, 6,000, 7,000, 8,000, 9,000, and 10,000 nanometers. Any range of these lengths and all lengths between the listed lengths are specifically contemplated.

Hydrophilic or water-solubility linkers can increase the mobility of the attached components. Examples of water-soluble, biocompatible polymers which can serve as linkers include, but are not limited to polymers such polyethylene glycol (PEG), polyethylene oxide (PEO), polyvinyl alcohol, polyhydroxyethyl methacrylate, polyacrylamide, and natural polymers such as hyaluronic acid, chondroitin sulfate, carboxymethylcellulose, and starch. Useful forms of branched tethers include star PEO and comb PEO. Star PEO can be formed of many PEO "arms" emanating from a common core.

Polyethylene glycols (PEGs) are simple, neutral polyethers which have been given much attention in biotechnical and biomedical applications (Milton Harris, J. (ed) "Poly(ethylene glycol) chemistry, biotechnical and biomedical applications" Plenum Press, New York, 1992). PEGs are soluble in most solvents, including water, and are highly hydrated in aqueous environments, with two or three water molecules bound to each ethylene glycol segment; this hydration phenomenon has the effect of preventing adsorption either of other polymers or of proteins onto PEG-modified surfaces.

Furthermore, PEGs may readily be modified and bound to other molecules with only little effect on their chemistry. Their advantageous solubility and biological properties are apparent from the many possible uses of PEGs and copolymers thereof, including block copolymers such as PEG-polyurethanes and PEG-polypropylenes. Appropriate molecular weights for PEG linkers used in the disclosed compositions can be from about 120 daltons to about 20 kilodaltons. For example, PEGs can be at least, up to, about, exactly, or between 100, 150, 200, 250, 300, 350, 400, 450, 500, 600, 700, 800, 900, 1000, 1200, 1400, 1500, 1600, 1800, 2000, 2500, 3000, 3500, 4000, 4500, 5000, 5500, 6000, 6500, 7000, 7500, 8000, 8500, 9000, 9500, 10,000, 20,000, 30,000, 40,000, and 50,000 daltons. Any range of these masses and all masses between the listed masses are specifically contemplated. PEGs are usually available as mixtures of somewhat heterogeneous masses with a stated average mass (PEG-5000, for example).

The disclosed compositions can be produced using any suitable techniques. Many techniques, reactive groups, chemistries, etc. for linking components of the types disclosed herein are known and can be used with the disclosed components and compositions.

Protein crosslinkers that can be used to crosslink other molecules, elements, moieties, etc. to the disclosed compositions, surface molecules, peptides, internalization elements, tissue penetration elements, cargo compositions, AMT peptides, compositions, peptides, amino acid sequences, etc. are known in the art and are defined based on utility and structure and include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy) ethyl] sulfone), BSOCOES (Bis[2-(succinimdooxycarbonyloxy) ethyl]sulfone), SULFO DST (Disulfosuccinimdyltartrate), DST (Disuccinimidyltartrate), SULFO EGS (Ethylene glycolbis(succinimidylsuccinate)), EGS (Ethylene glycolbis (sulfosuccinimidylsuccinate)), DPDPB (1,2-Di[3'-(2'-pyridyldithio) propionamido]butane), BSSS (Bis (sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl) aminobenzoate), SULFO SIAB (N-Sulfosuccinimidyl(4-iodoacetyl)aminobenzoate), SMCC (Succinimidyl-4-(N-maleimidomethyl) cyclohexane-1-carboxylate), SULFO SMCC (Sulfosuccinimidyl-4-(N-maleimidomethyl) cyclohexane-1-carboxylate), NHS LC SPDP (Succinimidyl-6-[3-(2-pyridyldithio) prop]onamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl) cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS (N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent; Methyl-p-hydroxybenzimidate hydrochloride, 98%), DMA (Dimethyladipimidate hydrochloride).

Components of the disclosed compositions, such as surface molecules, peptides, internalization elements, tissue penetration elements, etc., can also be coupled using, for example, maleimide coupling. By way of illustration, components can be coupled to lipids by coupling to, for example, 1,2-distearoyl-sn-glycero-3-phosphoethanolamine-N-[maleimide(polyethylene glycol)$_{2000}$; DSPE-PEG2000-maleimide] (Avanti Polar Lipids) by making use of a free cysteine sulfhydryl group on the component. The reaction can be performed, for example, in aqueous solution at room temperature for 4 hours. This coupling chemistry can be used to couple components of co-compositions and cargo compositions.

Components of the disclosed compositions, such as surface molecules, peptides, internalization elements, tissue penetration elements, etc., can also be coupled using, for example, amino group-functionalized dextran chemistry. Particles, such as, for example, nanoparticles, nanoworms, and micelles, can be coated with amino group functionalized dextran. Attachment of PEG to aminated particles increases the circulation time, presumably by reducing the binding of plasma proteins involved in opsonization (Moghimi et al., Pharm. Rev. 53, 283-318 (2001)). The particles can have surface modifications, for example, for reticuloendothelial system avoidance (PEG) and homing (AMT and CRV peptides), endosome escape (pH-sensitive peptide; for example, Pirollo et al., Cancer Res. 67, 2938-43 (2007)), a detectable agent, a therapeutic compound, or a combination. To accommodate all these functions on one particle, optimization studies can be conducted to determine what proportion of the available linking sites at the surface of the particles any one of these elements should occupy to give the best combination of targeting and payload delivery.

The provided peptides and polypeptides can have additional N-terminal, C-terminal, or intermediate amino acid sequences, e.g., amino acid linkers or tags. The term "amino acid linker" refers to an amino acid sequences or insertions that can be used to connect or separate two distinct peptides, polypeptides, or polypeptide fragments, where the linker does not otherwise contribute to the essential function of the composition. The term "amino acid tag" refers to a distinct amino acid sequence that can be used to detect or purify the provided polypeptide, wherein the tag does not otherwise contribute to the essential function of the composition. The provided peptides and polypeptides can further have deleted N-terminal, C-terminal or intermediate amino acids that do not contribute to the essential activity of the peptides and polypeptides.

Components can be directly or indirectly covalently bound to surface molecules or each other by any functional group (e.g., amine, carbonyl, carboxyl, aldehyde, alcohol). For example, one or more amine, alcohol or thiol groups on the components can be reacted directly with isothiocyanate, acyl azide, N-hydroxysuccinimide ester, aldehyde, epoxide, anhydride, lactone, or other functional groups incorporated onto the surface molecules or other components. Schiff bases formed between the amine groups on the components and aldehyde groups on the surface molecule or other components can be reduced with agents such as sodium cyanoborohydride to form hydrolytically stable amine links (Ferreira et al., J. Molecular Catalysis B: Enzymatic 2003, 21, 189-199). Components can be coupled to surface molecules and other components by, for example, the use of a heterobifunctional silane linker reagent, or by other reactions that activate functional groups on either the surface molecule or the components.

Useful modes for linking components to surface molecules and to other components include heterobifunctional linkers or spacers. Such linkers can have both terminal amine and thiol reactive functional groups for reacting amines on components with sulfhydryl groups, thereby coupling the components in an oriented way. These linkers can contain a variable number of atoms. Examples of such linkers include, but are not limited to, N-Succinimidyl 3-(2-pyridyldithio)propionate (SPDP, 3- and 7-atom spacer), long-chain-SPDP (12-atom spacer), (Succinimidyloxycarbonyl-a-methyl-2-(2-pyridyldithio) toluene) (SMPT, 8-atom spacer), Succinimidyl-4-(N-maleimidomethyl)cyclohexane-1-carboxylate) (SMCC, 11-atom spacer) and Sulfosuccinimidyl-4-(N-maleimidomethyl)cyclohexane-1-carboxylate, (sulfo-SMCC, 11-atom spacer), m-Maleimidobenzoyl-N hydroxysuccinimide ester (MBS, 9-atom spacer), N-(g-maleimidobutyryloxy)succinimide ester (GMBS, 8-atom spacer), N-(g-maleimidobutyryloxy) sulfo-succinimide ester (sulfo-GMBS, 8-atom spacer), Succinimidyl 6-((iodoacetyl) amino) hexanoate (SIAX, 9-atom spacer), Succinimidyl 6-(6-(((4-iodoacetyl)amino) hexanoyl)amino)hexanoate (SIAXX, 16-atom spacer), and p-nitrophenyl iodoacetate (NPIA, 2-atom spacer). One ordinarily skilled in the art also will recognize that a number of other coupling agents or links, with different number of atoms, may be used.

Hydrophilic spacer atoms can be incorporated into linkers to increase the distance between the reactive functional groups. For example, polyethylene glycol (PEG) can be incorporated into sulfo-GMBS. Hydrophilic molecules such as PEG have also been shown to decrease non-specific binding (NSB) and increase hydrophilicity of surfaces when covalently coupled. PEG can also be used as the primary linker material.

Free amine groups of components can also be attached to surface molecules or other components containing reactive amine groups via homobifunctional linkers. Linkers such as dithiobis(succinimidylpropionate) (DSP, 8-atom spacer), disuccinimidyl suberate (DSS, 8-atom spacer), glutaraldehyde (4-atom spacer), Bis[2-(succinimidyloxycarbonyloxy) ethyl]sulfone (BSOCOES, 9-atom spacer), all requiring high pH, can be used for this purpose. Examples of homobifunctional sulfhydryl-reactive linkers include, but are not limited to, 1,4-Di-[3'-2'-pyridyldithio)propion-amido]butane (DPDPB, 16-atom spacer) and Bismaleimidohexane (BMH, 14-atom spacer). For example, these homobifunctional linkers are first reacted with a thiolated surface in aqueous solution (for example PBS, pH 7.4), and then in a second step, the thiolated antibody or protein is joined by the link. Homo- and heteromultifunctional linkers can also be used.

Direct binding of components to thiol, amine, or carboxylic acid functional groups on surface molecules and other components be used to produce compositions which exhibit viral binding (due to increased density of components, for example), resulting in enhanced sensitivity.

As an example, when necessary to achieve high peptide coupling density, additional amino groups can be added to the surface molecules (such as commercially obtained SPIO) as follows: First, to crosslink the particles before the amination step, 3 ml of the colloid (~10 mgFe/ml in double-distilled water) was added to 5 ml of 5M NaOH and 2 ml of epichlorohydrin (Sigma, St. Louis, MO). The mixture was agitated for 24 hours at room temperature to promote interaction between the organic phase (epichlorohydrin) and aqueous phase (dextran-coated particle colloid). In order to remove excess epichlorohydrin, the reacted mixture was dialyzed against double-distilled water for 24 hours using a dialysis cassette (10,000 Da cutoff, Pierce, Rockford IL). Amino groups were added to the surface of the particles as follows: 0.02 ml of concentrated ammonium hydroxide (30%) was added to 1 ml of colloid (~10 mg Fe/ml). The mixture was agitated at room temperature for 24 hours. The reacted mixture was dialyzed against double-distilled water for 24 hours. To further rinse the particles, the colloid was trapped on a MACS® Midi magnetic separation column (Miltenyi Biotec, Auburn CA), rinsed with PBS three times, and eluted from the column with 1 ml PBS.

To conjugate peptides to SPIO, the particles were re-suspended at a concentration of 1 mg Fe/ml, and heterobifunctional linker N-[a-maleimidoacetoxy]succinimide ester (AMAS; Pierce) was added (2.5 mg linker per 2 mg Fe) under vortexing. After incubation at room temperature for 40 min, the particles were washed 3 times with 10 ml PBS on a MACS column. The peptide with free terminal cysteine was then added (100 μg peptide per 2 mg Fe). After incubation overnight at 4° C. the particles were washed again and re-suspended in PBS at a concentration of 0.35 mg/ml of Fe). To quantify the number of peptide molecules conjugated to the particles, a known amount of stock or AMAS-activated particles was incubated with varying amounts of the peptide. After completion of the incubation the particles were pelleted at 100.000G using Beckman TLA 100.3 ultracentrifuge rotor (30 min) and the amount of the unbound peptide was quantified by fluorescence. To cleave the conjugated peptide from the particles, the particles were incubated at 37° C. overnight at pH 10. The concentration of free peptide in the supernatant was determined by reading fluorescence and by using the calibration curve obtained for the same peptide. The fluorescence intensity of known amounts of particles was plotted as a function of peptide conjugation density, and the slope equation was used to determine conjugation density in different batches.

The peptide can selectively home to activated macrophages. The peptide can selectively home to tumor associated macrophages. The peptide can selectively home to one or more particular types of tumor. The peptide can selectively home to the vasculature of one or more particular types of tumor. The peptide can selectively home to one or more particular stages of a tumor or cancer. The peptide can selectively home to the vasculature of one or more particular stages of a tumor or cancer. The peptide can selectively home to one or more particular stages of one or more particular types of tumor. The peptide can selectively home to the vasculature of one or more different stages of one or more particular types of tumor.

The composition can selectively home to activated macrophages. The composition can selectively home to tumor associated macrophages. The composition can selectively home to one or more particular types of tumor. The composition can selectively home to the vasculature of one or more particular types of tumor. The composition can selectively home to one or more particular stages of a tumor or cancer. The composition can selectively home to the vasculature of one or more particular stages of a tumor or cancer. The composition can selectively home to one or more particular stages of one or more particular types of tumor. The composition can selectively home to the vasculature of one or more different stages of one or more particular types of tumor.

The co-composition can selectively home to activated macrophages. The co-composition can selectively home to tumor associated macrophages. The co-composition can selectively home to one or more particular types of tumor. The co-composition can selectively home to the vasculature of one or more particular types of tumor. The co-composition can selectively home to one or more particular stages of a tumor or cancer. The co-composition can selectively home to the vasculature of one or more particular stages of a tumor or cancer. The co-composition can selectively home to one or more particular stages of one or more particular types of tumor. The co-composition can selectively home to the vasculature of one or more different stages of one or more particular types of tumor.

The AMT composition can selectively home to activated macrophages. The AMT composition can selectively home to tumor associated macrophages. The AMT composition can selectively home to one or more particular types of tumor. The AMT composition can selectively home to the vasculature of one or more particular types of tumor. The AMT composition can selectively home to one or more particular stages of a tumor or cancer. The AMT composition can selectively home to the vasculature of one or more particular stages of a tumor or cancer. The AMT composition can selectively home to one or more particular stages of one or more particular types of tumor. The AMT composition can selectively home to the vasculature of one or more different stages of one or more particular types of tumor.

The AMT peptide can selectively home to activated macrophages. The AMT peptide can selectively home to tumor associated macrophages. The AMT peptide can selectively home to one or more particular types of tumor. The AMT peptide can selectively home to the vasculature of one or more particular types of tumor. The AMT peptide can selectively home to one or more particular stages of a tumor or cancer. The AMT peptide can selectively home to the vasculature of one or more particular stages of a tumor or cancer. The AMT peptide can selectively home to one or more particular stages of one or more particular types of tumor. The AMT peptide can selectively home to the vasculature of one or more different stages of one or more particular types of tumor.

The cargo composition can selectively home to activated macrophages. The cargo composition can selectively home to tumor associated macrophages. The cargo composition can selectively home to one or more particular types of tumor. The cargo composition can selectively home to the vasculature of one or more particular types of tumor. The cargo composition can selectively home to one or more particular stages of a tumor or cancer. The cargo composition can selectively home to the vasculature of one or more particular stages of a tumor or cancer. The cargo composition can selectively home to one or more particular stages of one or more particular types of tumor. The cargo composition can selectively home to the vasculature of one or more different stages of one or more particular types of tumor.

The cargo molecule can selectively home to activated macrophages. The cargo molecule can selectively home to tumor associated macrophages. The cargo molecule can selectively home to one or more particular types of tumor. The cargo molecule can selectively home to the vasculature of one or more particular types of tumor. The cargo molecule can selectively home to one or more particular stages of a tumor or cancer. The cargo molecule can selectively home to the vasculature of one or more particular stages of a tumor or cancer. The cargo molecule can selectively home to one or more particular stages of one or more particular types of tumor. The cargo molecule can selectively home to the vasculature of one or more different stages of one or more particular types of tumor.

The surface molecule can selectively home to activated macrophages. The surface molecule can selectively home to tumor associated macrophages. The surface molecule can selectively home to one or more particular types of tumor. The surface molecule can selectively home to the vasculature of one or more particular types of tumor. The surface molecule can selectively home to one or more particular stages of a tumor or cancer. The surface molecule can selectively home to the vasculature of one or more particular stages of a tumor or cancer. The surface molecule can selectively home to one or more particular stages of one or more particular types of tumor. The surface molecule can selectively home to the vasculature of one or more different stages of one or more particular types of tumor.

The disclosed amino acid sequences, co-compositions, cargo compositions, proteins or peptides can, for example, home to brain cells, brain stem cells, brain tissue, and/or brain vasculature, kidney cells, kidney stem cells, kidney tissue, and/or kidney vasculature, skin cells, skin stem cells, skin tissue, and/or skin vasculature, lung cells, lung tissue, and/or lung vasculature, pancreatic cells, pancreatic tissue, and/or pancreatic vasculature, intestinal cells, intestinal tissue, and/or intestinal vasculature, adrenal gland cells, adrenal tissue, and/or adrenal vasculature, retinal cells, retinal tissue, and/or retinal vasculature, liver cells, liver tissue, and/or liver vasculature, prostate cells, prostate tissue, and/or prostate vasculature, endometriosis cells, endometriosis tissue, and/or endometriosis vasculature, ovary cells, ovary tissue, and/or ovary vasculature, tumor cells, tumors, tumor blood vessels, and/or tumor vasculature, bone cells, bone tissue, and/or bone vasculature, bone marrow cells, bone marrow tissue, and/or bone marrow vasculature, cartilage cells, cartilage tissue, and/or cartilage vasculature, stem cells, embryonic stem cells, pluripotent stem cells, induced pluripotent stem cells, adult stem cells, hematopoietic stem cells, neural stem cells, mesenchymal stem cells, mammary stem cells, endothelial stem cells, olfactory adult stem cells, neural crest stem cells, cancer stem cells, blood cells, erythrocytes, platelets, leukocytes, granulocytes, neutrophils, eosinphils, basophils, lymphoid cells, lymphocytes, monocytes, wound vasculature, vasculature of injured tissue, vasculature of inflamed tissue, atherosclerotic plaques, or a combination.

Accessory molecules can be any molecule, compound, component, etc. that has a useful function and that can be used in combination with an AMT composition, AMT conjugate, AMT molecule, AMT protein, AMT peptide, composition, co-composition, and/or cargo composition. Examples of useful accessory molecules include homing molecules, targeting molecules, affinity ligands, cell penetrating molecules, endosomal escape molecules, subcellular targeting molecules, nuclear targeting molecules. Different accessory molecules can have similar or different functions from each other.

Molecules that target, home, or have affinity for certain molecules, structures, cells, tissues, etc. are particularly useful as accessory molecules. In addition to the homing molecules described elsewhere herein, there are numerous molecules and compounds known that have affinity for particular target molecules, structures, cells, tissues, etc. and can aid in accumulating and/or directing the disclosed components and compositions to desired targets. For convenience, such affinity effects can be referred to as homing. Descriptions of homing and homing effects elsewhere herein can be applied to these molecules.

An affinity ligand is a molecule that interacts specifically with a particular molecule, moiety, cell tissue, etc. The molecule, moiety, cell tissue, etc. that interacts specifically with an affinity ligand is referred to herein as a target or target molecule, moiety, cell tissue, etc. It is to be understood that the term target molecule refers to both separate molecules and to portions of such molecules, such as an epitope of a protein, that interacts specifically with an affinity ligand. Antibodies, either member of a receptor/ligand pair, synthetic polyamides (Dervan and Burli, *Sequence-specific DNA recognition by polyamides*. Curr Opin Chem Biol, 3(6):688-93 (1999); Wemmer and Dervan, *Targeting the minor groove of DNA*. Curr Opin Struct Biol, 7(3):355-61 (1997)), and other molecules with specific binding affinities are examples of affinity ligands.

An affinity ligand that interacts specifically with a particular target molecule is said to be specific for that target molecule. For example, where the affinity ligand is an antibody that binds to a particular antigen, the affinity ligand is said to be specific for that antigen. The antigen is the target molecule. The affinity ligand can also be referred to as being specific for a particular target molecule. Examples of useful affinity ligands are antibodies, ligands, binding proteins, receptor proteins, haptens, aptamers, carbohydrates, lectins, folic acid, synthetic polyamides, and oligonucleotides. Useful binding proteins include DNA binding proteins. Useful DNA binding proteins include zinc finger motifs, leucine zipper motifs, and helix-turn-helix motifs. These motifs can be combined in the same affinity ligand.

Antibodies are useful as the affinity ligands. Antibodies can be obtained commercially or produced using well established methods. For example, Johnstone and Thorpe, *Immunochemistry In Practice* (Blackwell Scientific Publications, Oxford, England, 1987) on pages 30-85, describe general methods useful for producing both polyclonal and monoclonal antibodies. The entire book describes many general techniques and principles for the use of antibodies in assay systems. Numerous antibodies and other affinity ligands are known that bind to particular proteins, carbohydrates, glycoproteins, molecules, cells, tissues, etc. Such antibodies can be used in the disclosed components and compositions.

Examples of cell penetrating peptides are described in, for example, U.S. Patent Application Publication Nos. 20100061942, 20100061932, 20100048487, 20100022466, 20100016215, 20090280058, 20090186802, 20080234183, 20060014712, 20050260756, and 20030077289, which are hereby incorporated by reference in their entirety and specifically for their description of cell penetrating peptides and motifs. Examples of endosomal escape molecules are described in, for example, U.S. Patent Application Publication Nos. 20090325866, 20090317802, 20080305119, 20070292920, 20060147997, 20050038239, 20040219169, 20030148263, 20030082143, 20020132990, and 20020068272, which are hereby incorporated by reference in their entirety and specifically for their description of endosomal escape molecules and motifs. Examples of subcellular targeting molecules are described in, for example, U.S. Patent Application Publication Nos. 2009031733, 20090258926, 20090176660, 20080311136, 20070287680, 20070157328, 20070111270, 20070111251, 20060257942, 20060154340, 20060014712, 20050281805, 20050233356, 20040005309, 30030082176, and 20010021500, which are hereby incorporated by reference in their entirety and specifically for their description of subcellular targeting molecules and motifs. Examples of nuclear targeting molecules are described in, for example, U.S. Patent Application Publication Nos. 10100143454, 20100099627, 20090305329, 20090176710, 20090087899, 20070231862, 20070212332, 20060242725, 20060233807, 20060147922, 20060070133, 20060051315, 20050147993, 20050071088, 20030166601, 20030125283, 20030083261, 20030003100, 20020068272, and 20020055174, which are hereby incorporated by reference in their entirety and specifically for their description of nuclear targeting molecules and motifs.

As disclosed herein, the term "co-composition" refers to any composition of matter that can be used with the AMT peptide. Similarly, the term "cargo composition" refers to any composition of matter that can be used with the AMT peptide. Generally, for example, a co-composition or cargo composition can be any composition to be targeted to activated macrophages. For example, a co-composition or cargo composition can be a molecule, a conjugate, an association of molecules, a composition, and a mixture. Examples of co-compositions and cargo compositions include, but are not limited to, cancer chemotherapeutic agents, cytotoxic agents, pro-apoptotic agents, immunomodulatory agents, pro-inflammatory agents, immunostimulating agents, anti-inflammatory agents, anti-arthritic agents, polypeptides, nucleic acid molecules, small molecules, nanoparticles, microparticles, fluorophores, fluorescein, rhodamine, a radionuclide, Lutetium-177 ($^{177}$Lu), Rhenium-188 ($^{188}$Re), Gallium-68 ($^{68}$Ga), Yttrium-90 ($^{90}$Y), Technetium-99m ($^{99m}$Tc), Holmium-166 ($^{166}$Ho), Iodine-131 ($^{131}$I), Indium-111 ($^{111}$In), Flourine-18 ($^{18}$F), Carbon-11 ($^{11}$C), Nitrogen-13 ($^{13}$N), Oxygen-15 ($^{15}$O), Bromine-75 ($^{75}$Br), Bromine-76 ($^{76}$Br), Iodine-124 ($^{124}$I), Thalium-201 ($^{201}$Tl), Technetium-99 ($^{99}$Tc), Iodine-123 ($^{123}$I), or a combination thereof.

The disclosed AMT components can be used with any therapeutic agents since they represent a general mode and platform for aiding in delivery of therapeutic agents to cells and tissues. Thus, any therapeutic agent can be used in or with the disclosed compositions. Comprehensive lists of therapeutic agents and drugs can be found in a number of places, such as the Orange Book and other lists maintained by the U.S. Food and Drug Administration (information available at websites fda.gov/Drugs/InformationOnDrugs/ucm129662.htm and fda.gov/Drugs/InformationOnDrugs/ApprovedDrugs/default.htm) and similar lists maintained by other countries, and at clinicaltrials.gov/ (for drugs and therapeutic agents undergoing clinical trials).

In some forms, the therapeutic agents can be agents that can modulate the activity of activated macrophages. For example, the therapeutic agents can be agents that can modulate the activity of tumor associated macrophages or activated macrophages associated with infected lungs. As another example, the therapeutic agents can be siRNAs, small molecules and protein-based agents that can modulate the activity of tumor associated macrophages or activated macrophages associated with infected lungs. In some forms, the therapeutic agent inhibits expression of the phosphotidylinositide 3-kinase (PI3K) gamma gene. In some forms, the therapeutic agent inhibits PI3K gamma. In some forms, the therapeutic agent can be a PI3K gamma inhibitor (such as TG100-115), and TNF-alpha. Table 2 lists numerous PI3K gamma inhibitors.

TABLE 2

PI3K gamma inhibitors

| Inhibitor | Description | Specificity for p110γ | IC50; Ki |
|---|---|---|---|
| CZC24832 | CZC24832 is the first selective PI3Kγ inhibitor with IC50 of 27 nM, with 10-fold selectivity over PI3Kβ and >100-fold selectivity over PI3Kα and PI3Kδ. | Selective | PI3Kγ, IC50: 27 nM |
| AS-252424 | AS-252424 is a novel, potent PI3Kγ inhibitor with IC50 of 30 nM with 30-fold selectivity for PI3Kγ than PI3Kα, and low inhibitory activity towards PI3Kδ/β. | Selective | PI3Kγ, IC50: 33 nM |
| AS-604850 | AS-604850 is a selective, ATP-competitive PI3Kγ inhibitor with IC50 of 250 nM, over 80-fold selectivity for PI3Kγ than PI3Kδ/β, and 18-fold more selective for PI3Kγ than PI3Kα. | Selective | PI3Kγ, IC50: 0.25 uM |
| CAY10505 | CAY10505 is dehydroxyl of AS-252424, which is a PI3Kγ inhibitor with IC50 of 33 nM. | Selective | |
| Omipalisib (G5K2126458, G5K458) | Omipalisib (G5K2126458, G5K458) is a highly selective and potent inhibitor of p110β/β/δ/γ, mTORC1/2 with $K_i$ of 0.019 nM/0.13 nM/0.024 nM/0.06 nM and 0.18 nM/0.3 nM, respectively. Phase 1. | Pan | p110γ, Ki: 0.06 nM |
| Duvelisib (IPI-145, INK1197) | Duvelisib (IPI-145, INK1197) is a novel and selective PI3K δ/γ inhibitor with $K_i$ and IC50 of 23 pM/243 pM and 1 nM/50 nM, highly selective for PI3K δ/γ than other protein kinases. Phase 3. | Pan | PI3Kγ, Ki: 243 pM; PI3Kγ, IC50: 50 nM |
| PF-04691502 | PF-04691502 is an ATP-competitive PI3K(α/β/δ/γ)/mTOR dual inhibitor with $K_i$ of 1.8 nM/2.1 nM/1.6 nM/1.9 nM and 16 nM, little activity against either Vps34, AKT, PDK1, p70S6K, MEK, ERK, p38, or JNK. Phase 2. | Pan | PI3Kγ, Ki: 1.9 nM |
| VS-5584 (SB2343) | VS-5584 (SB2343) is a potent and selective dual PI3K/mTOR inhibitor for mTOR, PI3Kα/β/δ/γ with IC50 of 3.4 nM and 2.6-21 nM, respectively. Phase 1. | Pan | PI3Kγ, IC50: 3.0 nM |
| BEZ235 (NVP-BEZ235, Dactolisib) | BEZ235 (NVP-BEZ235) is a dual ATP-competitive PI3K and mTOR inhibitor for p110α/γ/δ/β and mTOR(p70S6K) with IC50 of 4 nM/5 nM/7 nM/ 75 nM/6 nM, respectively. Inhibits ATR with IC50 of 21 nM, while shown to be a poor inhibitor to Akt and PDK1. Phase 2. | Pan | p110γ, IC50: 5 nM |
| GSK1059615 | GSK1059615 is a dual inhibitor of PI3Kα/β/δ/γ (reversible) and mTOR with IC50 of 0.4 nM/0.6 nM/2 nM/5 nM and 12 nM, respectively. Phase 1. | Pan | PI3Kγ, IC50: 5 nM |

TABLE 2-continued

| | PI3K gamma inhibitors | | |
|---|---|---|---|
| Inhibitor | Description | Specificity for p110γ | IC50; Ki |
| Gedatolisib (PF-05212384, PKI-587) | Gedatolisib (PF-05212384, PKI-587) is a highly potent dual inhibitor of PI3Kα, PI3Kγ and mTOR with IC50 of 0.4 nM, 5.4 nM and 1.6 nM, respectively. Phase 2. | Pan | PI3Kγ, IC50: 5.4 nM |
| AS-605240 | AS-605240 selectively inhibits PI3Kγ with IC50 of 8 nM, over 30-fold and 7.5-fold more selective for PI3Kγ than PI3Kδ/β and PI3Kα, respectively. | Pan | PI3Kγ, IC50: 8 nM |
| SAR245409 (XL765) | SAR245409 (XL765) is a dual inhibitor of mTOR/PI3K, mostly for p110γ with IC50 of 9 nM; also inhibits DNA-PK and mTOR. Phase 1/2. | Pan | PI3Kγ, IC50: 9 nM |
| Apitolisib (GDC-0980, RG7422) | Apitolisib (GDC-0980, RG7422) is a potent, class I PI3K inhibitor for PI3Kα/β/δ/γ with IC50 of 5 nM/27 nM/7 nM/14 nM, respectively. Also a mTOR inhibitor with $K_i$ of 17 nM, and highly selective versus other PIKK family kinases. Phase 2. | Pan | p110γ, IC50: 14 nM |
| PI-103 | PI-103 is a multi-targeted PI3K inhibitor for p110α/β/δ/γ with IC50 of 2 nM/3 nM/3 nM/15 nM, less potent to mTOR/DNA-PK with IC50 of 30 nM/23 nM. | Pan | p110γ, IC50: 15 nM |
| PKI-402 | PKI-402 is a potent dual pan-PI3K/mTOR inhibitor targeting PI3Kα/β/γ/δ and mTOR with IC50 of 2 nM/7 nM/16 nM/14 nM and 3 nM, respectively; also potent to PI3Kα mutants E545K and H1047R. | Pan | PI3Kγ, IC50: 16 nM |
| PIK-93 | PIK-93 is the first potent, synthetic PI4K (PI4KIIIβ) inhibitor with IC50 of 19 nM; shown to inhibit PI3Kα with IC50 of 39 nM. | Pan | p110γ, IC50: 16 nM |
| PIK-90 | PIK-90 is a PI3Kα/γ/δ inhibitor with IC50 of 11 nM/18 nM/58 nM, respectively, less potent to PI3Kβ. | Pan | PI3Kγ, IC50: 18 nM |
| XL147 | XL147 is a selective and reversible class I PI3K inhibitor for PI3Kα/δ/γ with IC50 of 39 nM/36 nM/23 nM, less potent to PI3Kβ. Phase 1/2. | Pan | PI3Kγ, IC50: 23 nM |
| CH5132799 | CH5132799 inhibits class I PI3Ks, particularly PI3Kα with IC50 of 14 nM; less potent to PI3Kβδγ, while sensitive in PIK3CA mutations cell lines. Phase 1. | Pan | PI3Kγ, IC50: 36 nM |
| BGT226 (NVP-BGT226) | BGT226 (NVP-BGT226) is a novel class I PI3K/mTOR inhibitor for PI3Kα/β/γ with IC50 of 4 nM/63 nM/38 nM. Phase 1/2. | Pan | PI3Kγ, IC50: 38 nM |
| ZSTK474 | ZSTK474 inhibits class I PI3K isoforms with IC50 of 37 nM, mostly PI3Kδ. Phase1/2. | Pan | PI3Kγ, IC50: 49 nM |
| TG100713 | TG100713 is a pan-PI3K inhibitor against PI3Kγ, PI3Kδ, PI3Kα and PI3Kβ with IC 50 of 50 nM, 24 nM, 165 nM and 215 nM, respectively. | Pan | PI3Kγ, IC50: 50 nM |
| Pictilisib (GDC-0941) | Pictilisib (GDC-0941) is a potent inhibitor of PI3Kα/δ with IC50 of 3 nM, with modest selectivity against p110β (11-fold) and p110γ (25-fold). Phase 2. | Pan | p110γ, IC50: 75 nM |
| PIK-75 | PIK-75 is a p110α inhibitor with IC50 of 5.8 nM (200-fold more potently than p110β), isoform-specific mutants at Ser773, and also potently inhibits DNA-PK with IC50 of 2 nM. | Pan | p110γ, IC50: 76 nM |
| TG100-115 | TG100-115 is a PI3Kγ/δ inhibitor with IC50 of 83 nM/235 nM, with little effect on PI3Kα/β. Phase 1/2. | Pan | PI3Kγ, IC50: 83 nM |
| CAL-101 (Idelalisib, GS-1101) | CAL-101 (Idelalisib, GS-1101) is a selective p110δ inhibitor with IC50 of 2.5 nM; shown to have 40- to 300-fold greater selectivity for p110δ thanp110α/β/γ, and 400- to 4000-fold more selectivity to p110δ than C2β, hVPS34, DNA-PK and mTOR. | Pan | p110γ, IC50: 89 nM |
| PIK-294 | PIK-294 is a highly selective p110δ inhibitor with IC50 of 10 nM, 1000-, 49- and 16-fold less potent to PI3Kα/β/γ, respectively. | Pan | p110γ, IC50: 160 nM |
| BKM120 (NVP-BKM120, Buparlisib) | BKM120 is a selective PI3K inhibitor of p110α/β/δ/γ with IC50 of 52 nM/166 nM/116 nM/262 nM, respectively. Reduced potency against VPS34, mTOR, DNAPK, with little activity to PI4Kβ. Phase 2. | Pan | p110γ, IC50: 262 nM |
| CUDC-907 | CUDC-907 is a dual PI3K and HDAC inhibitor for PI3Kα and HDAC1/2/3/10 with IC50 of 19 nM and 1.7 nM/5 nM/1.8 nM/2.8 nM, respectively. Phase 1. | Pan | PI3Kγ, IC50: 311 nM |

TABLE 2-continued

PI3K gamma inhibitors

| Inhibitor | Description | Specificity for p110γ | IC50; Ki |
|---|---|---|---|
| AZD6482 | AZD6482 is a PI3Kβ inhibitor with IC50 of 10 nM, 8-, 87- and 109-fold more selective to PI3Kβ than PI3Kδ, PI3Kα and PI3Kγ. Phase 1. | Pan | PI3Kγ, IC50: 1090 nM |
| Quercetin | Quercetin, a natural flavonoid present in vegetables, fruit and wine, is a stimulator of recombinant SIRT1 and also a PI3K inhibitor with IC50 of 2.4-5.4 μM. Phase 4. | Pan | PI3Kγ, IC50: 2.4 μM |
| A66 | A66 is a potent and specific p110α inhibitor with IC50 of 32 nM, >100 fold selectivity for p110α over other class-I PI3K isoforms. | Pan | p110γ, IC50: 3.48 μM |
| PIK-293 | PIK-293 is a PI3K inhibitor, mostly for PI3Kδ with IC50 of 0.24 μM, 500-, 100- and 50-fold less potent to PI3Kα/β/γ, respectively. | Pan | p110γ, IC50: 10 μM |
| PI-3065 | PI-3065 is a selective p110δ inhibitor with IC50 of 15 nM, >70-fold selectivity over other PI3K family members. | Pan | p110γ, IC50: 27542 nM |
| IC-87114 | IC-87114 is a selective PI3Kδ inhibitor with IC50 of 0.5 μM, 58-fold more selective for PI3Kδ than PI3Kγ, and over 100-fold more selective than PI3Kα/β. | Pan | PI3Kγ, IC50: 29 μM |
| 3-Methyladenine (3-MA) | 3-Methyladenine is a selective PI3K inhibitor for Vps34 and PI3Kγ with IC50 of 25 μM and 60 μM; blocks class I PI3K consistently, whereas suppression of class III PI3K is transient, and also blocks autophagosome formation. | Pan | PI3Kγ, IC50: 60 μM |

Co-compositions and cargo compositions can be moieties. As used herein, the term "moiety" is used broadly to mean a physical, chemical, or biological material that generally imparts a biologically useful function to a linked co-composition or a linked cargo composition. A moiety can be any natural or non-natural material including, without limitation, a biological material, such as a cell, phage or other virus; an organic chemical such as a small molecule; a nanoparticle, a radionuclide; a nucleic acid molecule or oligonucleotide; a polypeptide; or a peptide. For example, moieties that affect the target, such as moieties with therapeutic effect, or that facilitate detection, visualization or imaging of the target, such as fluorescent molecule or radionuclides.

Components of the disclosed co-compositions and cargo compositions can be combined, linked and/or coupled in any suitable manner. For example, moieties and other molecules can be associated covalently or non-covalently, directly or indirectly, with or without a linker moiety.

In some embodiments, a co-composition or cargo composition can comprise a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab; paclitaxel such as Abraxane; Doxil.

A co-composition or cargo composition can comprise a therapeutic agent. Useful therapeutic agents can be, for example, a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, Pseudomonas exotoxin A, cholera toxin, ligand fusion toxins such as DAB389EGF, *Ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed compositions and methods.

In some forms, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic peptides; immunomodulatory peptides, pro-inflammatory peptides, immunostimulating peptides; anti-inflammatory peptides; immunosuppressing peptides; and anti-angiogenic polypeptides. As non-limiting examples, useful therapeutic polypeptides can be a cytokine such as tumor necrosis factor-α (TNF-α), tumor necrosis factor-β (TNF-β), granulocyte macrophage colony stimulating factor (GM-CSF), granulocyte colony stimulating factor (G-CSF), interferon-α. (IFN-α); interferon-γ (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, Pseudomonas exotoxin A, cholera toxin, a ligand fusion toxin such as DAB389EGF or ricin; a pro-apoptotic polypeptide, such as $_D$(KLAKLAK)$_2$ (SEQ ID NO:3); an immunomodulatory peptide; a pro-inflammatory peptide, an immunostimulating peptide; an anti-inflammatory peptide; an immunosuppressing peptide; or an anti-angiogenic polypeptide such as angiostatin, endostatin, thrombospondin, platelet factor 4; anastellin; or one of those described further herein or known in the art. It is understood that these and other polypeptides with biological activity can be a "therapeutic polypeptide."

A therapeutic agent useful in the disclosed co-compositions and cargo compositions can be an anti-angiogenic agent. As used herein, the term "anti-angiogenic agent" means a molecule that reduces or prevents angiogenesis, which is the growth and development of blood vessels. The co-compositions and cargo compositions can be used to treat or diagnose any disease, condition, or disorder associated with angiogenesis. For example, macular degeneration and diabetic vascular complications can be diagnosed and/or treated. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

Some other examples of useful therapeutic agents include nitrogen mustards, nitrosoureas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Chlomaphazine, Cholophosphamide, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Estramustine, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, mechlorethamine oxide hydrochloride, Melphalan, Mercaptopurine, Methotrexate, Mitomycin, Mitotane, Mitoxantrone, Novembiehin, Oxaliplatin, Paclitaxel, Pamidronate, Pentostatin, Phenesterine, Plicamycin, Prednimustine, Procarbazine, Rapamycin, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Trofosfamide, Vinblastine, Vincristine, Vindesine, Vinorelbine, VP-16, and Xeloda. Alkylating agents such as Thiotepa and; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, trietylenephosphoramide, triethylenethiophosphaoramide and trimethylolomelamine; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Caminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Gemcitabine; 6-thioguanine; Mercaptopurine; Methotrexate; platinum analogs such as Cisplatin and Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylornithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above. Useful co-compositions and cargo compositions include, for example, doxorubicin, Herceptin, and liposomal doxorubicin.

The co-composition or cargo composition can also comprise a boron containing compound. Boron containing compounds have received increasing attention as therapeutic agents over the past few years as technology in organic synthesis has expanded to include this atom (Boron Therapeutics on the horizon, Groziak, M. P.; American Journal of Therapeutics (2001) 8, 321-328). The most notable boron containing therapeutic is the boronic acid bortezomib which was recently launched for the treatment of multiple myeloma. This breakthrough demonstrates the feasibility of using boron containing compounds as pharmaceutical agents. Boron containing compounds have been shown to have various biological activities including herbicides (Organic boron compounds as herbicides. Barnsley, G. E.; Eaton, J. K.; Airs, R. S.; (1957), DE 1016978 19571003), boron neutron capture therapy (Molecular Design and Synthesis of B-10 Carriers for Neutron Capture Therapy. Yamamoto, Y.; Pure Appl. Chem., (1991) 63, 423-426), serine protease inhibition (Borinic acid inhibitors as probes of the factors involved in binding at the active sites of subtilisin Carlsberg and alpha-chymotrypsin. Simpelkamp, J.; Jones, J. B.; Bioorganic & Medicinal Chemistry Letters, (1992), 2(11), 1391-4; Design, Synthesis and Biological Evaluation of Selective Boron-containing Thrombin Inhibitors. Weinand, A.; Ehrhardt, C.; Metternich, R.; Tapparelli, C.; Bioorganic and Medicinal Chemistry, (1999), 7, 1295-1307), acetylcholinesterase inhibition (New, specific and reversible bifunctional alkylborinic acid inhibitor of acetylcholinesterase. Koehler, K. A.; Hess, G. P.; Biochemistry (1974), 13, 5345-50) and as antibacterial agents (Boron-Containing Antibacterial Agents: Effects on Growth and Morphology of Bacteria Under Various Culture Conditions. Bailey, P. J.; Cousins, G.; Snow, G. A.; and White, A. J.; Antimicrobial Agents and Chemotherapy, (1980), 17, 549-553). The boron containing compounds with antibacterial activity can be sub-divided into two main classes, the diazaborinines, which have been known since the 1960's, and dithienylborinic acid complexes. This latter class has been expanded to include many different diarylborinic acid complexes with potent antibacterial activity (Preparation of diarylborinic acid esters as DNA methyl transferase inhibitors. Benkovic, S. J.; Shapiro, L.; Baker, S. J.; Wahnon, D. C.; Wall, M.; Shier, V. K.; Scott, C. P.; Baboval, J.; PCT Int. Appl. (2002), WO 2002044184).

The co-composition or cargo composition can also have one or more isotopes. Such isotopes can be useful, for example, as a therapeutic agent, as a detectable agent, or both. Examples of useful isopes include Lutetium-177 ($^{177}$Lu), Rhenium-188 ($^{188}$Re), Gallium-68 ($^{68}$Ga), Yttrium-90 ($^{90}$Y), Technetium-99m ($^{99m}$Tc), Holmium-166 ($^{166}$Ho), Iodine-131 ($^{131}$I), Indium-111 ($^{111}$In), Flourine-18 ($^{18}$F), Carbon-11 ($^{11}$C), Nitrogen-13 ($^{13}$N), Oxygen-15 ($^{15}$O), Bromine-75 ($^{75}$Br), Bromine-76 ($^{76}$Br), Iodine-124 ($^{124}$I), Thalium-201 ($^{201}$Tl), Technetium-99 ($^{99}$Tc), and Iodine-123 ($^{123}$I).

The co-composition or cargo composition can also comprise a detectable agent. A variety of detectable agents are useful in the disclosed methods. As used herein, the term "detectable agent" refers to any molecule which can be detected. Useful detectable agents include moieties that can be administered in vivo and subsequently detected. Detectable agents useful in the disclosed compositions and imaging methods include yet are not limited to radiolabels and fluorescent molecules. The detectable agent can be, for example, any moiety that facilitates detection, either directly or indirectly, preferably by a non-invasive and/or in vivo visualization technique. For example, a detectable agent can be detectable by any known imaging techniques, including, for example, a radiological technique. Detectable agents can include, for example, a contrast agent. The contrast agent can be, for example, Feridex. In some embodiments, for instance, the detectable agent comprises a tantalum compound. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, iron oxide and Gd can be used as a non-radioactive detectable agent in certain embodiments. Detectable agents can also include radioactive isotopes, enzymes, fluorophores, and quantum dots (Qdot®). For example, the detection moiety can be an enzyme, biotin, metal, or epitope tag. Other known or newly discovered detectable markers are contemplated for use with the provided compositions. In some embodiments, for instance, the detectable agent comprises a barium compound, e.g., barium sulfate.

The detectable agent can be (or the co-composition or cargo composition can include) one or more imaging agents. Examples of imaging agents include radiologic contrast agent, such as diatrizoic acid sodium salt dihydrate, iodine, and barium sulfate, a fluorescing imaging agent, such as Lissamine Rhodamine PE, a fluorescent or non-fluorescent stain or dye, for example, that can impart a visible color or that reflects a characteristic spectrum of electromagnetic radiation at visible or other wavelengths, for example, infrared or ultraviolet, such as Rhodamine, a radioisotope, a positron-emitting isotope, such as $^{18}$F or $^{124}$I (although the short half-life of a positron-emitting isotope may impose some limitations), a metal, a ferromagnetic compound, a paramagnetic compound, such as gadolinium, a superparamagnetic compound, such as iron oxide, and a diamagnetic compound, such as barium sulfate. Imaging agents can be selected to optimize the usefulness of an image produced by a chosen imaging technology. For example, the imaging agent can be selected to enhance the contrast between a feature of interest, such as a gastrointestinal polyp, and normal gastrointestinal tissue. Imaging can be accomplished using any suitable imaging techniques such as X-Ray, computed tomography (CT), MRI, Positron Emission Tomography (PET) or SPECT. In some forms, the co-composition or cargo composition can be coupled to a nuclear medicine imaging agent such as Indium-III or Technetium-99, to PET imaging agents, or to MRI imaging agents such as nanoparticles.

Examples of imaging techniques include magnetic resonance imaging (MRI), computerized tomography (CT), single photon emission computerized tomography (SPECT), and positron emission tomography (PET). Imaging agents generally can be classified as either being diagnostic or therapeutic in their application. Because of radiation's damaging effect on tissues, it is useful to target the biodistribution of radiopharmaceuticals as accurately as possible. PET can use imaging agents labeled with, for example, the positron-emitters such as $^{18}$F, $^{11}$C, $^{13}$N and $^{15}$O, $^{75}$Br, $^{76}$Br and $^{124}$I. SPECT can use imaging agents labeled with, for example, the single-photon-emitters such as $^{201}$Tl, $^{99}$Tc, $^{123}$I, and $^{131}$I.

Glucose-based and amino acid-based compounds can be used as imaging agents. Amino acid-based compounds are more useful in analyzing tumor cells, due to their faster uptake and incorporation into protein synthesis. Of the amino acid-based compounds, $^{11}$C- and $^{18}$F-containing compounds have been used with success. $^{11}$C-containing radiolabeled amino acids suitable for imaging include, for example, L-[1-$^{11}$C]leucine (Keen et al. *J. Cereb. Blood Flow Metab.* 1989 (9):429-45), L-[1-$^{11}$C]tyrosine (Wiesel et al. *J. Nucl. Med.* 1991 (32):2041-49), L-[methyl-$^{11}$C]methionine (Comar et al. *Eur. J. Nucl. Med.* 1976 (1):11-14) and L[1-$^{11}$C]methionine (Bolster et al. *Appl. Radiat. Isot.* 1986 (37):1069-70).

PET involves the detection of gamma rays in the form of annihilation photons from short-lived positron emitting radioactive isotopes including, but not limited to, $^{18}$F with a half-life of approximately 110 minutes, $^{11}$C with a half-life of approximately 20 minutes, $^{13}$N with a half-life of approximately 10 minutes and $^{15}$O with a half-life of approximately 2 minutes, using the coincidence method. For PET imaging studies, compounds such as [$^{11}$C]meta-hydroxyephedrine (HED) and 2-[$^{18}$F]fluoro-2-deoxy-D-glucose (FDG) can be used. SPECT can use longer-lived isotopes including, but not limited to, $^{99}$mTc with a half-life of approximately 6 hours and $^{201}$Tl with a half-life of approximately 74 hours. Radio-iodinated meta-iodobenzylguanidine (MIBG) is a radiotracing agent that can be used in nuclear medicine imaging studies.

As used herein, "administered with, "administered together with," and like terms means that one component is administered in the same composition as another component. As used herein, "administered at the same time as" and like terms means that one component is administered at the same time as another component. By at the same time is meant simultaneously and/or overlapping in time. As used herein, "administered during the same treatment period," "administered during overlapping treatment periods," or like terms means that one component is administered during the period when the other component remains therapeutically effective. The period when a component remains therapeutically effective refers to the period before the component is turned over, cleared, broken down, altered, etc. to a subtherapeutic amount or concentration.

The disclosed AMT compositions and co-compositions and cargo compositions can be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells). The AMT compositions and co-compositions and cargo compositions can be used therapeutically in combination with a pharmaceutically acceptable carrier. Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

The preparation can be administered to a subject or organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to a subject or organism.

Herein the term "active ingredient" refers to the preparation accountable for the biological effect. For example AMT peptides, AMT compositions, AMT conjugates, AMT molecules, AMT proteins, compositions, co-compositions, and cargo compositions that have a biological effect can be considered active ingredients.

As used herein, the phrases "physiologically acceptable carrier" and "pharmaceutically acceptable carrier" which can be interchangeably used refer to a carrier or a diluent that does not cause significant irritation to a subject or organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in Remington's Pharmaceutical Sciences, Mack Publishing Co., Easton, Pa., latest edition, which is incorporated herein by reference.

Any suitable route of administration can be used for the disclosed compositions. Routes of administration can, for example, include topical, enteral, local, systemic, or parenteral. For example, administration can be intratumoral, peritumoral, epicutaneous, inhalational, enema, conjunctival, eye drops, ear drops, alveolar, nasal, intranasal, vaginal, intravaginal, transvaginal, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, peridural, intravitreal, etc.

For homing to cells and tissue, particularly suitable routes of administration include parenteral, either local or systemic. For example, particularly suitable routes of administration for homing to cells and tissues include intravenous, injection, infusion, intraarterial, intramuscular, intratumoral, peritumoral, intracerebral, intraventricular, intracerebroventricular, intracardiac, subcutaneous, intraosseous, intradermal, intrathecal, intraperitoneal, intravesical, intramedullar, intraocular, intracranial, intracisternal, epidural, peridural, and intravitreal. The disclosed compositions can be used in and with any other procedure. For example, the disclosed compositions can be administered as part of HIPEC therapy. In HIPEC a heated sterile solution containing a composition of interest is continuously circulated throughout the peritoneal cavity.

Pharmaceutical compositions can be manufactured by processes well known in the art, e.g., by means of conventional mixing, dissolving, granulating, dragee-making, levigating, emulsifying, encapsulating, entrapping or lyophilizing processes.

Pharmaceutical compositions for use in the disclosed methods thus can be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients can be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

The preparations described herein can be formulated for parenteral administration, e.g., by bolus injection or continuous infusion. Formulations for injection can be presented in unit dosage form, e.g., in ampoules or in multidose containers with optionally, an added preservative. The compositions can be suspensions, solutions or emulsions in oily or aqueous vehicles, and can contain formulatory agents such as suspending, stabilizing and/or dispersing agents.

Pharmaceutical compositions for parenteral administration include aqueous solutions of the active preparation in water-soluble form. Additionally, suspensions of the active ingredients can be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions can contain substances, which increase the viscosity of the suspension, such as sodium carboxymethyl cellulose, sorbitol or dextran. Optionally, the suspension can also contain suitable stabilizers or agents which increase the solubility of the active ingredients to allow for the preparation of highly concentrated solutions.

Alternatively, the active ingredient can be in powder form for constitution with a suitable vehicle, e.g., sterile, pyrogen-free water based solution, before use.

The disclosed compositions can be provided in any suitable formulation. For example, solid, liquid, solution, gel, slow release, timed release, etc.

Pharmaceutical compositions for use in the disclosed methods include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art, especially in light of the detailed disclosure provided herein. For any preparation used in the disclosed methods, the therapeutically effective amount or dose can be estimated initially from in vitro and cell culture assays. For example, a dose can be formulated in animal models to achieve a desired circulating antibody concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl et al in The Pharmacological Basis of Therapeutics, Ch. 1 p. 1. (1975)).

Dosage amount and interval can be adjusted individually to provide plasma of antibodies which are sufficient to prevent or reduce viral entry (minimal effective concentration, MEC). The MEC will vary for each preparation, but can be estimated from in vitro data. Dosages necessary to achieve the MEC will depend on individual characteristics and route of administration. Binding assays can be used to determine plasma concentrations.

Dosage intervals can also be determined using the MEC value. Preparations should be administered using a regimen, which maintains plasma levels, target site measurements, or other suitable measure above the MEC for 10-90% of the time, preferable between 30-90% and most preferably 50-90%.

Depending on the severity and responsiveness of the condition to be treated, dosing can be of a single or a plurality of administrations, with course of treatment lasting from several days to several weeks or until cure is effected, diminution of the disease state is achieved, or other therapeutic effect is achieved.

The amount of a composition to be administered will, of course, be dependent on the subject being treated, the severity of the affliction, the manner of administration, the judgment of the prescribing physician, etc.

The co-composition or cargo composition can be a microparticle or a nanoparticle, such as a nanosphere, nanoshell, nanoworm, heat generating nanoshell, and the like. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Nanoshells can be formed with, for example, a core of a dielectric or inert material such as silicon, coated with a material such as a highly conductive metal which can be excited using radiation such as near infrared light (approximately 800 to 1300 nm). Upon excitation, the nanoshells emit heat. The resulting hyperthermia can kill the surrounding cell(s) or tissue. The combined diameter of the shell and core of the nanoshells ranges from the tens to the hundreds of nanometers. Near infrared light is advantageous for its ability to penetrate tissue. Other types of radiation can also be used, depending on the selection of the nanoparticle coating and targeted cells. Examples include x-rays, magnetic fields, electric fields, and ultrasound. The particles can also be used to enhance imaging, especially using infrared diffuse photon imaging methods. Targeting molecules can be antibodies or fragments thereof, ligands for specific receptors, or other proteins specifically binding to the surface of the cells to be targeted.

Fatty acids (i.e., lipids) that can be conjugated to the disclosed AMT compositions and co-compositions and cargo compositions include those that allow the efficient incorporation of the peptide into liposomes. Generally, the fatty acid is a polar lipid. Thus, the fatty acid can be a phospholipid. The provided compositions can comprise either natural or synthetic phospholipid. The phospholipids can be selected from phospholipids containing saturated or unsaturated mono or disubstituted fatty acids and combinations thereof. These phospholipids can be, for example, dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Alabaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided compositions can comprise palmitoyl 16:0.

The other molecules, elements, moieties, etc. can be covalently linked to or non-covalently associated with, for example, the disclosed co-compositions, cargo compositions, AMT composition, protein, peptide, or amino acid sequence. Such molecules, elements, moieties, etc. can be linked, for example, to the amino terminal end of the disclosed protein, peptide, amino acid sequence, or AMT peptide; to an internal amino acid of the disclosed protein, peptide, amino acid sequence, or AMT peptide; to the carboxy terminal end of the disclosed protein, peptide, or amino acid sequence; to the protein, peptide, amino acid sequence on the N terminal side of the AMT peptide; via a linker to the disclosed protein, peptide, amino acid sequence, or AMT peptide; or a combination. The disclosed AMT compositions can further comprise a linker connecting such molecules, elements, moieties, etc. and disclosed AMT composition, protein, peptide, amino acid sequence, or AMT peptide. The disclosed AMT composition, protein, peptide, amino acid sequence, or AMT peptide can also be conjugated to a coating molecule such as bovine serum albumin (BSA; see Tkachenko et al., (2003) J Am Chem Soc, 125, 4700-4701) that can be used to coat nanoparticles, nanoworms, nanoshells, and the like with the protein, peptide, amino acid sequence, or AMT peptide.

Protein crosslinkers that can be used to crosslink other molecules, elements, moieties, etc. to the disclosed co-compositions, cargo compositions, AMT compositions, proteins, peptides, amino acid sequences, etc. are known in the art and are defined based on utility and structure and include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy) ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl) aminobenzoate), SULFO SIAB (N-Sulfosuccinimidyl(4-iodoacetyl)aminobenzoate), SMCC (Succinimidyl-4-(N-maleimidomethyl) cyclohexane-1-carboxylate), SULFO SMCC (Sulfosuccinimidyl-4-(N-maleimidomethyl) cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl) cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS (N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent; Methyl-p-hydroxybenzimidate hydrochloride, 98%), DMA (Dimethyladipimidate hydrochloride).

Components of co-compositions or cargo composition can also be coupled using, for example, maleimide coupling. By way of illustration, components can be coupled to lipids by coupling to, for example, 1,2-distearoyl-sn-glycero-3-phosphoethanolamine-N-[maleimide(polyethylene glycol)$_{2000}$; DSPE-PEG2000-maleimide] (Avanti Polar Lipids) by making use of a free cysteine sulfhydryl group on the component. The reaction can be performed, for example, in aqueous solution at room temperature for 4 hours. This coupling chemistry can be used to couple components of co-compositions and cargo compositions.

The disclosed compounds, components, and compositions can also be coupled using, for example, amino group-functionalized dextran chemistry. Particles, such as, for example, nanoparticles, nanoworms, and micelles, can be coated with amino group functionalized dextran. Attachment of PEG to aminated particles increases the circulation time, presumably by reducing the binding of plasma proteins involved in opsonization (Moghimi et al., 2001). The particles can have surface modifications, for example, for reticuloendothelial system avoidance (PEG) and homing (AMT and CRV peptides), endosome escape (pH-sensitive peptide; for example, Pirello et al., 2007), a detectable agent, a therapeutic compound, or a combination. To accommodate all these functions on one particle, optimization studies can be conducted to determine what proportion of the available linking sites at the surface of the particles any one of these elements should occupy to give the best combination of targeting and payload delivery. The AMT peptides, amino acid sequences, proteins, molecules, conjugates, and compositions themselves can be coupled to other components as disclosed herein using any known technique or the techniques described herein (although generally not, as described elsewhere herein, to the disclosed co-compositions). A maleimide function can also be used as a coupling group. These chemistries can be used to couple AMT peptides, amino acid sequences, proteins, molecules, conjugates, and compositions to each other and to other components.

AMT peptides, amino acid sequences, and proteins can also be coupled to other components using, for example, maleimide coupling. By way of illustration, AMT peptides, amino acid sequences, and proteins can be coupled to lipids by coupling to, for example, 1,2-distearoyl-sn-glycero-3-phosphoethanolamine-N-[maleimide(polyethylene glycol)$_{2000}$; DSPE-PEG2000-maleimide] (Avanti Polar Lipids) by making use of a free cysteine sulfhydryl group on the AMT peptides, amino acid sequence, or protein. The reaction can be performed, for example, in aqueous solution at room temperature for 4 hours. This coupling chemistry can be used to couple the disclosed AMT peptides, amino acid sequences, and proteins to many other components, molecules and compositions.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. In particular, pets and livestock can be a subject. The subject can be an invertebrate, such as a worm or an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. In the context of endometriosis and endometriosis cells, it is understood that a subject is a subject that has or can have endometriosis and/or endometriosis cells.

The disclosed AMT peptides can be used to augment tumor imaging and tumor treatment with anti-cancer drugs. The effect of AMT peptides on imaging can be tested. For example, optical imaging with, for example, near infrared fluorphores using a Kodak IN VIVO Fx imager and Li-Cor Odyssey imager (e.g. Simberg et al., 2007; Sugahara et al., 2009), and MRI imaging can be used. For MRI imaging, the co-composition or cargo composition can be an MRI contrast agent such as Feridex iron oxide nanoparticles and gadolinium compounds. These compounds can be injected into tumor-bearing mice, for example, with and without a macrophage-homing AMT peptide or a combination of peptides, followed by imaging. The results can be used to determine effectiveness of treatments and to assess different treatment protocols for using AMT peptides with therapeutics as the co-composition or cargo composition.

Combinations of different AMT peptides and different co-compositions and/or cargo compositions can be tested for optimal accumulation and distribution of the co-composition or cargo composition in the target cells and tissue by, for example, varying the dose of the drug and using the dose of the peptide that gives the maximal effect. The disclosed results show that RVL-drug combinations can reduce the amount of drug needed and therefore, the side effects, while producing the same anti-tumor effect. AMT peptides can also produce effects not achievable by using the co-composition or cargo composition alone. For example, use of AMT peptides can allow higher concentrations of the co-composition or cargo composition in cells and tissues that is otherwise possible. In such cases, the effectiveness of the co-composition or cargo composition can be beyond that obtainable with conventional therapy.

EXAMPLES

The following example is put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Peptide Selectively Binding to Tumor-Associated Monocyte/Macrophage

With the goal of identifying peptides that target tumor-associated macrophages (TAMs), and determining the specificity of peptide binding in vitro and in vivo, in vitro phage display was performed on a mouse monocyte/macrophage cell line to identify peptides that bind to these cells in a cell type-specific and tissue-specific manner. The study lead to the discovery of a peptide with such properties, termed CRV (sequence: CRVLRSGSC (SEQ ID NO:1), where the two terminal cysteines form a disulfide bond to render the peptide cyclic). CRV binds to monocyte/macrophage cell lines in vitro, and selectively homes to tumors in vivo, binding to tumor-associated macrophages (TAMs).

Methods

Cell Lines and Animal Models.

J774A.1 and RAW264.7 cells were obtained from ATCC. Cells were maintained in Dulbecco's Modified Eagle Medium supplemented with 10% fetal bovine serum, 1% Glutamine-Pen-Strep and 100 ng/ml.

To produce 4T1 tumors, 1×10$^6$ 4 T1 cells (ATCC) suspended in 100 μl of PBS were injected into the mammary fat pad of wild type Balb/c female mice. C57BL/6 mice bearing atherosclerosis plaques were generated as previously described (She et al., *Journal of Controlled Release* 238: 212-20 (2016)). Animal experimentation was performed according to the procedures approved by the Animal Research Committee at the Sanford-Burnham Medical Research Institute.

Phage Display.

Phage display screening was carried out as described in the "Phage display and peptide identification" part of Result section. Phage tittering and subsequent rounds of enrichment were carried out according to our established protocol (Teesalu et al., *Methods in Enzymology* 503:35-56 (2012)). The peptide sequences between two cysteine residues were determined using high-throughput sequencing performed at the DNA analysis core facility of Sanford Burnham Prebys Medical Discovery Institute.

In Vitro Peptide Binding.

Cells were incubated on a rotator with peptides added at a final concentration of 10 µM in DMEM plus 1% BSA. For inhibition studies, biotin-CRV was added to a final concentration of 500 µM together with FAM-CRV (10 µM final). After 1 h at 4° C., cells were washed 3 times with PBS followed by flow cytometry analysis.

In Vivo Peptide Homing.

Orthotopic 4T1 tumors were used when they reached 0.5-1 cm in size. For tumor or plaque homing, 200 µg FAM-labeled peptide dissolved in 100 µl PBS was injected intravenously into mice. After 1 hour of circulation, the mice were euthanized by cardiac perfusion with PBS under anesthesia, and tumors and other organs (or plaques on the aorta) were dissected and analyzed for peptide homing.

Results

Phage Display and Peptide Identification

Figure 4:
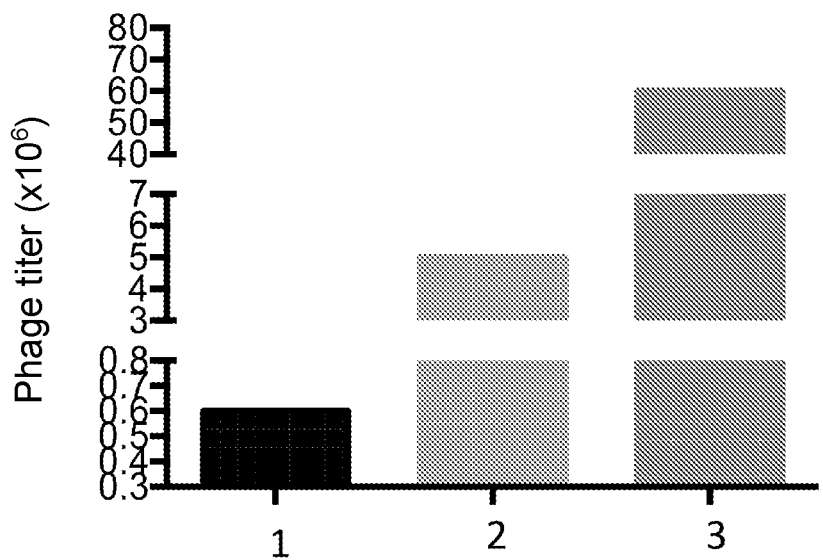
FIG. 4 is a graph of the results of phage enrichment in screening. Protocol: $10^5$ J774 A.1 cells were incubated overnight at +4° C. with $10^9$ pfu of phage library (starting with naïve CX7C library). After four rounds of washing, phage clones associated with cells were amplified for the next round. $10^5$ J774 A.1 cells were incubated with $10^9$ pfu of input phage pool through three rounds of biopanning (y-axis), which resulted in more than 100-fold enrichment.

The cell line that was used in the phage screening was J774A.1, a mouse monocyte/macrophage cell line isolated from ascites of female animals bearing reticulum cell sarcoma. A T7 phage library displaying 9-residue cyclic peptides (CX7C, two terminal cysteine residues are intended to form a disulfide bond to render the peptide cyclic; X is a random amino acid) was used for screening. J774A.1 cells ($2.5 \times 10^5$) were first incubated with $5 \times 10^{19}$ pfu (plaque-forming unit) phages displaying the sequence, RPARPAR (SEQ ID NO:4), for one hour at 4° C. RPARPAR (SEQ ID NO:4) is a prototypic CendR (C-end Rule) peptide that binds to a known receptor, neuropilin-1 (NRP1). The RPARPAR phages were inactivated with regard to their infection ability by UV exposure before incubation with cells. This way, NRP1-binding peptide sequences were avoided in the actual screening. Next, $5 \times 10^9$ pfu CX7C library was incubated with cells for another hour at 4° C. Phage tittering and subsequent rounds of enrichment were carried out according to our established protocols. The results from the enrichment as shown in FIG. 4.

After three rounds of enrichment, a high throughput sequencing of the phage clones that bound to J774A.1 cells was performed. The sequences encoding full-length peptides are shown in Table 1 (with the terminal cysteines omitted).

TABLE 1

Peptide Sequences That Bind to J774A.1 Cells

| Sequence | Count | Consensus |
|---|---|---|
| RVLRSGS (SEQ ID NO: 2) | 63428 | RVLRS |
| GGRVLRS (SEQ ID NO: 10) | 62028 | RVLRS |

TABLE 1-continued

Peptide Sequences That Bind to J774A.1 Cells

| Sequence | Count | Consensus |
|---|---|---|
| SVAYD (SEQ ID NO: 11) | 10187 | |
| RSGLRSS (SEQ ID NO: 12) | 9519 | RSGLRS |
| GRLLRSG (SEQ ID NO: 13) | 9124 | RLLRS |
| GRMLRSG (SEQ ID NO: 14) | 8922 | RMLRS |
| GGASIT (SEQ ID NO: 15) | 8677 | |
| SVGRSMRS (SEQ ID NO: 16) | 7916 | |
| GRVLRSS (SEQ ID NO: 17) | 6774 | RVLRS |

CRV Binding to Macrophages In Vitro

Figure 1B:
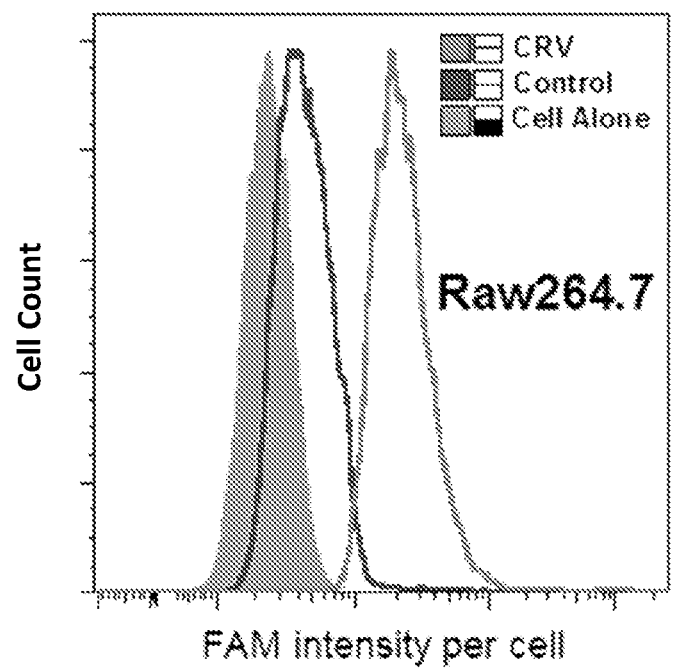
Figure 2:
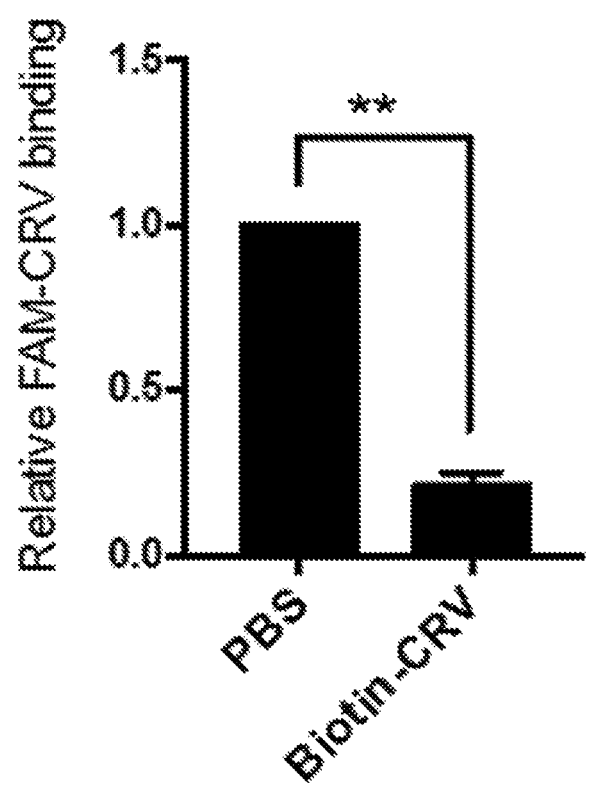

The peptide corresponding to the sequence of the top clone: CRVLRSGSC (referred to as CRV herein; SEQ ID NO:1) was then synthesized. A green carboxy-fluorescein label (FAM) was added to the N-terminus of CRV to aid detection. CRV binding to two macrophage cell lines, J774A.1 and Raw264.7 was tested. Control peptides used were ARA (ARALPSQRSR; SEQ ID NO:8) and GGSGG-SKG (SEQ ID NO:9). CRV showed a higher binding to both macrophage lines than the control peptides (FIG. 1B). Moreover, an excess of CRV with a different label (biotin) inhibited the binding of FAM-CRV to J774A.1 cells (FIG. 2). All these results indicate that CRV specifically binds to macrophages in vitro.

CRV Binding to Macrophages In Vivo

In vivo tissue distribution of CRV peptide in tumor mice was investigated. FAM-CRV was injected intravenously into mice bearing 4T1 breast tumors. After 1 hour, perfusion through the heart was performed to eliminate any circulating peptide. Heart, lung, liver, kidney, spleen, and tumor were excised and the FAM-CRV signal was imaged with an illuminator. Intravenously administered CRV was mainly found in the tumors and the kidneys, with trace amounts or none in the liver, spleen, lungs and heart.

To determine the identity of the cells that FAM-CRV localized in within the tumors, ex vivo binding of FAM-CRV to cells isolated from tumors was studied. Tumors were excised from mice bearing 4T1 breast cancer and dissociated into single cell populations using MACS dissociation kit according to the manufacturer's instructions. FAM-CRV was added to a final concentration of 10 µM into a solution of DMEM+1% BSA containing 2 million tumor cells. After 1-hour incubation at 4° C., cells were stained with various immune cell markers. The markers tested include: CD11b (pan-monocyte/macrophage marker), Ly6-G (granulocytic monocyte), CCR2 (infiltrating monocytes), F4/80, CD4 (helper T cells), CD8 (cytotoxic T cells). Cells were stained for the indicated markers and subjected to flow cytometry analysis. The analysis was performed using antibodies to the indicated macrophage markers on CRV-positive cells. The results show that nearly 80% of CRV-positive cells are CD11b+ cells, and that CRV binds equally well to different subtypes of CD11b+ cells (such as CD11b+Ly-6G+vs. CD11b+Ly-6G-).

Interestingly, it was previously found that another TAM-binding peptide, LyP-1, also homes to macrophages residing in atherosclerosis plaques of ApoE null mice fed high fat diet (She et al. (2016)). Therefore, whether CRV also binds to macrophages in this model was investigated. 200 µg FAM-labeled peptide or control peptide ARA, each dissolved in 100 µl PBS, was injected intravenously into mice. After 1 hour of circulation, the mice were euthanized by cardiac perfusion with PBS under anesthesia, and tumors and other organs (or plaques on the aorta) were dissected and imaged with illuminator for FAM signal. Unlike LyP-1, CRV does not home to plaques upon intravenous injection. This result indicates that CRV recognizes a different type of macrophage, and that allows one to distinguish different pathological conditions.

Example 2. Characterization of Peptides that are Specific for TAMs and their Optimization for Targeting Subtypes of TAMs Two peptides that are specific for TAMs (and other activated macrophages) were discovered. LyP-1 (CGNKR-TRGC; SEQ ID NO:18) was discovered and analyzed earlier (Laakkonen et al., "A tumor-homing peptide with a lymphatic vessel-related targeting specificity." *Nature Med* 8:743-751 (2002); Laakkonen et al., "Antitumor activity of a homing peptide that targets tumor lymphatics and tumor cells." *Proc. Natl. Acad. Sci. USA.* 101:9381-9386 (2004)). Variants of LyP-1 and peptidomimetics have also been developed (Laakkonen et al., "A tumor-homing peptide with a lymphatic vessel-related targeting specificity." *Nature Med* 8:743-751 (2002); Paasonen et al., "New p32/gC1qR ligands for targeted tumor delivery." *Chembiochem.* 17(7): 570-575 (2016); Zhang et al., "Lymphatic zip codes in premalignant lesions and tumors." *Cancer Res.* 66:5696-5706 (2006)). As described in Example 1 (and elsewhere herein) the TAM-homing CVR peptide (CRVLRSGSC (SEQ ID NO:1) has recently been discovered. Both LyP-1 and CRV are 9-amino acid cyclic peptides that have a K/RXXR (CendR) motif, but their sequences are otherwise quite different. They appear to recognize different subpopulations of activated macrophages. The target receptor for LyP-1 and related compounds is known.

Tumor-associated macrophages (TAMs) have emerged as a critical component of tumorigenesis and metastasis, and significantly influence treatment outcomes (Noy and Pollard, "Tumor-associated macrophages: from mechanisms to therapy." *Immunity,* 41(1):49-61 (2014); Mantovani et al., "The origin and function of tumor-associated macrophages." *Immunol Today,* 13(7):265-270 (1992); Mantovani et al., "Cancer-related inflammation." *Nature,* 454(7203):436-444 (2008); Mantovani, A. and P. Allavena, "The interaction of anticancer therapies with tumor-associated macrophages." *J Exp Med,* 212(4):435-45 (2015); Hanahan and Weinberg, Hallmarks of cancer: the next generation. *Cell,* 144(5):646-674 (2011); Coussens et al., "Neutralizing tumor-promoting chronic inflammation: a magic bullet?" *Science,* 339(6117): 286-291 (2013); DeNardo et al., "Leukocyte complexity predicts breast cancer survival and functionally regulates response to chemotherapy." *Cancer Discov,* 1(1):54-67 (2011)). While early clinical trials show that TAM targeting can be clinically valuable (Ries et al., "Targeting tumor-associated macrophages with anti-CSF-1R antibody reveals a strategy for cancer therapy." *Cancer Cell,* 25(6):846-59 (2014); Germano et al., "Role of macrophage targeting in the antitumor activity of trabectedin." *Cancer Cell,* 23(2): 249-262 (2013)), there is a need for other treatments based on TAMs. Peptides that recognize TAMs with different specificities have been developed. These can be used to define and target different subtypes of TAMs. LyP-1, one of the TAM-targeting peptides, recognizes and accumulates in certain TAMs and eliminates the TAMs, apparently by causing apoptosis. Systemic treatment of mice with Lyp-1 peptide slows down tumor growth and reduces atherosclerotic plaque (Laakkonen et al., 2002; Laakkonen et al., 2004; She et al., "Plaque-penetrating peptide inhibits development of hypoxic atherosclerotic plaque." *Journal of Controlled Release* 238:212-20 (2016)). This intrinsic activity of LyP-1 is likely to potentiate the effects of immunogene therapy that uses LyP-1 for targeting. Chemical mimics of LyP-1 are under development and may be more effective than the peptide for targeting to, and inducing apoptosis of, TAMs. The LyP-1 receptor is the cell surface protein p32. p32 has not been previously recognized as a TAM marker, but it likely defines a previously unknown subtype of TAMs. The same is true of the two proteins have been identified by affinity chromatography as leading candidates for the receptor for the CRV peptide. Interestingly, LyP-1 recognizes macrophages both in tumors and atherosclerotic plaques, whereas CRV recognizes macrophages in tumors but not in atherosclerotic plaques. Thus, these two peptides are likely to define different subtypes of TAMs. It has been realized that the elimination of the different TAM subtypes recognized by LyP-1and by CRV will support different therapeutic effects, such as different effects from immunogene therapy targeted by the two different peptides (or their cognates) on tumor growth, metastasis and tumor immunity.

Poor tissue penetration is a serious limitation of drug delivery to tumors in general, and owing to their size, nanoparticles in particular suffer from this limitation (Tong and Langer, "Nanomedicines Targeting the Tumor Microenvironment." *Cancer J.* 21(4):314-321 (2015); Ruoslahti, "Tumor penetrating peptides for improved drug delivery." *Adv Drug Deliv Rev.* pii: 50169-409X(16)30094-1 (2016)). The barriers are exit from the vasculature and penetration through tumor tissue. The frequently cited "leakiness" of tumor vessels permits passive extravasation, but tumor vessels are likely to be heterogeneous with regard to their leakiness, and it is not clear to what extent clinical tumors share the leakiness characteristic with the commonly used subcutaneous experimental tumors. Moreover, anti-angiogenic treatments cause "normalization" of tumor vasculature (Jain et al., "Normalization of Tumor Vasculature: An Emerging Concept in Antiangiogenic Therapy." *Science* 307:58 (2005)), making it likely that nanodevices will sometimes be deployed to tumors with non-leaky vasculature. High interstitial pressure in tumors constitutes a major barrier to penetration of extravasated compounds within extravascular tumor tissue, as does abundant fibrotic tissue, which is common in tumors (Provenzano et al., "Hyaluronan, fluid pressure, and stromal resistance in pancreas cancer." *Br J Cancer* 108: 1-8 (2013)). The two TAM-homing peptides readily access TAMs even when they are distant from blood vessels (Laakkonen et al., 2004 (LyP-1); unpublished observations (CRV)). The likely reason is that they use the CendR trans-tissue transport pathway to extravasate and advance through tumor tissue (Sugahara et al., "Tissue-penetrating delivery of compounds and nanoparticles into tumors." *Cancer Cell,* 16:510-520 (2009); Sugahara et al., "Co-administration of a tumor-penetrating peptide enhances the efficacy of cancer drugs." *Science,* 328: 1031-1035 (2010); Roth et al., "Transtumoral targeting enabled by a novel neuropilin-binding peptide." *Oncogene,* 31(33):3754-

3763 (2003); Pang et al., "An endocytosis pathway initiated through neuropilin-1 and regulated by nutrient availability." *Nat. Comm.* 5: 4904 (2014)).

A peptide that recognizes the M2-polarized macrophage marker (M2pep) has been reported (Ngambenjawong et al, "Serum Stability and Affinity Optimization of an M2 Macrophage-Targeting Peptide (M2pep)." *Theranostics*, 6(9): 1403-1414 (2016); Ngambenjawong et al., "Synthesis and evaluation of multivalent M2pep peptides for targeting alternatively activated M2 macrophages." *J Control Release*, 224:103-111 (2016); Cieslewicz et al., "Targeted delivery of proapoptotic peptides to tumor-associated macrophages improves survival." *Proc Natl Acad Sci USA*, 110(40):15919-24 (2013)). The receptor for M2pep is unknown, but the sequence of the M2pep is entirely different from the two TAM-targeting peptides discussed above. Therefore, each of the three peptides likely recognizes a different receptor and likely define a different subset of TAMs. The LyP-1 peptide is unique in that it causes apoptosis in the cells (TAMs) that accumulate the peptide at high levels following an intravenous injection of LyP-1 (Laakkonen et al., 2002; Laakkonen et al., 2004; Fogal et al., "Mitochondrial/Cell-Surface Protein p32/gC1qR as a Molecular Target in Tumor Cells and Tumor Stroma." *Cancer Res.* 68(17):7210-7218 (2008); She et al., 2016). This property makes it particularly well suited for targeting TAMs with the goal of silencing or eliminating the TAMs.

Figure 3:
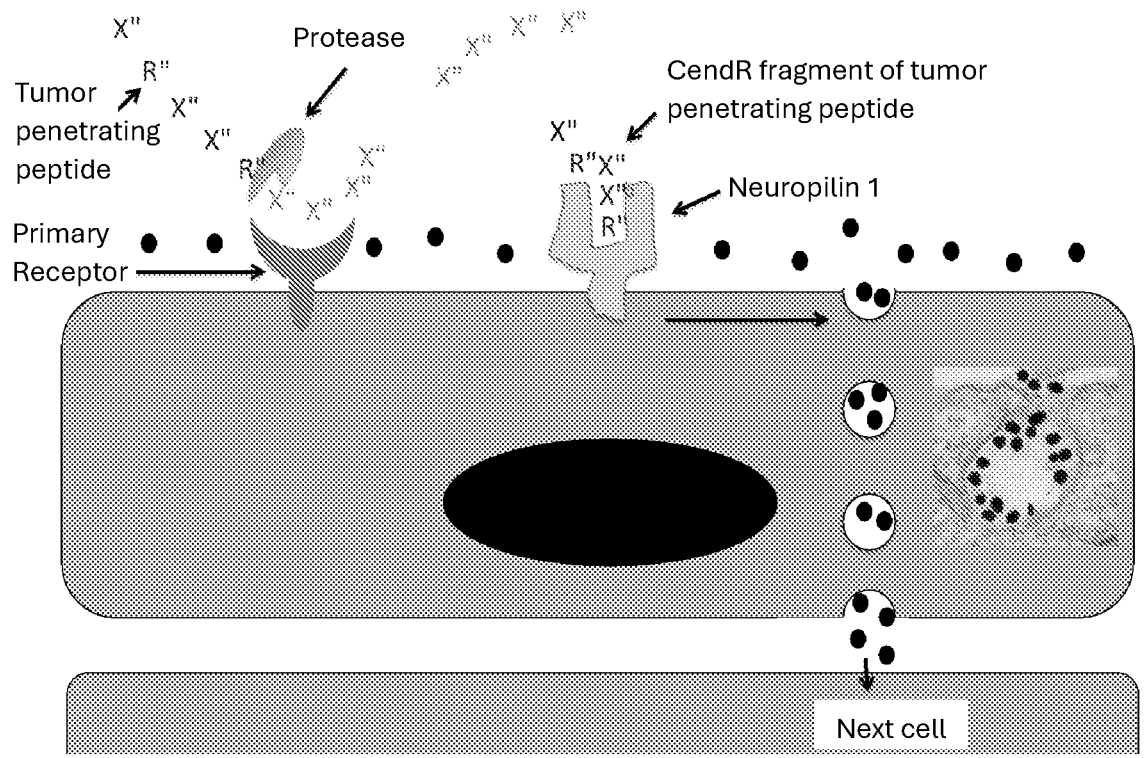
FIG. 3 is a schematic representation of the CendR trans-tissue transport pathway. CendR effect enhances the tissue penetration of cargo that is coupled to a CendR peptide, as well as cargo that is co-administered with it, without any chemical linkage (Sugahara et al., 2009; 2010). The inset is an EM picture of CendR peptide-coated gold NPs taken up into a macropinocytotic vesicle (Pang et al., 2014).

LyP-1 (CGNKRTRGC; SEQ ID NO:18) is one of the recently discovered peptides with unique tumor-penetrating properties. These peptides activate an endocytotic transport pathway related to but distinct from macropinocytosis. They accomplish this through a complex process that involves binding to a primary, tumor-specific receptor, a proteolytic cleavage that exposes a C-terminal R/KXXR/K (C-end Rule or CendR) motif, and binding to a second receptor, neuropilin-1 (NRP-1). The NRP-1 binding activates the transport pathway (Teesalu et al., C-end rule peptides mediate neuropilin-1-dependent cell, vascular, and tissue penetration." *Proc. Natl. Acad. Sci. USA* 106:16157-16162 (2009); Sugahara et al., 2009; Sugahara et al., 2010; Pang et al., 2014). This trans-tissue pathway, called the CendR pathway, mediates the exit of payloads ranging from small molecule drugs to nanoparticles (NPs) from blood vessels and their transport through extravascular tumor tissue (see FIG. 3). In this manner, the tumor-penetrating CendR peptides are capable of taking a payload deep into tumor tissue in mice, and they also penetrate into human tumors ex vivo.

This technology provides a solution to a major problem in tumor therapy, poor penetration of drugs into tumors. Remarkably, the payload to be targeted does not have to be coupled to the peptide; the peptide activates a bulk transport system that sweeps along any compound present in the blood ("bystander effect") (Sugahara et al., 2010; Akashi et al., "Anticancer effects of gemcitabine are enhanced by co-administered iRGD peptide in murine pancreatic cancer models that overexpressed neuropilin-1." *Br. J. Cancer* 110:1481-1487 (2014); Sha et al, "Tumor-penetrating peptide fused EGFR single-domain antibody enhances cancer drug penetration into 3D multicellular spheroids and facilitates effective gastric cancer therapy." *J. Control. Release* 200:188-200 (2015); Schmithals et al., "Improving drug penetrability with iRGD leverages the therapeutic response to sorafenib and doxorubicin in hepatocellular carcinoma." *Cancer Res.* 75:3147-3154 (2015)). The specificity of LyP-1 and related peptides for tumors and atherosclerotic plaques has been extensively documented in the literature (e.g., Laakkonen et al., 2002; Laakkonen et al., 2004; Fogal et al., 2008; Hamzah et al., "Specific penetration and accumulation of a homing peptide within atherosclerotic plaques of apolipoprotein E-deficient mice" Proc. Natl. Acad. Sci 108(17): 7154-7159 (2011); She et al., 2016; Sharma et al., "Tumor-penetrating Nanosystem strongly suppresses breast tumor growth." *Nano Lett.* Feb. 17, 2017).

The CRV peptide (CRVLRSGSC; SEQ ID NO:1), like LyP-1, contains a cryptic CendR motif, and it could penetrate into tumor tissues the same way as LyP-1, except that the primary receptor of the CRV peptide is likely different form the primary receptor for LyP-1. The genes that are important in CVR homing to TAMs can be determined using, for example, genome-wide CRISPR screens, as was done in another system (Pang et al., 2014).

CRV homing in tumor mice was investigated. Mice with orthotopic 4T1 breast tumors (n=2) were intravenously injected with 100 μg of CRV peptide labeled with a green fluorophor (FAM). The peptide was allowed to circulate for 1 hour, and the mice were perfused through the left ventricle of the heart to eliminate any peptide remaining in the blood. Major organs were excised and examined under visible and fluorescent light. The tumors were positive for peptide fluorescence. Some fluorescence was seen in one lung, and the kidneys were positive because peptides are eliminated through the kidneys. Fluorescence microscopy of tumor sections showed a lack of co-localization of CRV with the blood vessel marker CD31. The peptide clearly entered into the extravascular compartment of the tumor. Partial co-localization of CRV with the macrophage marker F4/80 was observed. CRV localizes in a CD45 leukocyte-rich tumor area (demarcated using anti-CD45 staining).

Synthetic CRV peptide, labeled with FAM, preferentially homes to tumors (e.g., 4T1 tumors), extravasates outside tumor blood vessels, and co-localizes with macrophages having the macrophage markers F4/80 and with lymphatic vessels in tumors. A likely explanation for the co-localization with tumor lymphatics is that bone-marrow derived macrophage/myeloid cells incorporate into the endothelium of lymphatic vessels in the process of lymphangiogenesis (Fogal et al., 2008). The CRV peptide contains a CendR motif (Teesalu et al., 2009; Sugahara et al., 2009), which is likely responsible for the extravasation and tumor penetration.

There is a synergy between nanoparticles and tumor-penetrating peptides. Nanoparticles, because of their size, are particularly prone exclusion from difficult-to-access parts of tumors. CendR peptides can mitigate this problem. Nanoparticles, in turn, are a particularly favorable cargo for peptides because multivalent presentation on the nanoparticle surface makes up for the relatively low affinity of such peptides through the avidity effect, enhancing target engagement. The same applies to compounds identified by screening small molecular weight libraries, which also tend to have only moderate affinities.

The targeting elements employed in nanoparticles have traditionally been peptides, antibodies, antibody-like binding molecules, or natural receptor ligands. Small molecular weight mimics of targeting peptides, such as LyP-1, can also be used for nanoparticle targeting to macrophages. As discussed below, a micromolar-affinity compound was identified directly from a primary screen. This compound performs quite well in tumor targeting upon multivalent presentation on a nanoparticle (Paasonen et al., "New p32/gC1qR Ligands for Targeted Tumor Drug Delivery." *Chembiochem.* 17: 570-575 (2016)).

Treatment of tumor mice with LyP-1 reduces tumor content of cells that accumulate high levels of LyP-1

(Laakkonen et al., 2004). These cells are mostly TAMs. Although tumor endothelial cells and tumor cells bind LyP-1, the peptide does not accumulate in them at nearly the levels seen in TAMs. Macrophages in atherosclerotic plaques are also sensitive to LyP-1 (She et al., 2016). The mechanism appears to be apoptosis (Laakkonen et al., 2004; She et al., 2016).

Although there are no TAM cell lines available, and although the phenotype(s) of TAMs are in flux (e.g., Franklin et al., "The cellular and molecular origin of tumor-associated macrophages." *Science*. 344:921-925 (2014)), the TAM phenotype can be approximated using the J774 A.1 and RAW 264.7 malignant macrophage cell lines by shifting their differentiation towards an M2/TAM phenotype using classical activation IFN-γ, or alternative activation with IL-4, IL-13 and lipopolysaccharide.

Antibody inhibition can be used to probe the role of particular receptors (such as NRP-1 (and NRP-2, if expressed) when using LyP-1) and integrins in the transport. Knockdown with siRNA allows testing of other suspected contributors in donor cells, recipient cells, or both. The ability to eliminate AgNPs that are not protected by a membrane (cell, exosome, etc. membrane) by dissolving them with an etching solution makes it possible to more accurately estimate the size of the intracellular nanoparticle pool than washing alone, as even vigorous washing leaves behind a substantial fraction of cell surface-bound nanoparticles (Braun et al., "Etchable plasmonic nanoparticle probes to image and quantify cellular internalization." *Nat. Mater.* 13: 904-911 (2014)).

Macrophages can be grown in suspension together with tumor cells to generate stable spheroids. Donor and recipient cells can be distinguished by labeling one with CellTracker or CellTrace™ (Life Technologies). Comparison of result with homogeneous one cell-type spheroids and donor-recipient spheroids make it possible to distinguish between uptake into cells and cell-to-cell transfer.

Genome-wide siRNA screens and follow-up studies have been used to delineate the molecular basis of the cell entry (endocytosis) part of the pathway. A highly specific assay for nanoparticle endocytosis was developed. The assay is based on cellular uptake of silver nanoparticles (AgNPs) coated with an active CendR peptide. A key element of the assay is removal of nanoparticles that bind to the cells but that were internalized. This was accomplished by using a mild and biocompatible etching solution that dissolves that nanoparticles exposed at the cell surface, but that does not have access to internalized, membrane-protected nanoparticles (Braun et al., 2014). The results show that the CendR pathway is a unique endocytic pathway that morphologically resembles macropinocytosis, but differs from it with regard to receptor dependence, regulation, and sensitivity to pharmacological inhibitors (Pang et al., 2014).

Throughout this application, various publications are referenced. The disclosures of these publications in their entireties are hereby incorporated by reference into this application in order to more fully describe the state of the art to which this invention pertains.

It must be noted that as used herein and in the appended claims, the singular forms "a", "an", and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. A composition comprising an isolated peptide comprising an activated macrophage targeting (AMT) amino acid sequence,
    wherein the AMT amino acid sequence has a length of 7 to 15 residues, and the formula $X_1$-R-$X_2$-L-R—S-$X_3$,
    wherein $X_1$ and $X_3$ are each, independently, zero to four amino acids,
    wherein $X_2$ is one or two amino acids,
    wherein the amino acids of $X_1$, $X_2$, and $X_3$ can be any amino acid,
    wherein the peptide selectively binds to activated macrophages via the AMT amino acid sequence,
    wherein the composition further comprises a co-composition, and
    wherein the peptide and the co-composition are not covalently coupled and/or associated with each other.

2. The composition of claim 1, wherein the peptide comprises RVLRSGS (SEQ ID NO:2), GGRVLRS (SEQ ID NO:10), RSGLRSS (SEQ ID NO:12), GRLLRSG (SEQ ID NO:13), GRMLRSG (SEQ ID NO:14), or GRVLRSS (SEQ ID NO:17).

3. The composition of claim 1, wherein the peptide comprises the sequence CRVLRSGSC (SEQ ID NO:1).

4. The composition of claim 1, wherein the peptide is cyclic.

5. The composition of claim 1, wherein the peptide is a modified peptide.

6. The composition of claim 1, wherein the peptide is a methylated peptide.

7. The composition of claim 6, wherein the methylated peptide comprises a methylated amino acid segment.

8. The composition of claim 1, wherein the peptide is N- or C-methylated in at least one position.

9. The composition of claim 1, further comprising a cargo composition, wherein the peptide and the cargo composition are covalently coupled or non-covalently associated with each other.

10. The composition of claim 1, wherein the peptide selectively homes to activated macrophages.

11. The composition of claim 1, wherein the peptide selectively homes to tumor associated macrophages.

12. The composition of claim 1, wherein the co-composition comprises a therapeutic agent.

13. The composition of claim 1, wherein the co-composition comprises a detectable agent.

14. A composition comprising an isolated peptide comprising an activated macrophage targeting (AMT) amino acid sequence,
    wherein the AMT amino acid sequence has a length of 7 to 15 residues, and the formula $X_1$-R-$X_2$-L-R—S-$X_3$,
    wherein $X_1$ and $X_3$ are each, independently, zero to four amino acids,
    wherein $X_2$ is one or two amino acids,
    wherein the amino acids of $X_1$, $X_2$, and $X_3$ can be any amino acid,
    wherein the peptide selectively binds to activated macrophages via the AMT amino acid sequence,
    wherein the composition further comprises a co-composition, and
    wherein the peptide and the co-composition are not covalently coupled and/or associated with each other,
    wherein the co-composition comprises a carrier, vehicle, or both.

15. The composition of claim 1, wherein the co-composition comprises a therapeutic protein, a therapeutic compound, a therapeutic composition, a cancer chemotherapeutic agent, a toxin, a cytotoxic agent, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, a pro-apototic agent, a pro-inflammatory agent, an immunostimulating agent, an anti-inflammatory agent, an immunosuppressing agent, an anti-angiogenic agent, an anti-bacterial agent, or a combination.

16. The composition of claim 1, wherein the peptide is comprised in an AMT composition.

17. The composition of claim 16, wherein the AMT composition comprises one or more cargo compositions.

18. The composition of claim 16, wherein the AMT composition further comprises one or more copies of the peptide.

19. The composition of claim 1, wherein the peptide is comprised in an AMT conjugate.

20. The composition of claim 19, wherein the AMT conjugate comprises one or more cargo compositions.

21. The composition of claim 19, wherein the AMT conjugate comprises one or more copies of the peptide.

22. The composition of claim 1, wherein the composition comprises a plurality of cargo compositions.

23. The composition of claim 1, wherein the composition comprises a plurality of copies of the peptide.

24. The composition of claim 1, wherein the composition comprises a plurality of co-compositions.

25. A composition comprising an isolated peptide comprising an activated macrophage targeting (AMT) amino acid sequence,
wherein the AMT amino acid sequence has a length of 7 to 15 residues, and the formula $X_1$-R-$X_2$-L-R—S-$X_3$,
wherein $X_1$ and $X_3$ are each, independently, zero to four amino acids,
wherein $X_2$ is one or two amino acids,
wherein the amino acids of $X_1$, $X_2$, and $X_3$ can be any amino acid,
wherein the peptide selectively binds to activated macrophages via the AMT amino acid sequence, and
wherein the composition further comprises a surface molecule.

26. The composition of claim 25, wherein the peptide is conjugated with the surface molecule.

27. The composition of claim 25, wherein the conjugated peptide is indirectly conjugated to the surface molecule via a linker.

28. The composition of claim 25, wherein the composition further comprises a plurality of linkers.

29. The composition of claim 27, wherein the linker comprises polyethylene glycol.

30. The composition of claim 1, wherein the composition binds activated macrophages.

31. The composition of claim 1, wherein the composition is internalized in cells.

32. The composition of claim 1, wherein the composition reduces an inflammatory response.

33. The composition of claim 1, wherein the composition reduces one or more effects of an infection.

34. The composition of claim 1, wherein the composition increases an inflammatory response.

35. The composition of claim 1, wherein the composition reduces tumor growth.

36. The composition of claim 25, wherein the surface molecule comprises a nanoparticle, a nanoworm, an iron oxide nanoworm, an iron oxide nanoparticle, an albumin nanoparticle, a liposome, a micelle, a phospholipid, a polymer, a microparticle, or a fluorocarbon microbubble.

37. The composition of claim 25, wherein the surface molecule comprises a liposome.

38. The composition of claim 1, further comprising one or more copies of the peptide.

39. The composition of claim 38, wherein the composition comprises at least 100 copies of the peptide.

40. The composition of claim 39, wherein the composition comprises at least 1000 copies of the peptide.

41. The composition of claim 1 further comprising one or more additional moieties.

42. The composition of claim 1 further comprising one or more moieties,
wherein the moieties are independently selected from the group consisting of a pro-apototic agent, a pro-inflammatory agent, an immunostimulating agent, an anti-inflammatory agent, an immunosuppressing agent, an anti-angiogenic agent, a pro-angiogenic agent, a cancer chemotherapeutic agent, an anti-bacterial agent, a cytotoxic agent, a polypeptide, a nucleic acid molecule, a small molecule, an image contrast agent, a fluorophore, fluorescein, rhodamine, a radionuclide, indium-111, technetium-99, carbon-11, and carbon-13.

43. The composition of claim 41, wherein at least one of the moieties is a therapeutic agent.

44. The composition of claim 43, wherein the therapeutic agent is an anti-cancer agent.

45. The composition of claim 41, wherein at least one of the moieties is a detectable agent.

46. The composition of claim 45, wherein the detectable agent is FAM.

47. The composition of claim 1 further comprising one or more copies of the peptide, wherein the peptides are conjugated to the liposome, wherein the peptides each comprise the sequence CRVLRSGSC (SEQ ID NO:1), wherein the peptides are cyclic.

* * * * *